US010383947B2

(12) United States Patent
Chang et al.

(10) Patent No.: US 10,383,947 B2
(45) Date of Patent: *Aug. 20, 2019

(54) PHARMACEUTICALS IN JOINT-LINKER CONFIGURATIONS FOR TREATING PATHOLOGICAL BLOOD CLOTS

(71) Applicant: Immunwork Inc., Taipei (TW)

(72) Inventors: Tse-Wen Chang, Taipei (TW); Hsing-Mao Chu, Taipei (TW)

(73) Assignee: Immunwork Inc., Taipei (TW)

( * ) Notice: Subject to any disclaimer, the term of this patent is extended or adjusted under 35 U.S.C. 154(b) by 301 days.

This patent is subject to a terminal disclaimer.

(21) Appl. No.: 15/212,301

(22) Filed: Jul. 18, 2016

(65) Prior Publication Data

US 2017/0056518 A1 Mar. 2, 2017

Related U.S. Application Data

(63) Continuation-in-part of application No. 14/997,764, filed on Jan. 18, 2016, now Pat. No. 9,907,858, and a continuation-in-part of application No. 14/997,827, filed on Jan. 18, 2016, now Pat. No. 10,010,626, and a continuation-in-part of application No. 14/997,849, filed on Jan. 18, 2016, now abandoned, and a continuation-in-part of application No. 14/997,874, filed on Jan. 18, 2016.

(60) Provisional application No. 62/308,349, filed on Mar. 15, 2016, provisional application No. 62/213,012, filed on Sep. 1, 2015.

(51) Int. Cl.
| A61K 47/68 | (2017.01) |
| A61K 38/48 | (2006.01) |
| A61K 31/4745 | (2006.01) |
| A61K 31/537 | (2006.01) |
| A61K 31/739 | (2006.01) |
| C07K 16/32 | (2006.01) |
| C07K 16/18 | (2006.01) |
| C07K 16/22 | (2006.01) |
| C07K 16/24 | (2006.01) |
| C07K 16/28 | (2006.01) |
| C07K 16/46 | (2006.01) |
| C07K 14/655 | (2006.01) |
| C07K 14/715 | (2006.01) |
| C07K 14/485 | (2006.01) |
| A61K 31/397 | (2006.01) |
| A61K 31/4709 | (2006.01) |
| A61K 31/4545 | (2006.01) |
| A61K 47/58 | (2017.01) |
| A61K 47/61 | (2017.01) |
| A61K 47/60 | (2017.01) |
| C07K 14/705 | (2006.01) |
| A61K 51/06 | (2006.01) |
| A61K 51/08 | (2006.01) |
| A61K 47/64 | (2017.01) |
| A61K 39/00 | (2006.01) |

(52) U.S. Cl.
CPC ........ A61K 47/6803 (2017.08); A61K 31/397 (2013.01); A61K 31/4545 (2013.01); A61K 31/4709 (2013.01); A61K 31/4745 (2013.01); A61K 31/537 (2013.01); A61K 31/739 (2013.01); A61K 47/58 (2017.08); A61K 47/60 (2017.08); A61K 47/61 (2017.08); A61K 47/64 (2017.08); A61K 47/6801 (2017.08); A61K 47/6843 (2017.08); A61K 47/6845 (2017.08); A61K 47/6849 (2017.08); A61K 47/6851 (2017.08); A61K 47/6883 (2017.08); A61K 51/065 (2013.01); A61K 51/088 (2013.01); C07K 14/485 (2013.01); C07K 14/655 (2013.01); C07K 14/705 (2013.01); C07K 14/70578 (2013.01); C07K 14/7151 (2013.01); C07K 16/18 (2013.01); C07K 16/22 (2013.01); C07K 16/241 (2013.01); C07K 16/244 (2013.01); C07K 16/2803 (2013.01); C07K 16/2809 (2013.01); C07K 16/2818 (2013.01); C07K 16/2863 (2013.01); C07K 16/2875 (2013.01); C07K 16/2887 (2013.01); C07K 16/32 (2013.01); C07K 16/468 (2013.01); A61K 2039/505 (2013.01); C07K 2317/21 (2013.01); C07K 2317/24 (2013.01); C07K 2317/31 (2013.01); C07K 2317/524 (2013.01); C07K 2317/526 (2013.01); C07K 2317/55 (2013.01); C07K 2317/622 (2013.01); C07K 2317/64 (2013.01); C07K 2317/71 (2013.01); C07K 2317/73 (2013.01); C07K 2317/732 (2013.01); C07K 2317/76 (2013.01); C07K 2317/94 (2013.01); C07K 2319/30 (2013.01); C07K 2319/32 (2013.01); C07K 2319/33 (2013.01)

(58) Field of Classification Search
None
See application file for complete search history.

(56) References Cited

U.S. PATENT DOCUMENTS

| 9,623,118 | B2 * | 4/2017 | Chang | C12Y 304/21068 |
| 9,907,858 | B2 * | 3/2018 | Chang | A61K 31/4745 |
| 9,975,951 | B2 * | 5/2018 | Chang | C07K 16/283 |
| 9,988,454 | B2 * | 6/2018 | Chang | C07K 16/283 |
| 9,994,638 | B2 * | 6/2018 | Chang | C07K 16/283 |
| 10,010,626 | B2 * | 7/2018 | Chang | A61K 31/4745 |
| 2016/0206754 | A1 * | 7/2016 | Chang | A61K 31/4745 |
| 2016/0339115 | A1 * | 11/2016 | Chang | C07K 16/283 |

(Continued)

Primary Examiner — Mark Halvorson
Assistant Examiner — Kauser M Akhoon

(57) ABSTRACT

The present disclosure provides various molecular constructs having a targeting element and an effector element. Methods for treating various diseases using such molecular constructs are also disclosed.

25 Claims, 16 Drawing Sheets
Specification includes a Sequence Listing.

(56) References Cited

U.S. PATENT DOCUMENTS

2016/0339116 A1\* 11/2016 Chang .................. C07K 16/283
2017/0056519 A1\* 3/2017 Chang ................ A61K 31/4745

\* cited by examiner

SEQUENCE LISTING

```
<160> NUMBER OF SEQ ID NOS: 37

<210> SEQ ID NO 1
<211> LENGTH: 4
<212> TYPE: PRT
<213> ORGANISM: Artificial Sequence
<220> FEATURE:
<223> OTHER INFORMATION: filler sequence-1

<400> SEQUENCE: 1

Gly Gly Gly Ser
1

<210> SEQ ID NO 2
<211> LENGTH: 4
<212> TYPE: PRT
<213> ORGANISM: Artificial Sequence
<220> FEATURE:
<223> OTHER INFORMATION: filler sequence-2

<400> SEQUENCE: 2

Gly Ser Gly Ser
1

<210> SEQ ID NO 3
<211> LENGTH: 4
```

```
<212> TYPE: PRT
<213> ORGANISM: Artificial Sequence
<220> FEATURE:
<223> OTHER INFORMATION: filler sequence-3

<400> SEQUENCE: 3

Gly Gly Ser Gly
1

<210> SEQ ID NO 4
<211> LENGTH: 5
<212> TYPE: PRT
<213> ORGANISM: Artificial Sequence
<220> FEATURE:
<223> OTHER INFORMATION: filler sequence-4

<400> SEQUENCE: 4

Gly Ser Gly Gly Ser
1               5

<210> SEQ ID NO 5
<211> LENGTH: 5
<212> TYPE: PRT
<213> ORGANISM: Artificial Sequence
<220> FEATURE:
<223> OTHER INFORMATION: filler sequence-5

<400> SEQUENCE: 5

Ser Gly Gly Ser Gly
1               5

<210> SEQ ID NO 6
<211> LENGTH: 5
<212> TYPE: PRT
<213> ORGANISM: Artificial Sequence
<220> FEATURE:
<223> OTHER INFORMATION: filler sequence-6

<400> SEQUENCE: 6

Gly Gly Gly Gly Ser
1               5

<210> SEQ ID NO 7
<211> LENGTH: 6
<212> TYPE: PRT
<213> ORGANISM: Artificial Sequence
<220> FEATURE:
<223> OTHER INFORMATION: filler sequence-7

<400> SEQUENCE: 7

Gly Gly Ser Gly Gly Ser
1               5

<210> SEQ ID NO 8
<211> LENGTH: 7
<212> TYPE: PRT
<213> ORGANISM: Artificial Sequence
<220> FEATURE:
<223> OTHER INFORMATION: filler sequence-8

<400> SEQUENCE: 8

Gly Gly Ser Gly Gly Ser Gly
1               5

<210> SEQ ID NO 9
<211> LENGTH: 8
<212> TYPE: PRT
```

```
<213> ORGANISM: Artificial Sequence
<220> FEATURE:
<223> OTHER INFORMATION: filler sequence-9

<400> SEQUENCE: 9

Ser Gly Ser Gly Gly Ser Gly Ser
1               5

<210> SEQ ID NO 10
<211> LENGTH: 9
<212> TYPE: PRT
<213> ORGANISM: Artificial Sequence
<220> FEATURE:
<223> OTHER INFORMATION: filler sequence-10

<400> SEQUENCE: 10

Gly Ser Gly Gly Ser Gly Ser Gly Ser
1               5

<210> SEQ ID NO 11
<211> LENGTH: 10
<212> TYPE: PRT
<213> ORGANISM: Artificial Sequence
<220> FEATURE:
<223> OTHER INFORMATION: filler sequence-11

<400> SEQUENCE: 11

Ser Gly Gly Ser Gly Gly Ser Gly Ser Gly
1               5                   10

<210> SEQ ID NO 12
<211> LENGTH: 11
<212> TYPE: PRT
<213> ORGANISM: Artificial Sequence
<220> FEATURE:
<223> OTHER INFORMATION: filler sequence-12

<400> SEQUENCE: 12

Gly Gly Ser Gly Gly Ser Gly Gly Ser Gly Ser
1               5                   10

<210> SEQ ID NO 13
<211> LENGTH: 12
<212> TYPE: PRT
<213> ORGANISM: Artificial Sequence
<220> FEATURE:
<223> OTHER INFORMATION: filler sequence-13

<400> SEQUENCE: 13

Ser Gly Gly Ser Gly Gly Ser Gly Ser Gly Gly Ser
1               5                   10

<210> SEQ ID NO 14
<211> LENGTH: 13
<212> TYPE: PRT
<213> ORGANISM: Artificial Sequence
<220> FEATURE:
<223> OTHER INFORMATION: filler sequence-14

<400> SEQUENCE: 14

Gly Gly Gly Gly Ser Gly Gly Ser Gly Gly Gly Gly Ser
1               5                   10

<210> SEQ ID NO 15
<211> LENGTH: 14
<212> TYPE: PRT
<213> ORGANISM: Artificial Sequence
```

```
<220> FEATURE:
<223> OTHER INFORMATION: filler sequence-15

<400> SEQUENCE: 15

Gly Gly Gly Ser Gly Ser Gly Ser Gly Ser Gly Gly Gly Ser
1               5                   10

<210> SEQ ID NO 16
<211> LENGTH: 15
<212> TYPE: PRT
<213> ORGANISM: Artificial Sequence
<220> FEATURE:
<223> OTHER INFORMATION: filler sequence-16

<400> SEQUENCE: 16

Ser Gly Ser Gly Gly Gly Gly Gly Ser Gly Gly Ser Gly Ser Gly
1               5                   10                  15

<210> SEQ ID NO 17
<211> LENGTH: 16
<212> TYPE: PRT
<213> ORGANISM: Artificial Sequence
<220> FEATURE:
<221> NAME/KEY: MOD_RES
<222> LOCATION: 1
<223> OTHER INFORMATION: ACETYLATION
<220> FEATURE:
<223> OTHER INFORMATION: polypeptide core

<400> SEQUENCE: 17

Cys Gly Gly Ser Gly Gly Ser Gly Gly Ser Lys Gly Ser Gly Ser Lys
1               5                   10                  15

<210> SEQ ID NO 18
<211> LENGTH: 19
<212> TYPE: PRT
<213> ORGANISM: Artificial Sequence
<220> FEATURE:
<221> NAME/KEY: MOD_RES
<222> LOCATION: 1
<223> OTHER INFORMATION: ACETYLATION
<220> FEATURE:
<223> OTHER INFORMATION: polypeptitde core-1

<400> SEQUENCE: 18

Cys Gly Gly Ser Gly Gly Ser Gly Gly Ser Lys Gly Ser Gly Ser Lys
1               5                   10                  15

Gly Ser Lys

<210> SEQ ID NO 19
<211> LENGTH: 31
<212> TYPE: PRT
<213> ORGANISM: Artificial Sequence
<220> FEATURE:
<221> NAME/KEY: MOD_RES
<222> LOCATION: 1
<223> OTHER INFORMATION: ACETYLATION
<220> FEATURE:
<223> OTHER INFORMATION: polypeptide core

<400> SEQUENCE: 19

Cys Gly Ser Lys Gly Ser Lys Gly Ser Lys Gly Ser Lys Gly Ser Lys
1               5                   10                  15

Gly Ser Lys Gly Ser Lys Gly Ser Lys Gly Ser Lys
                20                  25                  30

<210> SEQ ID NO 20
```

```
<211> LENGTH: 16
<212> TYPE: PRT
<213> ORGANISM: Artificial Sequence
<220> FEATURE:
<221> NAME/KEY: MOD_RES
<222> LOCATION: 1
<223> OTHER INFORMATION: Xaa is homopropargylglycine
<220> FEATURE:
<221> NAME/KEY: MOD_RES
<222> LOCATION: 1
<223> OTHER INFORMATION: ACETYLATION
<220> FEATURE:
<223> OTHER INFORMATION: polypeptide core

<400> SEQUENCE: 20

Xaa Gly Gly Ser Gly Gly Ser Gly Gly Ser Lys Gly Ser Gly Ser Lys
1               5                   10                  15

<210> SEQ ID NO 21
<211> LENGTH: 19
<212> TYPE: PRT
<213> ORGANISM: Artificial Sequence
<220> FEATURE:
<221> NAME/KEY: MOD_RES
<222> LOCATION: 1
<223> OTHER INFORMATION: Xaa is homopropargylglycine
<220> FEATURE:
<221> NAME/KEY: MOD_RES
<222> LOCATION: 1
<223> OTHER INFORMATION: ACETYLATION
<220> FEATURE:
<223> OTHER INFORMATION: polypeptide core

<400> SEQUENCE: 21

Xaa Gly Gly Ser Gly Gly Ser Gly Gly Ser Lys Gly Ser Gly Ser Lys
1               5                   10                  15

Gly Ser Lys

<210> SEQ ID NO 22
<211> LENGTH: 19
<212> TYPE: PRT
<213> ORGANISM: Artificial Sequence
<220> FEATURE:
<221> NAME/KEY: MOD_RES
<222> LOCATION: 1
<223> OTHER INFORMATION: Xaa is L-azidohomoalanine
<220> FEATURE:
<221> NAME/KEY: MOD_RES
<222> LOCATION: 1
<223> OTHER INFORMATION: ACETYLATION
<220> FEATURE:
<223> OTHER INFORMATION: polypeptide core

<400> SEQUENCE: 22

Xaa Gly Gly Ser Gly Gly Ser Gly Gly Ser Lys Gly Ser Gly Ser Lys
1               5                   10                  15

Gly Ser Lys

<210> SEQ ID NO 23
<211> LENGTH: 21
<212> TYPE: PRT
<213> ORGANISM: Artificial Sequence
<220> FEATURE:
<221> NAME/KEY: MOD_RES
<222> LOCATION: 1
<223> OTHER INFORMATION: Xaa is homopropargylglycine
<220> FEATURE:
<221> NAME/KEY: MOD_RES
<222> LOCATION: 1
<223> OTHER INFORMATION: ACETYLATION
<220> FEATURE:
```

```
<223> OTHER INFORMATION: polypeptide core

<400> SEQUENCE: 23

Xaa Gly Gly Ser Gly Gly Ser Gly Gly Ser Lys Gly Ser Gly Ser Lys
1               5                   10                  15

Gly Ser Gly Ser Cys
            20

<210> SEQ ID NO 24
<211> LENGTH: 7
<212> TYPE: PRT
<213> ORGANISM: Artificial Sequence
<220> FEATURE:
<221> NAME/KEY: MOD_RES
<222> LOCATION: 1
<223> OTHER INFORMATION: ACETYLATION
<220> FEATURE:
<223> OTHER INFORMATION: polypeptide core
<220> FEATURE:
<221> NAME/KEY: MOD_RES
<222> LOCATION: 2,4,6
<223> OTHER INFORMATION: Xaa is PEGylated amino acid with two EG units

<400> SEQUENCE: 24

Cys Xaa Lys Xaa Lys Xaa Lys
1               5

<210> SEQ ID NO 25
<211> LENGTH: 11
<212> TYPE: PRT
<213> ORGANISM: Artificial Sequence
<220> FEATURE:
<221> NAME/KEY: MOD_RES
<222> LOCATION: 1
<223> OTHER INFORMATION: ACETYLATION
<220> FEATURE:
<223> OTHER INFORMATION: polypeptide core
<220> FEATURE:
<221> NAME/KEY: MOD_RES
<222> LOCATION: 2,4,6,8,10
<223> OTHER INFORMATION: Xaa is PEGylated amino acid with six EG units

<400> SEQUENCE: 25

Cys Xaa Lys Xaa Lys Xaa Lys Xaa Lys Xaa Lys
1               5                   10

<210> SEQ ID NO 26
<211> LENGTH: 16
<212> TYPE: PRT
<213> ORGANISM: Artificial Sequence
<220> FEATURE:
<223> OTHER INFORMATION: polypeptide core-2

<400> SEQUENCE: 26

Cys Gly Ser Lys Gly Ser Lys Gly Ser Lys Gly Ser Lys Gly Ser Lys
1               5                   10                  15

<210> SEQ ID NO 27
<211> LENGTH: 250
<212> TYPE: PRT
<213> ORGANISM: Artificial Sequence
<220> FEATURE:
<223> OTHER INFORMATION: anti-fibrin scFv 102-10

<400> SEQUENCE: 27

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Tyr
```

```
            20                  25                  30
Ile Ala Trp Phe Gln His Lys Pro Gly Lys Gly Pro Arg Leu Leu Ile
        35                  40                  45

His Tyr Thr Ser Thr Leu Gln Pro Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Leu Ala Thr Tyr Tyr Cys Leu Gln Tyr Asp Asn Leu Thr Trp
                85                  90                  95

Thr Phe Gly Gly Gly Thr Lys Leu Glu Ile Lys Arg Gly Ser Thr Ser
            100                 105                 110

Gly Ser Gly Lys Pro Gly Ser Gly Glu Gly Ser Thr Lys Gly Gln Ile
        115                 120                 125

Gln Leu Val Gln Ser Gly Pro Glu Leu Lys Lys Pro Gly Glu Thr Val
    130                 135                 140

Lys Ile Ser Cys Lys Ala Ser Gly Tyr Thr Phe Thr Asn Tyr Gly Met
145                 150                 155                 160

Asn Trp Val Lys Gln Ala Pro Gly Lys Gly Leu Lys Trp Met Gly Trp
                165                 170                 175

Ile Asn Thr Tyr Thr Gly Glu Ala Thr Tyr Ala Asp Asp Phe Lys Gly
            180                 185                 190

Arg Phe Ala Phe Ser Leu Glu Thr Ser Ala Asn Thr Ala Tyr Val Gln
        195                 200                 205

Ile Asn Asn Leu Lys Asn Glu Asp Thr Ala Thr Tyr Phe Cys Ala Arg
    210                 215                 220

Leu Met Asp Tyr Trp Gly Gln Gly Thr Ser Val Thr Val Ser Ser Gly
225                 230                 235                 240

Gly Gly Gly Ser Gly Gly Gly Ser Cys
                245                 250

<210> SEQ ID NO 28
<211> LENGTH: 366
<212> TYPE: PRT
<213> ORGANISM: Artificial Sequence
<220> FEATURE:
<223> OTHER INFORMATION: reteplase-Cys

<400> SEQUENCE: 28

Ser Tyr Gln Gly Asn Ser Asp Cys Tyr Phe Gly Asn Gly Ser Ala Tyr
1               5                   10                  15

Arg Gly Thr His Ser Leu Thr Glu Ser Gly Ala Ser Cys Leu Pro Trp
            20                  25                  30

Asn Ser Met Ile Leu Ile Gly Lys Val Tyr Thr Ala Gln Asn Pro Ser
        35                  40                  45

Ala Gln Ala Leu Gly Leu Gly Lys His Asn Tyr Cys Arg Asn Pro Asp
    50                  55                  60

Gly Asp Ala Lys Pro Trp Cys His Val Leu Lys Asn Arg Arg Leu Thr
65                  70                  75                  80

Trp Glu Tyr Cys Asp Val Pro Ser Cys Ser Thr Cys Gly Leu Arg Gln
                85                  90                  95

Tyr Ser Gln Pro Gln Phe Arg Ile Lys Gly Gly Leu Phe Ala Asp Ile
            100                 105                 110

Ala Ser His Pro Trp Gln Ala Ala Ile Phe Ala Lys His Arg Arg Ser
        115                 120                 125

Pro Gly Glu Arg Phe Leu Cys Gly Gly Ile Leu Ile Ser Ser Cys Trp
```

```
                130             135             140
Ile Leu Ser Ala Ala His Cys Phe Gln Glu Arg Phe Pro His His
145                 150                 155                 160

Leu Thr Val Ile Leu Gly Arg Thr Tyr Arg Val Pro Gly Glu Glu
                165                 170                 175

Glu Gln Lys Phe Glu Val Glu Lys Tyr Ile Val His Lys Glu Phe Asp
                180                 185                 190

Asp Asp Thr Tyr Asp Asn Asp Ile Ala Leu Leu Gln Leu Lys Ser Asp
                195                 200                 205

Ser Ser Arg Cys Ala Gln Glu Ser Ser Val Val Arg Thr Val Cys Leu
                210                 215                 220

Pro Pro Ala Asp Leu Gln Leu Pro Asp Trp Thr Glu Cys Glu Leu Ser
225                 230                 235                 240

Gly Tyr Gly Lys His Glu Ala Leu Ser Pro Phe Tyr Ser Glu Arg Leu
                245                 250                 255

Lys Glu Ala His Val Arg Leu Tyr Pro Ser Ser Arg Cys Thr Ser Gln
                260                 265                 270

His Leu Leu Asn Arg Thr Val Thr Asp Asn Met Leu Cys Ala Gly Asp
                275                 280                 285

Thr Arg Ser Gly Gly Pro Gln Ala Asn Leu His Asp Ala Cys Gln Gly
290                 295                 300

Asp Ser Gly Gly Pro Leu Val Cys Leu Asn Asp Gly Arg Met Thr Leu
305                 310                 315                 320

Val Gly Ile Ile Ser Trp Gly Leu Gly Cys Gly Gln Lys Asp Val Pro
                325                 330                 335

Gly Val Tyr Thr Lys Val Thr Asn Tyr Leu Asp Trp Ile Arg Asp Asn
                340                 345                 350

Met Arg Pro Gly Gly Gly Ser Gly Gly Gly Ser Cys
                355                 360                 365

<210> SEQ ID NO 29
<211> LENGTH: 244
<212> TYPE: PRT
<213> ORGANISM: Artificial Sequence
<220> FEATURE:
<223> OTHER INFORMATION: Phage-displayed anti-fibrin scFv D10

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Gly Phe Tyr
                20                  25                  30

Val Ala Trp Tyr Gln Gln Lys Pro Gly Lys Ala Pro Lys Leu Leu Ile
                35                  40                  45

Ser Tyr Pro Ser Gly Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asp Tyr Pro Ile
                85                  90                  95

Thr Phe Gly Gln Gly Thr Lys Val Glu Ile Lys Arg Gly Ser Thr Ser
                100                 105                 110

Gly Ser Gly Lys Pro Gly Ser Gly Glu Gly Ser Thr Lys Gly Glu Val
                115                 120                 125

Gln Leu Val Glu Ser Gly Gly Gly Leu Val Gln Pro Gly Gly Ser Leu
```

```
                130                 135                 140
Arg Leu Ser Cys Ala Ala Ser Gly Phe Thr Ile Asn Asp Phe Ser Ile
145                 150                 155                 160

His Trp Val Arg Gln Ala Pro Gly Lys Gly Leu Glu Trp Val Ala Gly
                165                 170                 175

Ile Trp Pro Tyr Gly Gly Tyr Thr Phe Tyr Ala Asp Ser Val Lys Gly
                180                 185                 190

Arg Phe Thr Ile Ser Ala Asp Thr Ser Lys Asn Thr Ala Tyr Leu Arg
                195                 200                 205

Met Asn Ser Leu Arg Ala Glu Asp Thr Ala Val Tyr Tyr Cys Ala Arg
                210                 215                 220

Phe Gly Tyr Tyr Ser Phe Gly Asp Tyr Trp Gly Gln Gly Thr Leu Val
225                 230                 235                 240

Thr Val Ser Ser

<210> SEQ ID NO 30
<211> LENGTH: 20
<212> TYPE: PRT
<213> ORGANISM: Artificial Sequence
<220> FEATURE:
<221> NAME/KEY: MOD_RES
<222> LOCATION: 1
<223> OTHER INFORMATION: ACETYLATION
      ACETYLATION
<220> FEATURE:
<223> OTHER INFORMATION: synthetic
<220> FEATURE:
<221> NAME/KEY: MOD_RES
<222> LOCATION: 20
<223> OTHER INFORMATION: Xaa is azidohomoalanine

<400> SEQUENCE: 30

Gly Ser Lys Gly Ser Lys Gly Ser Lys Gly Gly Gly Ser Gly Gly
1               5                   10                  15

Gly Gly Ser Xaa
            20

<210> SEQ ID NO 31
<211> LENGTH: 20
<212> TYPE: PRT
<213> ORGANISM: Artificial Sequence
<220> FEATURE:
<223> OTHER INFORMATION: synthetic

<400> SEQUENCE: 31

Gly Ser Lys Gly Ser Lys Gly Ser Lys Gly Gly Gly Ser Gly Gly
1               5                   10                  15

Gly Gly Ser Ala
            20

<210> SEQ ID NO 32
<211> LENGTH: 7
<212> TYPE: PRT
<213> ORGANISM: Artificial Sequence
<220> FEATURE:
<221> NAME/KEY: MOD_RES
<222> LOCATION: 1
<223> OTHER INFORMATION: ACETYLATION
      ACETYLATION
<220> FEATURE:
<223> OTHER INFORMATION: synthetic
<220> FEATURE:
<221> NAME/KEY: MOD_RES
<222> LOCATION: 2,4,6
<223> OTHER INFORMATION: Xaa is PEGylated amino acid with four EG units
```

```
<400> SEQUENCE: 32

Lys Xaa Lys Xaa Lys Xaa Cys
1               5

<210> SEQ ID NO 33
<211> LENGTH: 26
<212> TYPE: PRT
<213> ORGANISM: Artificial Sequence
<220> FEATURE:
<221> NAME/KEY: MOD_RES
<222> LOCATION: 1
<223> OTHER INFORMATION: Xaa is homopropargylglycine
<220> FEATURE:
<223> OTHER INFORMATION: synthetic
<220> FEATURE:
<221> NAME/KEY: MOD_RES
<222> LOCATION: 26
<223> OTHER INFORMATION: ACETYLATION
      ACETYLATION

<400> SEQUENCE: 33

Xaa Ser Gly Gly Gly Gly Ser Gly Gly Gly Gly Lys Ser Gly Lys Ser
1               5                   10                  15
Gly Lys Ser Gly Lys Ser Gly Lys Ser Gly
            20                  25

<210> SEQ ID NO 34
<211> LENGTH: 26
<212> TYPE: PRT
<213> ORGANISM: Artificial Sequence
<220> FEATURE:
<223> OTHER INFORMATION: synthetic

<400> SEQUENCE: 34

Gly Ser Gly Gly Gly Gly Ser Gly Gly Gly Gly Lys Ser Gly Lys Ser
1               5                   10                  15
Gly Lys Ser Gly Lys Ser Gly Lys Ser Gly
            20                  25

<210> SEQ ID NO 35
<211> LENGTH: 26
<212> TYPE: PRT
<213> ORGANISM: Artificial Sequence
<220> FEATURE:
<221> NAME/KEY: MOD_RES
<222> LOCATION: 1
<223> OTHER INFORMATION: ACETYLATION
      ACETYLATION
<220> FEATURE:
<221> NAME/KEY: MOD_RES
<222> LOCATION: 1
<223> OTHER INFORMATION: Xaa is L-azidohomoalanine
<220> FEATURE:
<223> OTHER INFORMATION: synthetic

<400> SEQUENCE: 35

Xaa Ser Gly Gly Gly Gly Ser Gly Gly Gly Gly Lys Ser Gly Lys Ser
1               5                   10                  15
Gly Lys Ser Gly Lys Ser Gly Lys Ser Gly
            20                  25

<210> SEQ ID NO 36
<211> LENGTH: 10
<212> TYPE: PRT
<213> ORGANISM: Artificial Sequence
<220> FEATURE:
<223> OTHER INFORMATION: synthetic
```

```
<400> SEQUENCE: 36

Gly Gly Gly Gly Ser Gly Gly Gly Gly Ser
1               5                   10

<210> SEQ ID NO 37
<211> LENGTH: 18
<212> TYPE: PRT
<213> ORGANISM: Artificial Sequence
<220> FEATURE:
<223> OTHER INFORMATION: synthetic

<400> SEQUENCE: 37

Gly Ser Thr Ser Gly Ser Gly Lys Pro Gly Ser Gly Glu Gly Ser Thr
1               5                   10                  15

Lys Gly
```

PHARMACEUTICALS IN JOINT-LINKER CONFIGURATIONS FOR TREATING PATHOLOGICAL BLOOD CLOTS

BACKGROUND OF THE INVENTION

1. Field of the Invention

The present disclosure relates to the field of pharmaceuticals; more particularly, to multi-functional molecular constructs, e.g., those having targeting and effector elements for delivering the effector (e.g., therapeutic drug) to targeted sites.

2. Description of the Related Art

The continual advancement of a broad array of methodologies for screening and selecting monoclonal antibodies (mAbs) for targeted antigens has helped the development of a good number of therapeutic antibodies for many diseases that were regarded as untreatable just a few years ago. According to Therapeutic Antibody Database, approximately 2,800 antibodies have been studied or are being planned for studies in human clinical trials, and approximately 80 antibodies have been approved by governmental drug regulatory agencies for clinical uses. The large amount of data on the therapeutic effects of antibodies has provided information concerning the pharmacological mechanisms how antibodies act as therapeutics.

One major pharmacologic mechanism for antibodies acting as therapeutics is that, antibodies can neutralize or trap disease-causing mediators, which may be cytokines or immune components present in the blood circulation, interstitial space, or in the lymph nodes. The neutralizing activity inhibits the interaction of the disease-causing mediators with their receptors. It should be noted that fusion proteins of the soluble receptors or the extracellular portions of receptors of cytokines and the Fc portion of IgG, which act by neutralizing the cytokines or immune factors in a similar fashion as neutralizing antibodies, have also been developed as therapeutic agents.

Several therapeutic antibodies that have been approved for clinical applications or subjected to clinical developments mediate their pharmacologic effects by binding to receptors, thereby blocking the interaction of the receptors with their ligands. For those antibody drugs, Fc-mediated mechanisms, such as antibody-dependent cellular cytotoxicity (ADCC) and complement-mediated cytolysis (CMC), are not the intended mechanisms for the antibodies.

Some therapeutic antibodies bind to certain surface antigens on target cells and render Fc-mediated functions and other mechanisms on the target cells. The most important Fc-mediated mechanisms are antibody-dependent cellular cytotoxicity (ADCC) and complement-mediated cytolysis (CMC), which both will cause the lysis of the antibody-bound target cells. Some antibodies binding to certain cell surface antigens can induce apoptosis of the bound target cells.

The concept and methodology for preparing antibodies with dual specificities germinated more than three decades ago. In recent year, the advancement in recombinant antibody engineering methodologies and the drive to develop improved medicine has stimulated the development bi-specific antibodies adopting a large variety of structural configurations.

For example, the bi-valent or multivalent antibodies may contain two or more antigen-binding sites. A number of methods have been reported for preparing multivalent antibodies by covalently linking three or four Fab fragments via a connecting structure. For example, antibodies have been engineered to express tandem three or four Fab repeats.

Several methods for producing multivalent antibodies by employing synthetic crosslinkers to associate, chemically, different antibodies or binding fragments have been disclosed. One approach involves chemically cross-linking three, four, and more separately Fab fragments using different linkers. Another method to produce a construct with multiple Fabs that are assembled to one-dimensional DNA scaffold was provided. Those various multivalent Ab constructs designed for binding to target molecules differ among one another in size, half-lives, flexibility in conformation, and ability to modulate the immune system. In view of the foregoing, several reports have been made for preparing molecular constructs with a fixed number of effector elements or with two or more different kinds of functional elements (e.g., at least one targeting element and at least one effector element). However, it is often difficult to build a molecular construct with a particular combination of the targeting and effector elements either using chemical synthesis or recombinant technology. Accordingly, there exists a need in the related art to provide novel molecular platforms to build a more versatile molecule suitable for covering applications in a wide range of diseases.

SUMMARY

<I> Peptide Core-Based Multi-Arm Linkers

In the first aspect, the present disclosure is directed to a linker unit that has at least two different functional elements linked thereto. For example, the linker unit may have linked thereto two different effector elements, one targeting element and one effector element, or one effector element and a polyethylene glycol (PEG) chain for prolonging the circulation time of the linker unit. The present linker unit is designed to have at least two different functional groups such that the functional elements can be linked thereto by reacting with the respective functional groups. Accordingly, the present linker unit can serve as a platform for preparing a molecular construct with two or more functional elements.

According to various embodiments of the present disclosure, the linker unit comprises a center core and a plurality of linking arms. The center core is a polypeptide core comprising (1) a plurality of lysine (K) resides, in which each K residue and a next K residue are separated by a filler sequence comprising glycine (G) and serine (S) residues, and the number of K residues ranges from 2 to 15; or (2) the sequence of $(X_{aa}-K)_n$, where $X_{aa}$ is a PEGylated amino acid having 2 to 12 repeats of ethylene glycol (EG) unit, and n is an integral from 2 to 15. Optionally, the filler sequence consists of 2 to 20 amino acid residues. In various embodiments, the filler sequence may have the sequence of GS, GGS, GSG, or SEQ ID NOs: 1-16. According to some embodiments of the present disclosure, the center core comprises 2-15 units of the sequence of $G_{1-5}SK$; preferably, the center core comprises the sequence of $(GSK)_{2-15}$. Each of the linking arms is linked to the K residues of the center core via forming an amide linkage between the K residue and the linking arm. The linking arm linked to the center core has a maleimide, an N-hydroxysuccinimidyl (NHS) group, an azide group, an alkyne group, a tetrazine group, a cyclooctene group, or a cyclooctyne group at its free-terminus. Also, the amino acid residue at the N- or C-terminus of the center core has an azide group or an alkyne group; alternatively or additionally, the amino acid residue at the N- or C-terminus of the center core is a cysteine (C) residue, in which the thiol group of the amino acid residue is linked with a coupling arm having an azide group, an alkyne group, a tetrazine group, a cyclooctene group, or a cyclooctyne group at the free terminus of the coupling arm.

According to various embodiments of the present disclosure, the linker unit further comprises a plurality of first elements. In some embodiments, each of the first elements is linked to one of the linking arms via forming an amide bound between the linking arm and the first element. In other embodiments, each of the first elements is linked to one of the linking arms via thiol-maleimide reaction, copper catalyzed azide-alkyne cycloaddition (CuAAC) reaction, strained-promoted azide-alkyne click chemistry (SPAAC) reaction, or inverse electron demand Diels-Alder (iEDDA) reaction occurred between the linking arm and the first element.

According to some embodiments of the present disclosure, when the plurality of first elements are respectively linked to the plurality of linking arms via CuAAC or SPAAC reaction, then the amino acid residue at the N- or C-terminus of the center core is a cysteine residue, and the free terminus of the coupling arm is the tetrazine or the cyclooctene group. According to other embodiments of the present disclosure, when the plurality of first elements are respectively linked to the plurality of linking arms via iEDDA reaction, then the amino acid residue at the N- or C-terminus of the center core has the azide or the alkyne group, or the amino acid residue at the N- or C-terminus of the center core is a cysteine residue, and the free terminus of the coupling arm is the azide, the alkyne, or the cyclooctyne group.

In some embodiments, the linking arm is a PEG chain, preferably having 2 to 20 repeats of EG units. In other embodiments, the coupling linking arm is a PEG chain, preferably having 2 to 12 repeats of EG units.

Regarding amino acid residues having the azide group, non-limiting examples of said amino acid residues include L-azidohomoalanine (AHA), 4-azido-L-phenylalanine, 4-azido-D-phenylalanine, 3-azido-L-alanine, 3-azido-D-alanine, 4-azido-L-homoalanine, 4-azido-D-homoalanine, 5-azido-L-ornithine, 5-azido-d-ornithine, 6-azido-L-lysine, and 6-azido-D-lysine. As to the amino acid residues having the alkyne group, illustrative examples thereof include L-homopropargylglycine (L-HPG), D-homopropargylglycine (D-HPG), and beta-homopropargylglycine (β-HPG).

When the amino acid residues at the N- or C-terminus of the center core is the cysteine residue, the cyclooctene group at the free terminus of the coupling arm may be, a trans-cyclooctene (TCO) group, while the cyclooctyne group at the free terminus of the coupling arm may be a dibenzocyclooctyne (DBCO), difluorinated cyclooctyne (DIFO), bicyclononyne (BCN), or dibenzocyclooctyne (DICO) group. Alternatively, the tetrazine group at the free terminus of the coupling arm includes, but is not limited to, 1,2,3,4-tetrazine, 1,2,3,5-tetrazine, and 1,2,4,5-tetrazine, and derivatives thereof, such as, 6-methyl tetrazine.

According to various optional embodiments of the present disclosure, the first element is an effector element suitable for eliciting an intended effect (e.g., a therapeutic effect) in a subject. Alternatively, the first element may be a targeting element for directing the linker unit to the site of interest. According to the embodiments of the present disclosure, the first element is a single-chain variable fragment (scFv) specific for fibrin.

Optionally, the linker unit further comprises a second element that is different from the first elements. In some embodiments, the second element has an azide or alkyne group, so that it is linked to the center core or the coupling arm by coupling with the corresponding alkyne or azide group of the center core or the coupling arm via CuAAC reaction. Alternatively, in some embodiments, the second element having an azide or cyclooctyne group is linked to the center core or the coupling arm by coupling with the corresponding cyclooctyne or azide group of the center core or the coupling arm via SPAAC reaction. Still alternatively, in certain embodiments, the second element having a tetrazine or cyclooctene group is linked to the center core or the coupling arm by coupling with the corresponding cyclooctene or tetrazine group of the center core or the coupling arm via iEDDA reaction. According to the embodiments of the present disclosure, the second element is a tissue plasminogen activator or an inhibitor of Factor Xa or thrombin. Non-limiting examples of the tissue plasminogen activators include, alteplase, reteplase, tenecteplase, and lanoteplase. The inhibitor of Factor Xa is selected from the group consisting of, apixaban, edoxaban, and rivaroxaban. The inhibitor of thrombin can be argatroban or melagatran.

In certain embodiments, the linker unit further comprises an optional third element that is different from the first and second elements. In the case where the second element is directly linked to the center core, the other terminus (i.e., the free terminus that is not linked with the second element) of the center core is optionally a cysteine residue, which can be used to introduce an optional third element. Specifically, the thiol group of the cysteine residue is reacted with a maleimide group of a PEG chain; and the thus-linked PEG chain is designated as the coupling arm, which has a tetrazine group or a cyclooctene group at its free terminus. Accordingly, the third element is then linked to the coupling arm via iEDDA reaction. Preferably, the third element is an element for improving the pharmacokinetic property of the linker unit. One example of the element for improving the pharmacokinetic property is a long PEG chain having a molecular weight of about 20,000 to 50,000 Daltons.

<II> Uses of Peptide Core-Based Multi-Arm Linkers

The linker unit according to the first aspect of the present disclosure may find its utility in clinical medicine for the treatment of various diseases. Hence, the second aspect of the present disclosure is directed to a method for treating these diseases. According to various embodiments of the present disclosure, the method for treating a particular disease includes the step of administering to the subject in need thereof a therapeutically effective amount of the linker unit according to the above-mentioned aspect and embodiments of the present disclosure. As could be appreciated, said linker unit may be administered in a pharmaceutical formulation, which comprises a pharmaceutically-acceptable excipient suitable for the intended or desired administration route, in addition to the present linker unit.

According to some embodiments of the present disclosure, the present linker unit is useful in preventing the formation of blood clot. In these embodiments, the first element is an scFv specific for fibrin, and the second element is the inhibitor of Factor Xa or thrombin. The inhibitor of Factor Xa is selected from the group consisting of, apixaban, edoxaban, and rivaroxaban. The inhibitor of thrombin can be argatroban or melagatran.

According to other embodiments of the present disclosure, the linker units suitable for treating thrombosis comprise an scFv specific for fibrin as the first element, and a tissue plasminogen activator as the second element. Non-limiting examples of the tissue plasminogen activators include, alteplase, reteplase, tenecteplase, and lanoteplase.

<III> Molecular Constructs with Targeting and Effector Moieties

In the third aspect, the present disclosure is directed to a molecular construct comprising two linker units coupling to each other either directly or indirectly, in which the core of one linker unit is configured to be linked with at least one targeting element while the core of the other linker unit is configured to be linked with at least one effector element. The present molecular construct is advantageous in that the two linker units are coupled to each other via an iEDDA reaction, a SPAAC reaction, or a CuAAC reaction. This design allows for a facile synthesis of a molecular construct with a complex structure. According to the principles and spirits of the present disclosure, the two linker units respectively carrying different numbers and/or types of functional elements can be independently prepared, and then conjugated together. In this way, it becomes feasible for a skilled artisan to construct libraries of molecular constructs respectively carrying different functional elements, and then select and combine two molecular constructs (or linker units) from the libraries to generate a desired constructs, depending on the needs and/or intended applications. Moreover, the number of functional elements per linker unit may be controlled by adjusting the number of specific functional group(s) of the core.

According to one embodiment of the present disclosure, the molecular construct comprises a first linker unit and a second linker unit. Specifically, the first linker unit comprises (1) a first center core, (2) one or more linking arms (hereinafter, the first linking arms) linked to the first center core, (3) one or more elements (hereinafter, the first elements) linked to the first linking arm(s), and (4) optionally a coupling arm (hereinafter, the first coupling arm) linked to the first center core; the second linker unit comprises (1) a second center core, (2) one or more linking arms (hereinafter, the second linking arms) linked to the second center core, (3) one or more elements (hereinafter, the second elements) linked to the second linking arm(s), and (4) optionally a coupling arm (hereinafter, the second coupling arm) linked to the second center core. The first and second linker units are coupled to each other via iEDDA, SPAAC, or CuAAC reaction occurred between any of the followings: the first and second center cores, the first coupling arm and the second center core, the first and second coupling arms, or the first center core and the second coupling arm.

According to the embodiments of the present disclosure, both the first and second center cores have a plurality of amine groups. Each of the linking arms is linked to the center core via forming an amide bond therebetween, for example, between the N-hydroxysuccinimidyl (NHS) group and the amine group. After being linked to the center core, the linking arm thus has an NHS, a maleimide, an azide, an alkyne, a tetrazine, a cyclooctene, or a cyclooctyne group at the free terminus thereof.

In the presence of the NHS group, the first element and the second element are respectively linked to the first and second linking arms via forming an amide bond between the element (i.e., the first element and the second element) and the linking arm (i.e., the first linking arm or the second linking arm). In the case where the linking arm has a maleimide, an azide, an alkyne, a tetrazine, a cyclooctene, or a cyclooctyne group at its free terminus, the first element and the second element are respectively linked to the first and second linking arms via the thiol-maleimide, CuAAC, iEDDA, or SPAAC reaction occurred between the element (i.e., the first element and the second element) and the linking arm (i.e., the first linking arm or the second linking arm).

According to some embodiments of the present disclosure, each of the linking arms is a PEG chain having 2-20 repeats of EG units. According to other embodiments of the present disclosure, each of the coupling arms is a PEG chain having 2-12 repeats of EG units.

According to various embodiments of the present disclosure, each of the first and second center cores may be a compound core or a polypeptide core. In some examples, both the first and second center cores are compounds cores of the same or different compound(s). In certain preferred embodiments, both the first and second center cores are polypeptide cores having the same or different sequence(s). Alternatively, one of the two cores is a compound core, while the other is a polypeptide core.

Non-limiting examples of the compound suitable for use as the present compound core include, benzene-1,3,5-triamine, 2-(aminomethyl)-2-methylpropane-1,3-diamine, tris(2-aminoethyl)-amine, benzene-1,2,4,5-tetraamine, 3,3',5,5'-tetraamine-1,1'-biphenyl, tetrakis-(2-aminoethyl) methane, tetrakis(ethylamine)-hydrazine, N,N,N',N',-tetrakis-(aminoethyl)-ethylenediamine, benzene-1,2,3,4,5,6-hexaamine, 1-N,1-N,3-N,3-N,5-N,5-N-hexakis-(methylamine)-benzene-1,3,5-triamine, 1-N,1-N,2-N,2-N,4-N,4-N,5-N,5-N-octakis-(methylamine)-benzene-1,2,4,5-triamine, and N,N-bis[(1-amino-3,3-diaminoethyl)-pentyl]methane-diamine.

In the case where the center core is a compound core, the coupling arm is linked to one of the plurality of amine groups of the center core by forming an amide bond between the coupling arm and the center core. Meanwhile, the free terminus of the coupling arm has an azide, an alkyne, a cyclooctene, a cyclooctyne, or a tetrazine group.

According to some embodiments of the present disclosure, the polypeptide suitable for use as the present polypeptide core comprises a plurality of lysine (K) residues; optionally, 2 to 15 K residues. Also, each K residue and the next K residue are separated by a filler sequence comprising glycine (G) and serine (S) residues; optionally, the filler sequence consists of 2 to 20 amino acid residues. In various embodiments, the filler sequence may have the sequence of GS, GGS, GSG, or SEQ ID NOs: 1-16. In some embodiments, the polypeptide comprises 2-15 units of the sequence of $G_{1-5}SK$, for example, $(GSK)_{2-15}$. Alternatively, the polypeptide core may comprise the sequence of $(X_{aa}-K)_n$, where $X_{aa}$ is a PEGylated amino acid having 2 to 12 repeats of ethylene glycol (EG) unit, and n is an integral from 2 to 15.

In the case where the center core is a polypeptide core, it may comprise a cysteine residue at its N- or C-terminus. In these instances, the coupling arm is linked to the cysteine residue of the center core via the thiol-maleimide reaction. The coupling arm linked to the cysteine residue has an azide, an alkyne, a cyclooctene, a cyclooctyne, or a tetrazine group at the free-terminus thereof.

The first and second linker units may be coupled via various configurations, which are described in detail below, depending on the presence or absence of the first and second coupling arms. For a linker unit having a compound core, it is preferable that it is linked with another linker unit via a coupling arm (i.e., the first or second coupling arm), while for a linker unit having a polypeptide core, the need for a coupling arm becomes optional.

When the first and second linker units respectively comprise the coupling arms, then one of the coupling arms (say, for example, the first coupling arm) has a tetrazine group at the free-terminus thereof, and the other coupling arm (in this case, the second coupling arm) has a cyclooctene group at the free-terminus thereof, such that the two linker units are coupled via the iEDDA reaction occurred between the two coupling arms (i.e., the first and second coupling arms). Preferably, the tetrazine group is 1,2,3,4-tetrazine, 1,2,3,5-tetrazine, and 1,2,4,5-tetrazine, or derivatives thereof, such as, 6-methyl tetrazine; and the cyclooctene group is TCO. The same rule also applies in the case where the free termini of both coupling arms respectively have an azide group and an alkyne group; in this instance, the two linker units are coupled via the CuAAC reaction occurred between the two coupling arms (i.e., the first and second coupling arms). Alternatively, one of the coupling arms (for example, the first coupling arm) has an azide group, and the other coupling arm (in this case, the second coupling arm) has a cyclooctyne group (preferably, DBCO, DIFO, BCN, or DICO); accordingly, the two coupling arm can be coupled via the SPAAC reaction. These configurations may occur between two linker units, where both units have either compound cores or polypeptide cores, as well as in situations where one linker unit has a compound core, while the other has a polypeptide core.

When only one linker unit has the coupling arm (as an example, the first linker unit with the first coupling arm), the center core of the other linker unit (for example, the second center core) is a polypeptide core. In this case, the first amino acid residue at the N- or C-terminus of one of the second center core is an amino acid residue having an azide group or an alkyne group. In some embodiments, the amino acid residue having the azide or alkyne group would undergo CuAAC reaction with the corresponding alkyne or azide group of the first coupling arm of the first linker unit, thereby coupling the first and second linker units. Alternatively, the first amino acid residue at the N- or C-terminus of one of the second center core is an amino acid residue having an azide group, which can be linked to the coupling arm of the first linker unit having a cyclooctyne group (preferably, DBCO, DIFO, BCN, or DICO) at the free-terminus via the SPAAC reaction. This configuration may occur between two linker units, where both units have polypeptide cores, or in situations where one linker unit has a compound core, while the other has a polypeptide core.

It is also possible that the first and second linker units are coupled without the presence of any coupling arms (that is, the first and second coupling arms). In other words, the first and second coupling arms are directly linked with each other. This configuration mostly occurs between two polypeptide cores. Specifically, one of the two center cores (say, for example, the first center core) has an amino acid residue having an azide group at the N- or C-terminus thereof, while the other center core (such as the second center core) has an amino acid residue having an alkyne group at the N- or C-terminus thereof. In this way, the azide group of the first center core reacts with the alkyne group of the second center core, thereby coupling the first and second linker units.

Non-limiting examples of amino acid residues having the azide group include, L-azidohomoalanine (AHA), 4-azido-L-phenylalanine, 4-azido-D-phenylalanine, 3-azido-L-alanine, 3-azido-D-alanine, 4-azido-L-homoalanine, 4-azido-D-homoalanine, 5-azido-L-ornithine, 5-azido-d-ornithine, 6-azido-L-lysine, and 6-azido-D-lysine. Illustrative examples of amino acid residues having the alkyne group include, but are not limited to, L-homopropargylglycine (L-HPG), D-homopropargylglycine (D-HPG), and beta-homopropargylglycine (β-HPG).

According to some embodiments of the present disclosure, one of the first and second linker units of the molecular construct further comprises an additional linking arm (hereinafter, the third linking arm) linked to the first or the second linker unit.

Like the first and second linking arms, the third linking arm is configured to be linked with an element either via forming an amide bond therebetween, or via the thiol-maleimide, CuAAC, iEDDA, or SPAAC reaction. In some embodiments, the additional element is a second targeting element or a second effector element, which is used to enhance the targeting or therapeutic effect of the present molecular construct. Alternatively, a long PEG chain having a molecular weight of about 20,000 to 50,000 Daltons can be used us the additional element so as to enhance the stability of the present molecular construct.

In other embodiments, the present molecular construct further comprises a third linker unit. The third linker unit comprises (1) a third center core, (2) one or more linking arms (hereinafter, the third linking arms) linked to the third center core, (3) one or more elements (hereinafter, the third elements) linked to the third linking arm(s), and (4) optionally a coupling arm (hereinafter, the third coupling arm) linked to the third center core. In this case, the third linker unit is linked to the first or the second linker unit via CuAAC reaction, iEDDA reaction, or SPAAC reaction occurred between any of the followings: the first or the second coupling arm and the third coupling arm, the first or the second center core and the third coupling arm, the first or the second center coupling arm and the third center core, or the first or the second center core and the third center core.

Regarding the third linking arm of the third linker unit, it may have an NHS, a maleimide, an azide, an alkyne, a cyclooctene, a cyclooctyne, or a tetrazine group at the free terminus thereof. Accordingly, the third linking arm may be directly linked to the third element either via forming an amide bond therebetween, or via the thiol-maleimide, CuAAC, iEDDA, or SPAAC reaction.

According to various embodiments of the present disclosure, the first, second, and optionally, the third center core may be the same or different.

<IV> Uses of Molecular Constructs with Targeting and Effector Moieties

The molecular construct according to the third aspect of the present disclosure may find its utility in clinical medicine for the treatment of diseases. Hence, the fourth aspect of the present disclosure is directed to a method for treating diseases. According to various embodiments of the present disclosure, the method for treating a particular disease includes the step of administering to the subject in need thereof a molecular construct according to the third aspect of the present disclosure and embodiments thereof in a therapeutically effective amount. As could be appreciated, said molecular construct may be administered in a pharmaceutical formulation, which comprises a pharmaceutically-acceptable excipient suitable for the intended or desired administration route, in addition to the present molecular construct.

Various illustrative combinations of the first and second elements of the present molecular construct for treating some particular diseases are disclosed below for facilitating the understanding of some embodiments of the present disclosure.

According to some embodiments of the present disclosure, the present linker unit is useful in preventing the formation of blood clot. In these embodiments, the first element is an scFv specific for fibrin, and the second element is the inhibitor of Factor Xa or thrombin. The inhibitor of Factor Xa is selected from the group consisting of, apixaban, edoxaban, and rivaroxaban. The inhibitor of thrombin can be argatroban or melagatran.

According to other embodiments of the present disclosure, the linker units suitable for treating thrombosis comprise an scFv specific for fibrin as the first element, and a tissue plasminogen activator as the second element. Non-limiting examples of the tissue plasminogen activators include, alteplase, reteplase, tenecteplase, and lanoteplase.

BRIEF DESCRIPTION OF THE DRAWINGS

The present description will be better understood from the following detailed description read in light of the accompanying drawings briefly discussed below.

Figure 1A:
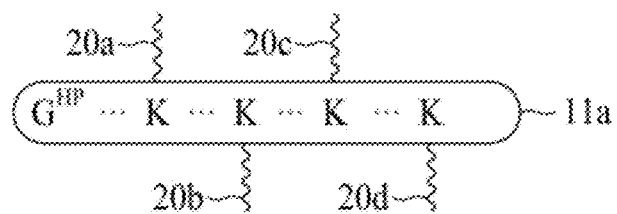
FIG. 1A to FIG. 1K are schematic diagrams illustrating linker units according to certain embodiments of the present disclosure.

In accordance with common practice, the various described features/elements are not drawn to scale but instead are drawn to best illustrate specific features/elements relevant to the present invention. Also, like reference numerals and designations in the various drawings are used to indicate like elements/parts, where possible.

DESCRIPTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the specification, examples and appended claims are collected here. Unless otherwise defined herein, scientific and technical terminologies employed in the present disclosure shall have the meanings that are commonly understood and used by one of ordinary skill in the art.

Unless otherwise required by context, it will be understood that singular terms shall include plural forms of the same and plural terms shall include the singular. Specifically, as used herein and in the claims, the singular forms "a" and "an" include the plural reference unless the context clearly indicated otherwise. Also, as used herein and in the claims, the terms "at least one" and "one or more" have the same meaning and include one, two, three, or more. Furthermore, the phrases "at least one of A, B, and C", "at least one of A, B, or C" and "at least one of A, B and/or C," as use throughout this specification and the appended claims, are intended to cover A alone, B alone, C alone, A and B together, B and C together, A and C together, as well as A, B, and C together.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques. Ranges can be expressed herein as from one endpoint to another endpoint or between two endpoints. All ranges disclosed herein are inclusive of the endpoints, unless specified otherwise.

This present disclosure pertains generally to molecular constructs, in which each molecular construct comprises a targeting element (T) and an effector element (E), and these molecular constructs are sometimes referred to as "T-E molecules", "T-E pharmaceuticals" or "T-E drugs" in this document.

As used herein, the term "targeting element" refers to the portion of a molecular construct that directly or indirectly binds to a target of interest (e.g., a receptor on a cell surface or a protein in a tissue) thereby facilitates the transportation of the present molecular construct into the interested target. In some example, the targeting element may direct the molecular construct to the proximity of the target cell. In other cases, the targeting element specifically binds to a molecule present on the target cell surface or to a second molecule that specifically binds a molecule present on the cell surface. In some cases, the targeting element may be internalized along with the present molecular construct once it is bound to the interested target, hence is relocated into the cytosol of the target cell. A targeting element may be an antibody or a ligand for a cell surface receptor, or it may be a molecule that binds such antibody or ligand, thereby indirectly targeting the present molecular construct to the target site (e.g., the surface of the cell of choice). The localization of the effector (therapeutic agent) in the diseased site will be enhanced or favored with the present molecular constructs as compared to the therapeutic without a targeting function. The localization is a matter of degree or relative proportion; it is not meant for absolute or total localization of the effector to the diseased site.

According to the present invention, the term "effector element" refers to the portion of a molecular construct that elicits a biological activity (e.g., inducing immune responses, exerting cytotoxic effects and the like) or other functional activity (e.g., recruiting other hapten tagged therapeutic molecules), once the molecular construct is directed to its target site. The "effect" can be therapeutic or diagnostic. The effector elements encompass those that bind to cells and/or extracellular immunoregulatory factors. The effector element comprises agents such as proteins, nucleic acids, lipids, carbohydrates, glycopeptides, drug moieties (both small molecule drug and biologics), compounds, elements, and isotopes, and fragments thereof.

Although the terms, first, second, third, etc., may be used herein to describe various elements, components, regions, and/or sections, these elements (as well as components, regions, and/or sections) are not to be limited by these terms. Also, the use of such ordinal numbers does not imply a sequence or order unless clearly indicated by the context. Rather, these terms are simply used to distinguish one element from another. Thus, a first element, discussed below, could be termed a second element without departing from the teachings of the exemplary embodiments.

Here, the terms "link," "couple," and "conjugates" are used interchangeably to refer to any means of connecting two components either via direct linkage or via indirect linkage between two components.

The term "polypeptide" as used herein refers to a polymer having at least two amino acid residues. Typically, the polypeptide comprises amino acid residues ranging in length from 2 to about 200 residues; preferably, 2 to 50 residues. Where an amino acid sequence is provided herein, L-, D-, or beta amino acid versions of the sequence are also contemplated. Polypeptides also include amino acid polymers in which one or more amino acid residues are an artificial chemical analogue of a corresponding naturally occurring amino acid, as well as to naturally occurring amino acid polymers. In addition, the term applies to amino acids joined by a peptide linkage or by other, "modified linkages," e.g., where the peptide bond is replaced by an α-ester, a β-ester, a thioamide, phosphoramide, carbomate, hydroxylate, and the like.

In certain embodiments, conservative substitutions of the amino acids comprising any of the sequences described herein are contemplated. In various embodiments, one, two, three, four, or five different residues are substituted. The term "conservative substitution" is used to reflect amino acid substitutions that do not substantially alter the activity (e.g., biological or functional activity and/or specificity) of the molecule. Typically, conservative amino acid substitutions involve substitution one amino acid for another amino acid with similar chemical properties (e.g., charge or hydrophobicity). Certain conservative substitutions include "analog substitutions" where a standard amino acid is replaced by a non-standard (e.g., rare, synthetic, etc.) amino acid differing minimally from the parental residue. Amino acid analogs are considered to be derived synthetically from the standard amino acids without sufficient change to the structure of the parent, are isomers, or are metabolite precursors.

In certain embodiments, polypeptides comprising at least 80%, preferably at least 85% or 90%, and more preferably at least 95% or 98% sequence identity with any of the sequences described herein are also contemplated.

"Percentage (%) amino acid sequence identity" with respect to the polypeptide sequences identified herein is defined as the percentage of polypeptide residues in a candidate sequence that are identical with the amino acid residues in the specific polypeptide sequence, after aligning the sequences and introducing gaps, if necessary, to achieve the maximum percent sequence identity, and not considering any conservative substitutions as part of the sequence identity. Alignment for purposes of determining percentage sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, sequence comparison between two polypeptide sequences was carried out by computer program Blastp (protein-protein BLAST) provided online by Nation Center for Biotechnology Information (NCBI). The percentage amino acid sequence identity of a given polypeptide sequence A to a given polypeptide sequence B (which can alternatively be phrased as a given polypeptide sequence A that has a certain % amino acid sequence identity to a given polypeptide sequence B) is calculated by the formula as follows:

$$\frac{X}{Y} \times 100\%$$

where X is the number of amino acid residues scored as identical matches by the sequence alignment program BLAST in that program's alignment of A and B, and where Y is the total number of amino acid residues in A or B, whichever is shorter.

The term "PEGylated amino acid" as used herein refers to a polyethylene glycol (PEG) chain with one amino group and one carboxyl group. Generally, the PEGylated amino acid has the formula of $NH_2$—$(CH_2CH_2O)_n$—COOH. In the present disclosure, the value of n ranges from 1 to 20; preferably, ranging from 2 to 12.

As used herein, the term "terminus" with respect to a polypeptide refers to an amino acid residue at the N- or C-end of the polypeptide. With regard to a polymer, the term "terminus" refers to a constitutional unit of the polymer (e.g., the polyethylene glycol of the present disclosure) that is positioned at the end of the polymeric backbone. In the present specification and claims, the term "free terminus" is used to mean the terminal amino acid residue or constitutional unit is not chemically bound to any other molecular.

The term "antigen" or "Ag" as used herein is defined as a molecule that elicits an immune response. This immune response may involve a secretory, humoral, and/or cellular antigen-specific response. In the present disclosure, the term "antigen" can be any of a protein, a polypeptide (including mutants or biologically active fragments thereof), a polysaccharide, a glycoprotein, a glycolipid, a nucleic acid, or a combination thereof.

In the present specification and claims, the term "antibody" is used in the broadest sense and covers fully assembled antibodies, antibody fragments that bind with antigens, such as antigen-binding fragment (Fab/Fab'), F(ab')2 fragment (having two antigen-binding Fab portions linked together by disulfide bonds), variable fragment (Fv), single chain variable fragment (scFv), bi-specific single-chain variable fragment (bi-scFv), nanobodies, unibodies and diabodies. "Antibody fragments" comprise a portion of an intact antibody, preferably the antigen-binding region or variable region of the intact antibody. Typically, an "antibody" refers to a protein consisting of one or more polypeptides substantially encoded by immunoglobulin genes or fragments of immunoglobulin genes. The well-known immunoglobulin genes include the kappa, lambda, alpha, gamma, delta, epsilon, and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. A typical immunoglobulin (antibody) structural unit is known to comprise a tetramer. Each tetramer is composed of two identical pairs of polypeptide chains, with each pair having one "light" chain (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains, respectively. According to embodiments of the present disclosure, the antibody fragment can be produced by modifying the nature antibody or by de novo synthesis using recombinant DNA methodologies. In certain embodiments of the present disclosure, the antibody and/or antibody fragment can be bispecific, and can be in various configurations. For example, bispecific antibodies may comprise two different antigen binding sites (variable regions). In various embodiments, bispecific antibodies can be produced by hybridoma technique or recombinant DNA technique. In certain embodiments, bispecific antibodies have binding specificities for at least two different epitopes.

The term "specifically binds" as used herein, refers to the ability of an antibody or an antigen-binding fragment thereof, to bind to an antigen with a dissociation constant (Kd) of no more than about $1 \times 10^{-6}$ M, $1 \times 10^{-7}$ M, $1 \times 10^{-8}$ M, $1 \times 10^{-9}$ M, $1 \times 10^{-10}$ M, $1 \times 10^{-11}$ M, $1 \times 10^{-12}$M, and/or to bind to an antigen with an affinity that is at least two-folds greater than its affinity to a nonspecific antigen.

The term "treatment" as used herein includes preventative (e.g., prophylactic), curative or palliative treatment; and "treating" as used herein also includes preventative (e.g., prophylactic), curative or palliative treatment. In particular, the term "treating" as used herein refers to the application or administration of the present molecular construct or a pharmaceutical composition comprising the same to a subject, who has a medical condition a symptom associated with the medical condition, a disease or disorder secondary to the medical condition, or a predisposition toward the medical condition, with the purpose to partially or completely alleviate, ameliorate, relieve, delay onset of, inhibit progression of, reduce severity of, and/or reduce incidence of one or more symptoms or features of said particular disease, disorder, and/or condition. Treatment may be administered to a subject who does not exhibit signs of a disease, disorder, and/or condition, and/or to a subject who exhibits only early signs of a disease, disorder and/or condition, for the purpose of decreasing the risk of developing pathology associated with the disease, disorder and/or condition.

The term "effective amount" as used herein refers to the quantity of the present molecular construct that is sufficient to yield a desired therapeutic response. An effective amount of an agent is not required to cure a disease or condition but will provide a treatment for a disease or condition such that the onset of the disease or condition is delayed, hindered or prevented, or the disease or condition symptoms are ameliorated. The effective amount may be divided into one, two, or more doses in a suitable form to be administered at one, two or more times throughout a designated time period. The specific effective or sufficient amount will vary with such factors as particular condition being treated, the physical condition of the patient (e.g., the patient's body mass, age, or gender), the type of subject being treated, the duration of the treatment, the nature of concurrent therapy (if any), and the specific formulations employed and the structure of the compounds or its derivatives. Effective amount may be expressed, for example, as the total mass of active component (e.g., in grams, milligrams or micrograms) or a ratio of mass of active component to body mass, e.g., as milligrams per kilogram (mg/kg).

The terms "application" and "administration" are used interchangeably herein to mean the application of a molecular construct or a pharmaceutical composition of the present invention to a subject in need of a treatment thereof.

The terms "subject" and "patient" are used interchangeably herein and are intended to mean an animal including the human species that is treatable by the molecular construct, pharmaceutical composition, and/or method of the present invention. The term "subject" or "patient" intended to refer to both the male and female gender unless one gender is specifically indicated. Accordingly, the term "subject" or "patient" comprises any mammal, which may benefit from the treatment method of the present disclosure. Examples of a "subject" or "patient" include, but are not limited to, a human, rat, mouse, guinea pig, monkey, pig, goat, cow, horse, dog, cat, bird and fowl. In an exemplary embodiment, the patient is a human. The term "mammal" refers to all members of the class Mammalia, including humans, primates, domestic and farm animals, such as rabbit, pig, sheep, and cattle; as well as zoo, sports or pet animals; and rodents, such as mouse and rat. The term "non-human mammal" refers to all members of the class Mammalis except human.

The present disclosure is based, at least on the construction of the T-E pharmaceuticals that can be delivered to target cells, target tissues or organs at increased proportions relative to the blood circulation, lymphoid system, and other cells, tissues or organs. When this is achieved, the therapeutic effect of the pharmaceuticals is increased, while the scope and severity of the side effects and toxicity is decreased. It is also possible that a therapeutic effector is administered at a lower dosage in the form of a T-E molecule, than in a form without a targeting component. Therefore, the therapeutic effector can be administered at lower dosages without losing potency, while lowering side effects and toxicity.

Diseases that can Benefit from Better Drug Targeting

Drugs used for many diseases can be improved for better efficacy and safety, if they can be targeted to the disease sites, i.e., if they can be localized or partitioned to the disease sites more favorably than the normal tissues or organs. Certain antibody drugs, which target infectious microorganisms or their toxic products, can be improved, if they are empowered with the ability to recruit immunocytes, which phagocytose and clear the antibody-bound particles. Following are primary examples of diseases, in which drugs can be improved if they can be preferentially distributed to the disease sites or cells or if they can recruit phagocytic immunocytes.

Disease/Condition Associated with Blood Clot

There are two main aspects of pharmaceutical needs in dealing with the pathological problems of blood clotting (or coagulation): one aspect is to prevent or inhibit pathological blood clots to form or to grow in size once a nucleus of clot is formed, and the other aspect is to dissolve already-formed pathological clots timely. In both aspects, there are batteries of pharmaceutical products available clinically. Research aiming at developing still better products is continuing actively and a number of products are in clinical trials.

Patients suffered from various complications (e.g., those resulted from cardiovascular, endocrine, or other bodily regulatory conditions, surgical, the use of medicine, and other factor) have the tendency to develop blood clots. The clots may cause hemorrhagic strokes, head trauma, myocardial infarction, pulmonary embolism, or deep vein thrombosis, which often lead to serious, life threatening clinical conditions.

Coagulation involves a cascade of protease-catalyzed events, which amplify in sequence. Toward the later steps, Factor Xa cleaves prothrombin to thrombin, and thrombin cleaves fibrinogen to fibrin, which in combination with platelets forms the meshwork of a clot. The dissolution of the blood clot involves plasmin, which is generated from plasminogen via one of several of enzymes, including tissue plasminogen activator.

A. The Use of T-E Molecules for Preventing the Formation of a Blood Clot

A large number of indirect inhibitors of Factor Xa have been developed and used. For many decades, the inhibitors are primarily heparin, which is a mixture of naturally occurring polysaccharides of glycosaminoglycan of varying molecular weights from 5 to 30 kDa, low-molecular weight heparin, and heparinoid compounds. Those substances bind to heparin-binding proteins, including anti-thrombin, thus potentiating those substances to inhibit Factor Xa, thereby inhibiting the clot formation. Tissue factor pathway inhibitor (TFPI), a single-chain serum protein of 34,000-40,000 Daltons depending on the degree of proteolysis, can inhibit Factor Xa. However, it is not produced by recombinant DNA technology as a therapeutic.

A number of direct inhibitors of thrombin have also been developed and used clinically. Naturally recovered hirudin from medical leeches and recombinant hirudin, which bind to thrombin, were used for many years before they were discontinued because of the introduction of other better medicines.

More recently, several small molecules that are direct inhibitors of Factor Xa, or thrombin have been developed and approved for clinical uses in preventing coagulation in several clinical indications. In one set of clinical applications, these small molecules are direct inhibitors of Factor Xa, and may be apixaban, edoxaban, or rivaroxaban. In another set of applications, these small molecules are direct inhibitors of thrombin, and may be argatroban or dabigatran. Ximelagatran, a direct thrombin inhibitor, has favorable kinetics and may be administered in very small doses; however, it has been withdrawn from the market due to hepatoxicity problems. It is noted that Ximelagatran is a pro-drug, and the orally taken ximelagatran is converted in the liver to melagatran, which is the active form that binds to and inhibits thrombin. It is very possible that the reduced dosage of melagatran relative to that of ximelagatran and the avoidance of conversion of ximelagatran in the live can avoid the hepatoxicity seen with ximelagatran.

We rationalize that an effective approach to deal with clot formation is to inhibit a nucleus of a clot from growing into a pathological clot. Therefore, if an increased amount of Factor Xa inhibitor or thrombin inhibitor or both are brought to the clot nucleus, the clot will be prevented from growing in size and becoming pathological. We can use IgG or scFv of an anti-fibrin antibody to carry a drug bundle of an inhibitor of Factor Xa or an inhibitor of thrombin or combined bundles of both kinds of inhibitors to the newly formed nucleus of clot. Both the Factor Xa inhibitor molecules (such as, apixaban, edoxaban, and rivaroxaban) and the thrombin inhibitor molecules (such as, argatroban and melagatran) have an $NH_2$ group for conjugation with a linker unit proposed in the present disclosure.

Because the Factor Xa inhibitor and/or thrombin inhibitor are carried to the site of the clot by an anti-fibrin antibody, smaller amounts of the inhibitors than those used without anti-fibrin targeting will be required. Furthermore, because the blood stream flows in the blood vessels, the concentration effects of the carried inhibitors surrounding the clot will be significant only when the nucleus of the clot has grown to a certain size. Therefore, the physiologically required blood coagulation to mend minute internal wounds will not be affected. Thus, the targeting of Factor Xa and thrombin inhibitors by an anti-fibrin antibody to the clot should be therapeutically more effective, while reducing side effects of internal bleeding.

According to embodiments of the present disclosure, T-E molecules in the joint-linker configuration contain scFv specific for fibrin as targeting elements and a Factor Xa inhibitor (apixaban, edoxaban, or rivaroxaban) or thrombin inhibitor (argatroban and melagatran) or both as effector elements.

(B) The Use of T-E Molecules to Speed Up the Dissolution of Blood Clots

To administer proper medications for dissolving pathological clots in a timely, tightly controlled fashion has been a very important pharmaceutical challenge. The development of several forms of recombinant human tissue plasminogen activator (tPA), including alteplase, reteplase, tenecteplase, and lanoteplase, has solved a significant part of the thrombosis problems. However, the use of tPA in many cases either is not sufficient to dissolve the clots or causes serious internal bleeding, or both. The controlled use of dosages and administration schedule of tPA is still an area of active research. The clinical studies comparing the several forms of recombinant tPA are also very active. From the wealth of published literature on tPA and its variants and their medical uses, it is apparent that the various properties of tPA, including the affinity in binding to fibrin, its half-life, the susceptibility to breakdown by liver cells, and the resistance to plasminogen activator inhibitor all play part in the desired properties of the tPA for a particular clinical condition.

The molecular structure of intact tPA is complex, comprising several structural domains with discrete functions or activities, although not all of these domains are required for a thrombolytic product suitable for use in dissolving blood clots. A full-length tPA molecule (alteplase) with 527 amino acid residues contains, (i) a fibronectin finger domain that binds to fibrin, (2) an epidermal growth factor domain that binds to hepatocytes and facilitates tPA's clearance, (3) a Kringle 1 domain that binds to hepatic endothelial cells and facilitates tPA' clearance, (4) a Kringle 2 domain that binds to fibrin and activates the serine protease, and (5) a protease domain that cleaves the plasminogen and is inhibited by plasminogen activator inhibitor type 1 (PAI-1). Alteplase, tenecteplase, and lanoteplase are produced in mammalian cells, CHO cells, and reteplase is produced in bacteria.

Reteplase, which is 355 residues in length, does not contain the fibronectin finger, epidermal growth factor domain, and Kringle 1 domain. Reteplase is produced in bacteria, and therefore it does not contain the posttranslational carbohydrate modification. While reteplase has a lower affinity for fibrin and its protease is not activated to the extent as in alteplase, reteplase has a plasma half-life of 14-18 minutes; in contrast, the half-life period of alteplase only lasts 3-4 minutes in plasma. Reteplase is administered to patients in boli, while alteplase is administered in a bolus followed by an infusion.

Tenecteplase has the entire length of 527 amino acid residues of alteplase, but has mutations at three sites. Threonine at 103 is replaced by asparagine to allow glycosylation modification, and asparagine at 117 is replaced by glutamine to eliminate glycosylation. These mutations inhibit the clearance of the molecule by liver cells. In addition, the four residues at 296-299 (i.e., lysine-histidine-arginine-arginine) are replaced by four alanine residues, thus increasing the resistance to PAI-1 by 80 times. Tenecteplase has a plasma half-life of 18 minutes.

In lanoteplase, the fibronectin finger and the epidermal growth factor domain are deleted and the asparagine at 117 is replaced by glutamine. The plasma half-life of lanoteplase is increased to 45 minutes, which improves administration procedures.

In various clinical trials, the overall therapeutic efficacies of the four forms of tPA are about equal, and each seems to fit better than others do in particular clinical conditions.

In the present invention, it is rationalized that a moderate increase in binding strength to fibrin and a moderate increase of plasma half-life over those exhibited by reteplase will increase the therapeutic properties of reteplase. These molecular constructs will allow more specificity for binding to clots and hence allowing lower doses and fewer side effects. If they cannot fit to all clinical conditions pertaining to dissolving blood clots, they can be applied to some of the conditions. Thus, a preferred embodiment of the present invention for an improved tPA for dissolving blood clots is that 1-3 scFv of an anti-fibrin antibody are employed as targeting elements and 1-2 copies reteplase are employed as effector elements in a joint-linkers configuration. In an alternative construct, reteplase is conjugated to the linker-unit via its C-terminal in order that the N-terminal Kringle 2 domain is flexible in contacting fibrin meshwork in the clot. The C-terminal is extended with a linker, such as (GGGGS)$_2$ (SEQ ID NO: 36) and a cysteine residue. In still another embodiment, an Fc-fusion protein construct linking a tPA or its fragment and scFv specific for fibrin may also be applicable for facilitating the dissolution of pathological clots.

Part I Multi-Arm Linkers for Treating Specific Diseases

I-(i) Peptide Core for Use in Multi-Arm Linker

The first aspect of the present disclosure pertains to a linker unit that comprises, (1) a center core that comprises 2-15 lysine (K) residues, and (2) 2-15 linking arms respectively linked to the K residues of the center core. The present center core is characterized in having or being linked with an azide group, an alkyne group, a tetrazine group, or a strained alkyne group at its N- or C-terminus.

In the preparation of the present linker unit, a PEG chain having a N-hydroxysuccinimidyl (NHS) group at one terminus and a functional group (e.g., an NHS, a maleimide, an azide, an alkyne, a tetrazine, or a strained alkyne group) at the other terminus is linked to the K residue of the center core by forming an amide bond between the NHS group of the PEG chain and the amine group of the K residue. In the present disclosure, the PEG chain linked to the K residue is referred to as a linking arm, which has a functional group at the free-terminus thereof.

According to the embodiments of the present disclosure, the center core is a polypeptide that has 8-120 amino acid residues in length and comprises 2 to 15 lysine (K) residues, in which each K residue and the next K residue are separated by a filler sequence.

According to embodiments of the present disclosure, the filler sequence comprises glycine (G) and serine (S) residues; preferably, the filler sequence consists of 2-15 residues selected from G, S, and a combination thereof. For example, the filler sequence can be,

GS,

GGS,

GSG,

GGGS, (SEQ ID NO: 1)

GSGS, (SEQ ID NO: 2)

GGSG, (SEQ ID NO: 3)

GSGGS, (SEQ ID NO: 4)

SGGSG, (SEQ ID NO: 5)

GGGGS, (SEQ ID NO: 6)

GGSGGS, (SEQ ID NO: 7)

GGSGGSG, (SEQ ID NO: 8)

SGSGGSGS, (SEQ ID NO: 9)

-continued

```
                                         (SEQ ID NO: 10)
GSGGSGSGS, (SEQ ID NO: 11)
SGGSGGSGSG, (SEQ ID NO: 12)
GGSGGSGGSGS, (SEQ ID NO: 13)
SGGSGGSGSGGS, (SEQ ID NO: 14)
GGGGSGGSGGGGS, (SEQ ID NO: 15)
GGGSGSGSGSGGGS,
or (SEQ ID NO: 16)
SGSGGGGSGGSGSG.
```

The filler sequence placed between two lysine residues may be variations of glycine and serine residues in somewhat random sequences and/or lengths. Longer fillers may be used for a polypeptide with fewer lysine residues, and shorter fillers for a polypeptide with more lysine residues. Hydrophilic amino acid residues, such as aspartic acid and histidine, may be inserted into the filler sequences together with glycine and serine. As alternatives for filler sequences made up with glycine and serine residues, filler sequences may also be adopted from flexible, soluble loops in common human serum proteins, such as albumin and immunoglobulins.

Basically, the filler sequences between lysine residues cover peptides with glycine and serine residues. However, they can alternatively be peptides composed of amino acids excluding one with amine group in its side chain. Those amino acids are predominantly, but not necessarily entirely hydrophilic amino acids. The amino acids are not necessarily naturally occurring amino acids.

According to certain preferred embodiments of the present disclosure, the center core comprises 2-15 units of the sequence of $G_{1-5}SK$. Alternatively, the polypeptide comprises the sequence of $(GSK)_{2-15}$; that is, the polypeptide comprises at least two consecutive units of the sequence of GSK. For example, the present center core may comprises the amino acid sequence of the following,

```
                                         (SEQ ID NO: 17)
Ac-CGGSGGSGGSKGSGSK, (SEQ ID NO: 18)
Ac-CGGSGGSGGSKGSGSKGSK,
or (SEQ ID NO: 19)
Ac-CGSKGSKGSKGSKGSKGSKGSKGSKGSK,
``` in which Ac represents the acetyl group.

According to certain embodiments of the present disclosure, the center core is a polypeptide that comprises the sequence of $(X_{aa}-K)_n$, in which $X_{aa}$ is a PEGylated amino acid having 2 to 12 repeats of ethylene glycol (EG) unit, and n is an integral from 2 to 15.

As would be appreciated, the lysine residue of the present center core may be substituted with an amino acid, which side chain contains an amine group. For example, an α-amino acid with $(CH_2-)nNH_2$ side chain, where n=1-3 or 5; an α-amino acid with $(CH(OH)-)nCH_2-NH_2$ side chain, where n=1-5; an α-amino acid with $(CH_2-CH(OH)-)nCH_2-NH_2$ side chain, where n=1-3; an α-amino acid with $(CH_2-CH_2-O-)nCH_2-NH_2$ side chain, where n=1-2. These amino acids are not necessarily naturally occurring amino acids.

As described above, the present center core is characterized in having or being linked with an azide group, an alkyne group, a tetrazine group, or a strained alkyne group at its N- or C-terminus. According to some embodiments of the present disclosure, the present center core comprises, at its N- or C-terminus, an amino acid residue having an azide group or an alkyne group. The amino acid residue having an azide group can be, L-azidohomoalanine (AHA), 4-azido-L-phenylalanine, 4-azido-D-phenylalanine, 3-azido-L-alanine, 3-azido-D-alanine, 4-azido-L-homoalanine, 4-azido-D-homoalanine, 5-azido-L-ornithine, 5-azido-d-ornithine, 6-azido-L-lysine, or 6-azido-D-lysine.

Exemplary amino acid having an alkyne group includes, but is not limited to, L-homopropargylglycine (L-HPG), D-homopropargylglycine (D-HPG), or beta-homopropargylglycine (β-HPG).

It is noted that many of the amino acids containing an azide or alkyne group in their side chains and PEGylated amino acids are available commercially in t-boc (tert-butyloxycarbonyl)- or Fmoc (9-fluorenylmethyloxycarbonyl)-protected forms, which are readily applicable in solid-phase peptide synthesis.

According to some working examples of the present disclosure, the center core may comprise the sequence of,

```
                                         (SEQ ID NO: 21)
Ac-G^{HP}GGSGGSGGSKGSGSK, (SEQ ID NO: 22)
Ac-G^{HP}GGSGGSGGSKGSGSKGSK, (SEQ ID NO: 23)
Ac-A^{AH}GGSGGSGGSKGSGSKGSK, (SEQ ID NO: 24)
Ac-G^{HP}GGSGGSGGSKGSGSKGSGSC, (SEQ ID NO: 25)
Ac-C-Xaa_2-K-Xaa_2-K-Xaa_2-K,
or (SEQ ID NO: 26)
Ac-C-Xaa_6-K-Xaa_6-K-Xaa_6-K-Xaa_6-K-Xaa_6-K,
``` in which Xaa is a PEGylated amino acid having specified repeats of EG unit, Ac represents the acetyl group, $A^{AH}$ represents the AHA residue, and $G^{HP}$ represents the HPG residue.

Alternatively, the present center core is linked with a coupling arm, which has a functional group (e.g., an azide group, an alkyne group, a tetrazine group, or a strained alkyne group) at the free-terminus thereof (that is, the terminus that is not linked to the center core). In these cases, the present center core comprises a cysteine residue at its N- or C-terminus. To prepare a linker unit linked with a coupling arm, a PEG chain having a maleimide group at one terminus and a functional group at the other terminus is linked to the cysteine residue of the center core via thiol-maleimide reaction occurred between the maleimide group of the PEG chain and the thiol group of the cysteine residue. In the present disclosure, the PEG chain linked to the cysteine residue of the center core is referred to as the coupling arm, which has a functional group at the free-terminus thereof.

As would be appreciated, the cysteine residue of the present center core may be substituted with an amino acid, which side chain contains a sulfhydryl group. For example, an α-amino acid with (CH(OH)-)nCH$_2$—SH side chain, where n=1-5; an α-amino acid with (CH$_2$—CH(OH)-)nCH$_2$—SH side chain, where n=1-3; an α-amino acid with (CH$_2$—CH$_2$—O-)nCH$_2$—SH side chain, where n=1-2. The amino acid is not necessarily naturally occurring amino acids. The cysteine residue need not be placed at the N- or C-terminal of the peptide core. For example, the cysteine residue can be placed in the middle of the peptide, so that the lysine residues are distributed on two sides of the cysteine residue.

Preferably, the coupling arm has a tetrazine group or a strained alkyne group (e.g., a cyclooctene or cyclooctyne group) at the free-terminus thereof. These coupling arms have 2-12 EG units. According to the embodiments of the present disclosure, the tetrazine group is 1,2,3,4-tetrazine, 1,2,3,5-tetrazine, 1,2,4,5-tetrazine, or derivatives thereof. The strained alkyne group may be a cyclooctene or a cyclooctyne group. According to the working examples of the present disclosure, the cyclooctene group is a trans-cyclooctene (TCO) group; example of cyclooctyne group includes, but is not limited to, dibenzocyclooctyne (DBCO), difluorinated cyclooctyne (DIFO), bicyclononyne (BCN), and dibenzocyclooctyne (DICO). According to some embodiments of the present disclosure, the tetrazine group is 6-methyl-tetrazine.

The polypeptide may also be synthesized using recombinant technology by expressing designed gene segments in bacterial or mammalian host cells. It is preferable to prepare the polypeptide as recombinant proteins if the core has high numbers of lysine residues with considerable lengths. As the length of a polypeptide increases, the number of errors increases, while the purity and/or the yield of the product decrease, if solid-phase synthesis was adopted. To produce a polypeptide in bacterial or mammalian host cells, a filler sequence ranges from a few amino acid residues to 10-20 residues may be placed between two K residues. Further, since AHA and HPG are not natural amino acids encoded by the genetic codes, the N-terminal or C-terminal residue for those recombinant polypeptides is cysteine. After the recombinant proteins are expressed and purified, the terminal cysteine residue is then reacted with short bifunctional cross-linkers, which have maleimide group at one end, which reacts with SH group of cysteine residue, and alkyne, azide, tetrazine, or strained alkyne at the other end.

The synthesis of a polypeptide using PEGylated amino acids involves fewer steps than that with regular amino acids such as glycine and serine resides. In addition, PEGylated amino acids with varying lengths (i.e., numbers of repeated ethylene glycol units) may be employed, offering flexibility for solubility and spacing between adjacent amino groups of lysine residues. Other than PEGylated amino acids, the center cores may also be constructed to comprise artificial amino acids, such as D-form amino acids, homo-amino acids, N-methyl amino acids, etc. Preferably, the PEGylated amino acids with varying lengths of polyethylene glycol (PEG) are used to construct the center core, because the PEG moieties contained in the amino acid molecules provide conformational flexibility and adequate spacing between conjugating groups, enhance aqueous solubility, and are generally weakly immunogenic. The synthesis of PEGylated amino acid-containing center core is similar to the procedures for the synthesis of regular polypeptides.

Optionally, for stability purpose, the present center core has an acetyl group to block the amino group at its N-terminus.

As could be appreciated, the number of the linking arms linked to the center core is mainly determined by the number of lysine resides comprised in the center core. Since there are at least two lysine residues comprised in the present center core, the present linker unit may comprise a plurality of linking arms.

Reference is now made to FIG. 1A. As illustrated, the linker unit 10A comprises a center core 11a comprising one HPG (G$^{HP}$) residue and four lysine (K) residues respectively separated by filler sequences (denoted by the dots throughout the drawings). The filler sequences between the HPG residue and K residue or between any two K residues may comprise the same or different amino acid sequences. In this example, four linking arms 20a-20d are linked to the lysine residues by forming an amide linkage between the NHS group and the amine group of the lysine residue, respectively. As could be appreciated, certain features discussed above regarding the linker unit 10A or any other following linker units are common to other linker units disclosed herein, and hence some or all of these features are also applicable in the following examples, unless it is contradictory to the context of a specific embodiment. However, for the sake of brevity, these common features may not be explicitly repeated below.

Figure 1B:
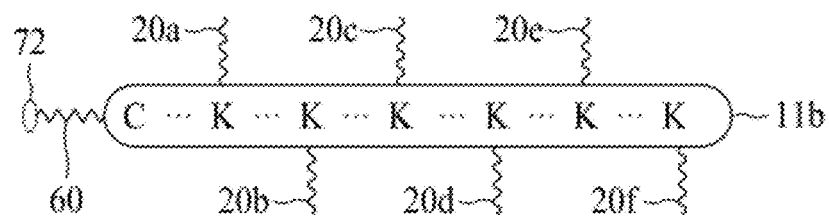

FIG. 1B provides a linker unit 10B according to another embodiment of the present disclosure. The center core 11b comprises one cysteine (C) residue and six lysine (K) residues respectively separated by the filler sequences. In this example, the linker unit 10B comprises six linking arms 20a-20f that are respectively linked to the lysine residues. According to the embodiments of the present disclosure, the linking arm is a PEG chain having 2-20 repeats of EG units.

Unlike the linker unit 10A of FIG. 1A, the linker unit 1B further comprises a coupling arm 60. As discussed above, a PEG chain having a maleimide group at one end and a functional group at the other end is used to form the coupling arm 60. In this way, the coupling arm 60 is linked to the cysteine residue of the center core 11b via thiol-maleimide reaction. In this example, the functional group at the free terminus of the coupling arm 60 is a tetrazine group 72. According to the embodiments of the present disclosure, the coupling arm is a PEG chain having 2-12 repeats of EG units.

When the release of effector elements at the targeted site is required, a cleavable bond can be installed in the linking arm. Such a bond is cleaved by acid/alkaline hydrolysis, reduction/oxidation, or enzymes. One embodiment of a class of cleavable PEG chains that can be used to form the coupling arm is NHS-PEG$_{2-20}$-S-S-maleimide, where S-S is a disulfide bond that can be slowly reduced, while the NHS group is used for conjugating with the amine group of the center core, thereby linking the PEG chain onto the center core. The maleimide group at the free terminus of the linking arm may be substituted by an azide, alkyne, tetrazine, or strained alkyne group.

According to the embodiments of the present disclosure, the linking arm linked to the K residue of the center core has a functional group (i.e., a maleimide, an NHS, an azide, an alkyne, a tetrazine, or a strained alkyne group) at its free terminus. Preferably, when the free terminus of the linking arm is an azide, alkyne, or cyclooctyne group, then the amino acid residue at the N- or C-terminus of the center core is a cysteine residue, and the free terminus of the coupling arm is a tetrazine or cyclooctene group. Alternatively, when the free terminus of the linking arm is a tetrazine group or cyclooctene group, then the amino acid residue at the N- or C-terminus of the center core has an azide or alkyne group, or the amino acid residue at the N- or C-terminus of the center core is a cysteine residue, and the free terminus of the coupling arm is an azide, the alkyne, or the cyclooctyne group Depending on the functional group (i.e., a maleimide, an NHS, an azide, an alkyne, a tetrazine, or a strained alkyne group) present at the free terminus of the linking arm, it is feasible to design a functional element (such as, a targeting element, an effector element, or an element for improving the pharmacokinetic property) with a corresponding functional group, so that the functional element may linked to the free terminus of the linking arm via any of the following chemical reactions, (1) forming an amide bond therebetween: in this case, the linking arm has an NHS group at the free terminus, and the functional element has an amine group;

(2) the thiol-maleimide reaction: in this case, the linking arm has a maleimide group at the free terminus, and the functional element has an thiol group;

(3) the Copper(I)-catalyzed alkyne-azide cycloaddition reaction (CuAAC reaction, or the "click" reaction for short): one of the free terminus of the linking arm and the functional element has an azide group, while the other has an alkyne group; the CuAAC reaction is exemplified in Scheme 1;

(4) the inverse electron demand Diels-Alder (iEDDA) reaction: one of the free terminus of the linking arm and the functional element has a tetrazine group, while the other has a cyclooctene group; the iEDDA reaction is exemplified in Scheme 2; or (5) the strained-promoted azide-alkyne click chemistry (SPAAC) reaction: one of the free terminus of the linking arm and the functional element has an azide group, while the other has an cyclooctyne group; the SPAAC reaction is exemplified in Scheme 3.

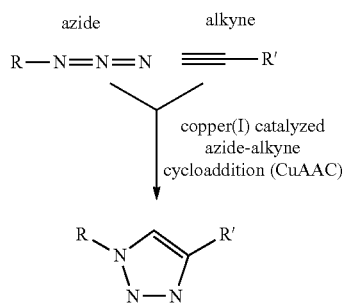

The CuAAC reaction yields 1,5 di-substituted 1,2,3-triazole. The reaction between alkyne and azide is very selective and there are no alkyne and azide groups in natural biomolecules. Furthermore, the reaction is quick and pH-insensitive. It has been suggested that instead of using copper (I), such as cuprous bromide or cuprous iodide, for catalyzing the click reaction, it is better to use a mixture of copper (II) and a reducing agent, such as sodium ascorbate to produce copper (I) in situ in the reaction mixture. Alternatively, the second element can be linked to the N- or C-terminus of the present center core via a copper-free reaction, in which pentamethylcyclopentadienyl ruthenium chloride complex is used as the catalyst to catalyze the azide-alkyne cycloaddition.

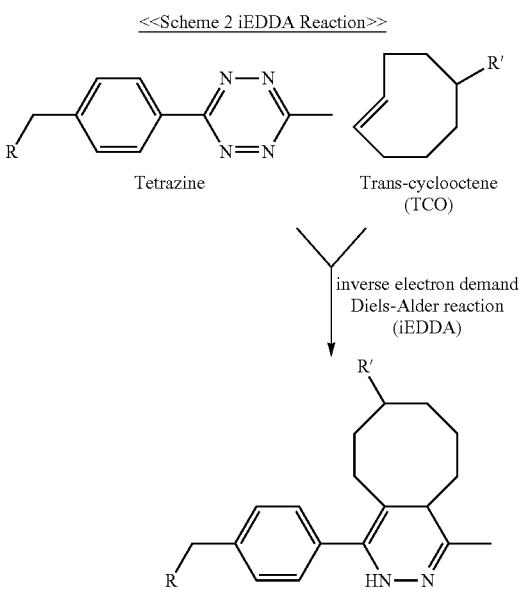

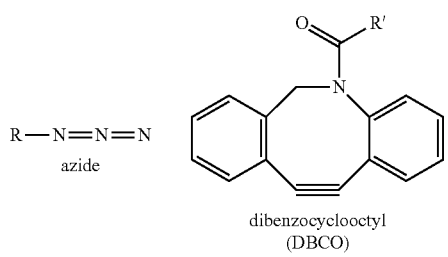

For the sake of illustration, the functional elements linked to the linking arms are referred to as the first elements. As could be appreciated, the number of the first elements carried by the present linker unit depends on the number of K residues of the center core (and thus, the number of the linking arms). Accordingly, one of ordinary skill in the art may adjust the number of the first elements of the linker unit as necessary, for example, to achieve the desired targeting or therapeutic effect.

Figure 1C:
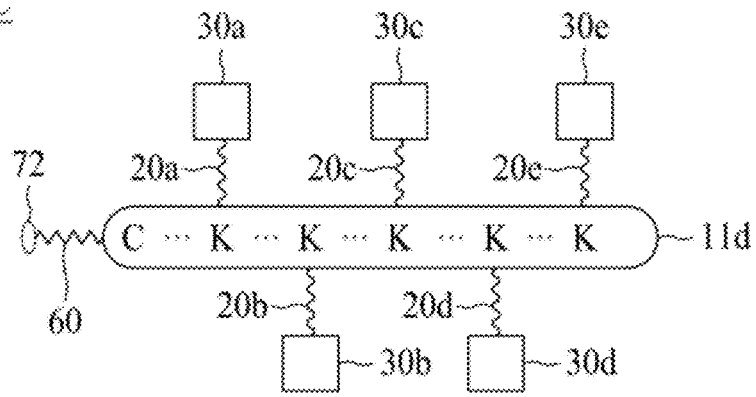

An example of a linker unit 10C having the first elements is illustrated FIG. 1C. Other than the features disused hereafter, FIG. 1C is quite similar to FIG. 1B. First, there are five K residues in the center core 11d, and accordingly, five linking arms 20a-20e are linked thereto, respectively. Second, the linker unit 10C has five first elements 30a-30e linked to each of the linking arms 20a-20e. As disused below, the optional tetrazine group 72 allows for the conjugation with an additional functional element, another molecular construct (see, Part II or Part III below).

In order to increase the intended or desired effect (e.g., the therapeutic effect), the present linker unit may further comprise a second element in addition to the first element. For example, the second element can be either a targeting element or an effector element. In optional embodiments of the present disclosure, the first element is an effector element, while the second element may be another effector element, which works additively or synergistically with or independently of the first element. Still optionally, the first and second elements exhibit different properties; for example, the first element is a targeting element, and the second element is an effector element, and vice versa. Alternatively, the first element is an effector element, and the second element is an element capable of improving the pharmacokinetic property of the linker unit, such as solubility, clearance, half-life, and bioavailability. The choice of a particular first element and/or second element depends on the intended application in which the present linker unit (or multi-arm linker) is to be used. Examples of these functional elements are discussed below in Part I-(iii) of this specification.

Structurally, the second element is linked to the azide, alkyne, tetrazine, or strained alkyne group at the N- or C-terminus of the center core. Specifically, the second element may be optionally conjugated with a short PEG chain (preferably having 2-12 repeats of EG units) and then linked to the N- or C-terminal amino acid residue having an azide group or an alkyne group (e.g., AHA residue or HPG residue). Alternatively, the second element may be optionally conjugated with the short PEG chain and then linked to the coupling arm of the center core.

According to some embodiments of the present disclosure, the center core comprises an amino acid having an azide group (e.g., the AHA residue) at its N- or C-terminus; and accordingly, a second element having an alkyne group is linked to the N- or C-terminus of the center core via the CuAAC reaction. According to other embodiments of the present disclosure, the center core comprises an amino acid having an alkyne group (e.g., the HPG residue) at its N- or C-terminus; and a second element having an azide group is thus capable of being linked to the N- or C-terminus of the center core via the CuAAC reaction.

Figure 1D:
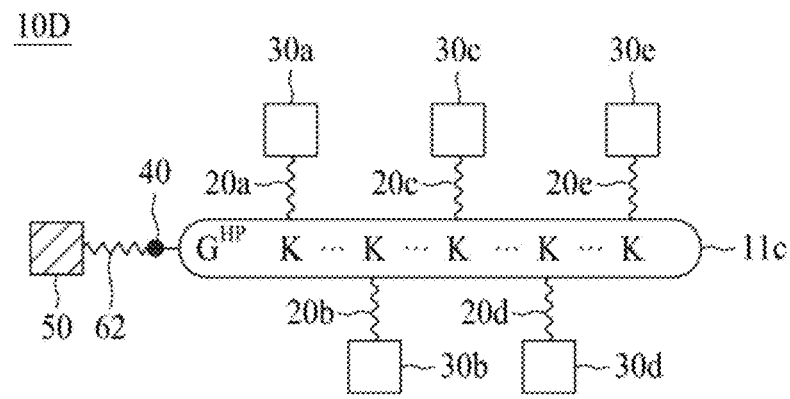

FIG. 1D provides an example of the present linker unit 10D carrying a plurality of first elements and one second element. In this example, the center core 11c comprises one HPG ($G^{HP}$) residue and five lysine (K) residues. Five linking arms 20a-20e are respectively linked to the five K residues of the center core 11c; and five first elements 30a-30e are respectively linked to said five linking arms 20a-20e via the thiol-maleimide reaction. In addition to the first elements, the linker unit 10D further comprises one second element 50 that is linked to one end of a short PEG chain 62. Before being conjugated with the center core 11c, the other end of the short PEG chain 62 has an azide group. In this way, the azide group may react with the HPG residue that having an alkyne group via CuAAC reaction, so that the second element 50 is linked to the center core 11c. The solid dot 40 depicted in FIG. 1D represents the chemical bond resulted from the CuAAC reaction occurred between the HPG residue and the azide group.

Alternatively, the second element is linked to the center core via a coupling arm. According to certain embodiments of the present disclosure, the coupling arm has a tetrazine group, which can be efficiently linked to a second element having a TCO group via the iEDDA reaction. According to other embodiments of the present disclosure, the coupling arm has a TCO group, which is capable of being linked to a second element having a tetrazine group via the iEDDA reaction. In the iEDDA reaction, the strained cyclooctene that possess remarkably decreased activation energy in contrast to terminal alkynes is employed, and thus eliminates the need of an exogenous catalyst.

Figure 1E:
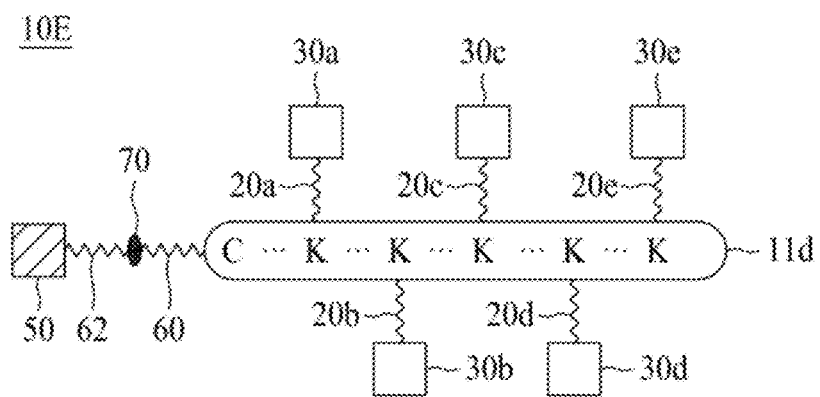

Reference is now made to FIG. 1E, in which the center core 11d of the linker unit 10E comprises a terminal cysteine (C) residue and five lysine (K) residues. As depicted in FIG. 1E, five linking arms 20a-20e are respectively linked to the five K residue of the center core 11d, and then five first elements 30a-30e are respectively linked to the five linking arms 20a-20e via thiol-maleimide reactions. The cysteine residue is linked to the coupling arm 60, which, before being conjugated with the second element, comprises a tetrazine group or a TCO group at its free-terminus. In this example, a second element 50 linked with a short PEG chain 62 having a corresponding TCO or tetrazine group can be linked to the coupling arm 60 via the iEDDA reaction. The ellipse 70 as depicted in FIG. 1E represents the chemical bond resulted from the iEDDA reaction occurred between the coupling arm 60 and the short PEG chain 62.

According to other embodiments of the present disclosure, before the conjugation with a second element, the coupling arm has an azide group. As such, the coupling arm can be linked to the second element having a strained alkyne group (e.g., the DBCO, DIFO, BCN, or DICO group) at the free-terminus of a short PEG chain via SPAAC reaction (see, scheme 3), and vice versa.

Figure 1F:
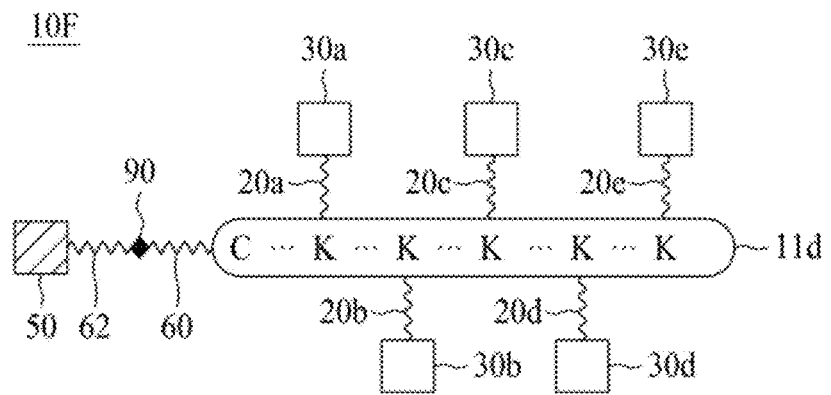

Reference is now made to FIG. 1F, in which the linker unit 10F has a structure similar to the linker unit 10E of FIG. 1E, except that the coupling arm 60 comprises an azide or a strained alkyne group (e.g., the DBCO, DIFO, BCN, or DICO group), instead of the tetrazine or TCO group. Accordingly, the second element 50 linked with a short PEG chain 62 may have a corresponding strained alkyne (e.g., DBCO, DIFO, BCN, or DICO) or azide group, so that it can be linked to the coupling arm 60 via the SPAAC reaction. The diamond 90 as depicted in FIG. 1F represents the chemical bond resulted from the SPAAC reaction occurred between the coupling arm 60 and the short PEG chain 62.

Scheme 4 is an exemplary illustration of the process of preparing the present linker unit.

<<Scheme 4 Preparation of linker unit linked with two different scFvs via linking arm and C-terminal amino acid residue>>

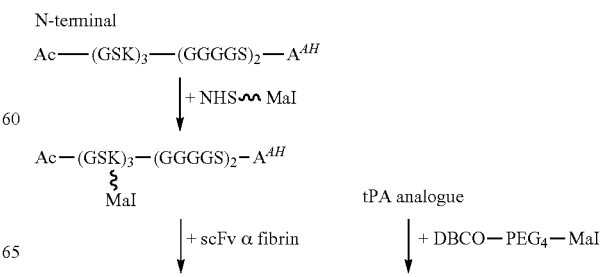

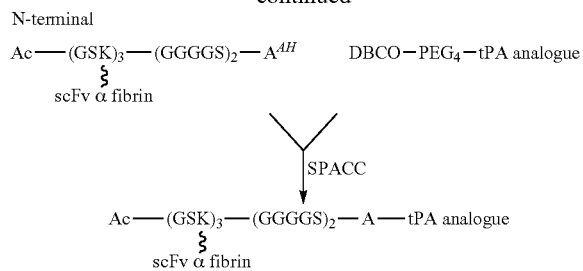

In step 1, the center core having an amino acid sequence of $(GSK)_3(GGGGS)_2A^{AH}$ (SEQ ID NO: 30) is prepared. In step 2, three linking arms are respectively linked to the lysine (K) residues of the center core via forming an amide bond between the NHS group and the amine group; the linking arm linked to the center core has a maleimide (Mal) group at the free-terminus thereof. In step 3, three anti-fibrin scFvs (scFv α fibrin) as the first element are respectively linked to the linking arms via the thiol-maleimide reaction. Meanwhile, in step 4, one tPA analogue as the second element is linked with a short PEG chain that has 4 repeats of EG units and a DBCO group at the free terminus. Finally, in step 5, the second element is linked to the AHA residue of the center core via the SPAAC reaction, and the thus-produced linker unit has the amino acid sequence of $(GSK)_3(GGGGS)_2A$ (SEQ ID NO: 31).

Scheme 5 illustrates another example of the process for preparing the present linker unit.

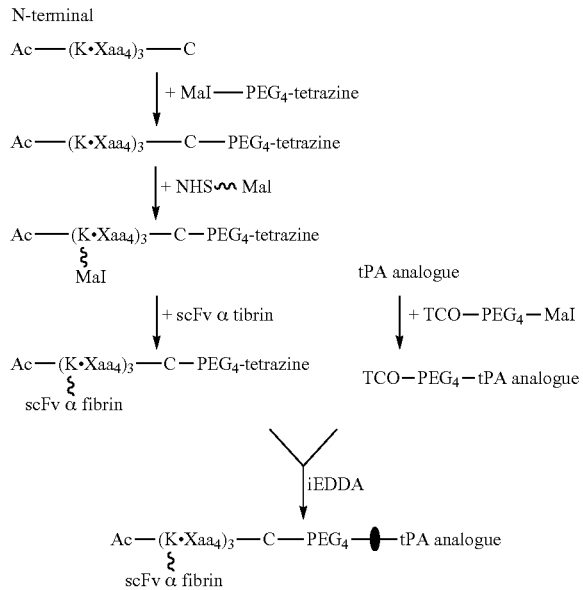

In step 1, the center core ((KXaa$_4$)$_3$C, SEQ ID NO: 32) comprising the amino acid sequence of (K-Xaa$_4$)$_3$ and a cysteine residue at the C-terminus thereof is prepared. In step 2, a PEG chain (as the coupling arm) that has the maleimide (Mal) group at one terminus and a tetrazine group at the other terminus is linked to the cysteine residue via the thiol-maleimide reaction. Then, in step 3, three linking arm are respectively linked to the lysine (K) residues of the center core. Next, three anti-fibrin scFvs (scFv α fibrin) as the first elements are respectively linked to the linking arms via the thiol-maleimide reaction as described in step 4. Meanwhile, in step 5, one tPA analogue as the second element is linked with a short PEG chain that has 3 repeats of EG units and a TCO group at the free terminus. Finally, in step 6, the second element is linked to the coupling arm via the iEDDA reaction.

PEGylation is a process, in which a PEG chain is attached or linked to a molecule (e.g., a drug or a protein). It is known that PEGylation imparts several significant pharmacological advantages over the unmodified form, such as improved solubility, increased stability, extended circulating life, and decreased proteolytic degradation. According to one embodiment of the present disclosure, the second element is a PEG chain, which has a molecular weight of about 20,000 to 50,000 Daltons.

Figure 1G:
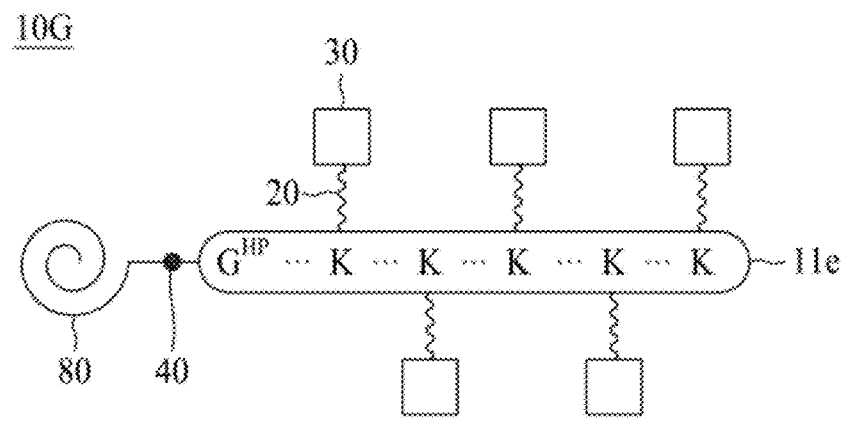

FIG. 1G provides an alternative example of the present linker unit (linker unit 10G), in which five first elements 30 are respectively linked to the lysine residues via the linking arms 20, and the AHA ($A^{AH}$) residue of the center core Ile is linked with a PEG chain 80 via the CuAAC reaction. The solid dot 40 depicted in FIG. 1G represents the chemical bond resulted from the CuAAC reaction occurred between the AHA residue and the PEG chain 80.

Figure 1H:
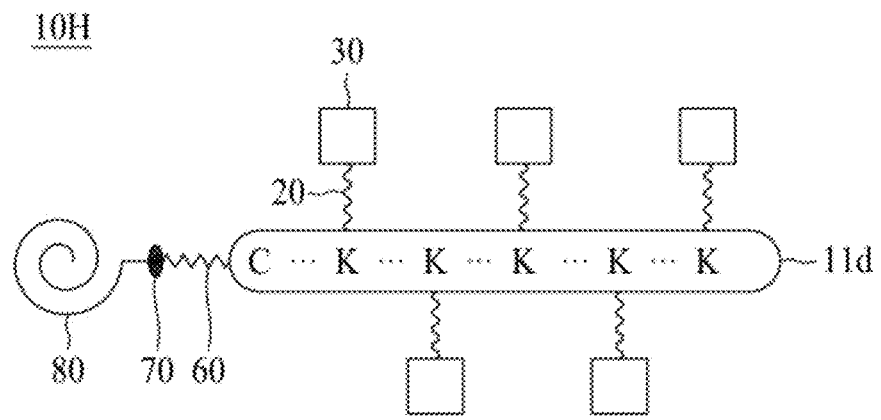

FIG. 1H provides another example of the present disclosure, in which the N-terminus of the center core 11d is a cysteine residue that is linked to a coupling arm 60. A PEG chain 80 can be efficiently linked to the coupling arm 60 via the iEDDA reaction. The ellipse 70 of the linker unit 10H represents the chemical bond resulted from the iEDDA reaction occurred between the coupling arm 60 and the PEG chain 80.

Figure 1I:
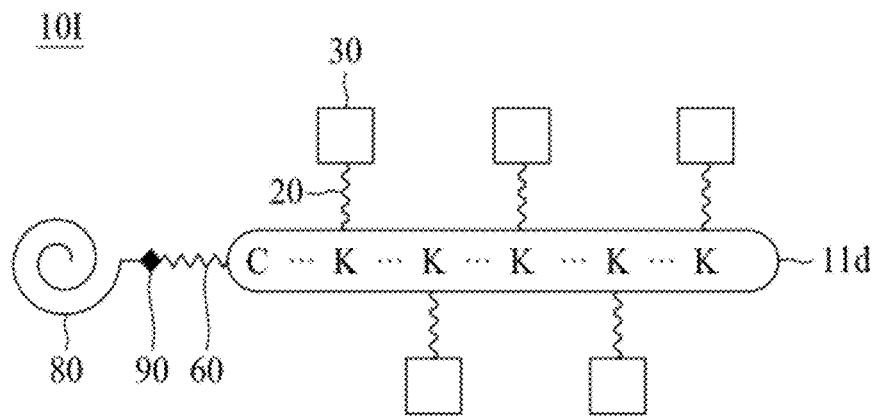

FIG. 1I provides an alternative example of the present linker unit, in which the linker unit 10I has a structure similar to the linker unit 10G of FIG. 1G, except that the PEG chain 80 is linked to the coupling arm 60 via the SPAAC reaction. The diamond 90 depicted in FIG. 1I represents the chemical bond resulted from the SPAAC reaction occurred between the coupling arm 60 and the PEG chain 80.

According to some embodiments of the present disclosure, in addition to the first and second elements, the present linker unit further comprises a third element. In this case, one of the N- and C-terminus of the center core is an amino acid having an azide group or an alkyne group, while the other of the N- and C-terminus of the center core is a cysteine residue. The lysine residues of the center core are respectively linked with the linking arms, each of which has a maleimide group at its free terminus; whereas the cysteine residue of the center core is linked with the coupling arm, which has a tetrazine group or a strained alkyne group at its free terminus. As described above, the first element is therefore linked to the linking arm via the thiol-maleimide reaction, and the second element is linked to the coupling arm via the iEDDA reaction. Further, a third element is linked to the terminal amino acid having an azide group or an alkyne group via the CuAAC reaction or SPAAC reaction.

Figure 1J:
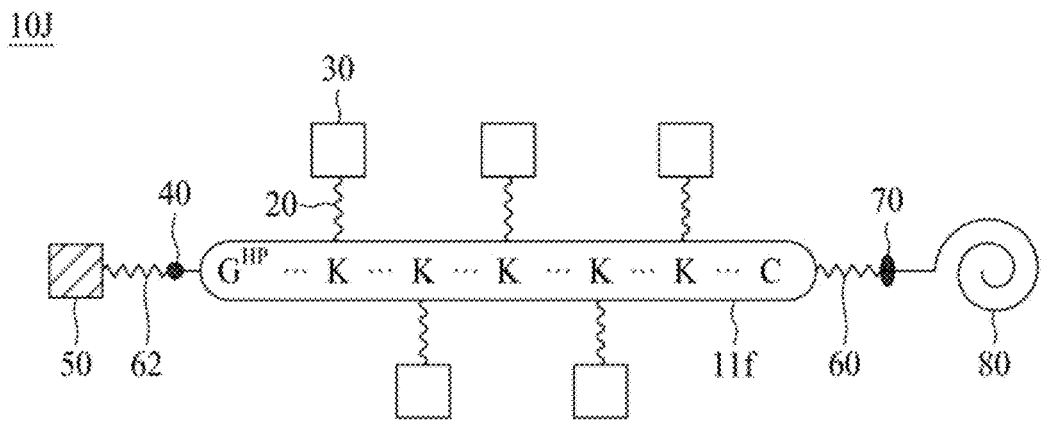

Reference is now made to the linker unit 10J of FIG. 1J, in which the center core 11f has an HPG ($G^{HP}$) residue at the N-terminus thereof and a cysteine residue at the C-terminus thereof. The linking arms 20 and the coupling arm 60 are respectively linked to the lysine (K) residues and the cysteine (C) residue of the center core 11f. Further, five first elements 30 are respectively linked to the five linking arms 20, the second element (i.e., the PEG chain) 80 is linked to the coupling arm 60 via the short PEG chain 62, and the third element 50 is linked to the HPG residue. The solid dot 40 indicated the chemical bond resulted from the CuAAC reaction occurred between the HPG residue and the short PEG chain 62; while the ellipse 70 represents the chemical bond resulted from the iEDDA reaction occurred between the coupling arm 60 and the PEG chain 80.

Figure 1K:
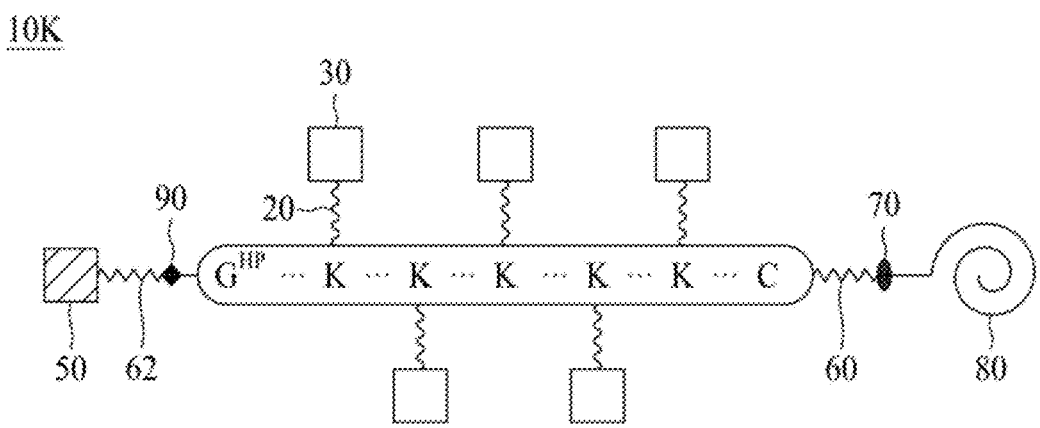

FIG. 1K provides another embodiment of the present disclosure, in which the linker unit 10K has the similar structure with the linker unit 10J of FIG. 1J, except that the short PEG chain 62 is linked with the HPG residue via the SPAAC reaction, instead of the iEDDA reaction. The diamond 90 in FIG. 1K represents the chemical bond resulted from the SPAAC reaction occurred between the short PEG chain 62 and the HPG residue.

In the preferred embodiments of this disclosure, the linking arms have a maleimide group in the free terminus for conjugating with first elements having the sulfhydryl group via the thiol-maleimide reaction. Also, there is one cysteine residue or an amino acid residue with an azide or alkyne group at a terminus of the peptide core for attaching a coupling arm for linking a second element.

It is conceivable for those skilled in the arts that variations may be made. A conjugating group, other than maleimide, such as azide, alkyne, tetrazine, or strained alkyne may be used for the free terminus of the linking arms, for linking with first elements with a CuAAC, iEDDA, or SPAAC reaction. Also the cysteine residue (or an amino acid residue with an azide or alkyne group) of the peptide core needs not to be at the N- or C-terminus. Furthermore, two or more of such residues may be incorporated in the peptide core to attach multiple coupling arms for linking a plural of second elements.

I-(ii) Compound Core for Use in Multi-Arm Linker

In addition to the linker unit described in part I-(i) of the present disclosure, also disclosed herein is another linker unit that employs a compound, instead of the polypeptide, as the center core. Specifically, the compound is benzene-1,3,5-triamine, 2-(aminomethyl)-2-methylpropane-1,3-diamine, tris(2-aminoethyl)amine, benzene-1,2,4,5-tetraamine, 3,3',5,5'-tetraamine-1,1'-biphenyl, tetrakis(2-aminoethyl)methane, tetrakis-(ethylamine)hydrazine, N,N,N',N',-tetrakis(aminoethyl)ethylenediamine, benzene-1,2,3,4,5,6-hexaamine, 1-N,1-N,3-N,3-N,5-N,5-N-hexakis(methylamine)-benzene-1,3,5-triamine, 1-N,1-N,2-N,2-N,4-N,4-N,5-N,5-N,-octakis(methylamine)-benzene-1,2,4,5-triamine, benzene-1,2,3,4,5,6-hexaamine, or N,N-bis[(1-amino-3,3-diaminoethyl)pentyl]-methanediamine. Each of these compounds has 3 or more amine groups in identical or symmetrical configuration. Therefore, when one of the amine groups of a compound is conjugated with a coupling arm, all of the molecules of the compound have the same configuration.

Similar to the mechanism of linkage described in Part I-(i) of the present disclosure, each compound listed above comprises a plurality of amine groups, and thus, a plurality of PEG chains having NHS groups can be linked to the compound via forming an amine linkage between the amine group and the NHS group; the thus-linked PEG chain is designated as linking arm, which has a functional group (e.g., an NHS, a maleimide, an azide, an alkyne, a tetrazine, a cyclooctene, or a cyclooctyne group) at the free-terminus thereof. Meanwhile, at least one of the amine groups of the compound core is linked to another PEG chain, which has an NHS group at one end, and a functional group (e.g., an azide, alkyne, tetrazine, cyclooctene, or cyclooctyne group) at the other end; the thus-linked PEG chain is designated as coupling arm, which has a functional group at the free-terminus thereof.

Accordingly, a first element can be linked to the linking arm via (1) forming an amide bond therebetween, (2) the thiol-maleimide reaction, (3) the CuAAC reaction, (4) the iEDDA reaction, or (5) SPAAC reaction. Meanwhile, the second element can be linked to the coupling arm via the CuAAC, iEDDA, or SPAAC reaction.

According to some embodiments of the present disclosure, the linking arm is a PEG chain having 2-20 repeats of EG units; and the coupling arm is a PEG chain having 2-12 repeats of EG unit.

Schemes 6 and 7 respectively depict the linkages between the center compound core and the linking arm, as well as the coupling arm. In schemes 6 and 7, "NHS" represents the NHS ester, "Mal" represents the maleimide group, "azide" represents the azide group, and "alkyne" represents the alkyne group.

<<Scheme 6 Linkage of linking and coupling arms respectively having maleimide group and azide group to center core>>

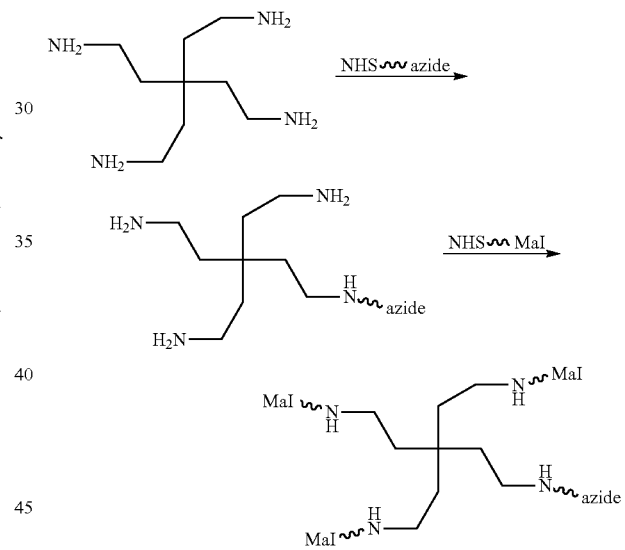

<<Scheme 7 Linkage of linking and coupling arms respectively having maleimide group and alkyne group to center core>>

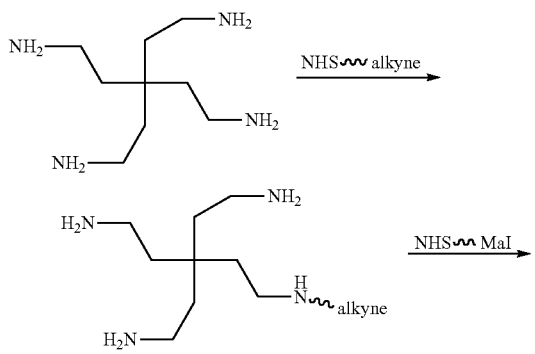

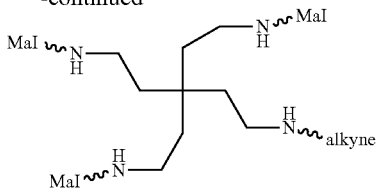

The requirement of having multiple NH$_2$ groups exist in a symmetrical and identical orientation in the compound serving as the center core is for the following reason: when one of the NH$_2$ group is used for connecting a bifunctional linker arm with N-hydroxysuccinimidyl (NHS) ester group and alkyne, azide, tetrazine, or strained alkyne group, the product, namely, a core with a coupling arm having alkyne, azide, tetrazine or strained alkyne, is homogeneous and may be purified. Such a product can then be used to produce multi-arm linker units with all other NH$_2$ groups connected to linking arms with maleimide or other coupling groups at the other ends. If a compound with multiple NH$_2$ groups in non-symmetrical orientations, the product with one bifunctional linking arm/coupling arms is not homogeneous.

Some of those symmetrical compounds can further be modified to provide center cores with more linking arms/coupling arms. For example, tetrakis(2-aminoethyl)methane, which can be synthesized from common compounds or obtained commercially, may be used as a core for constructing linker units with four linking arms/coupling arms. Tetrakis(2-aminoethyl)methane can react with bis(sulfosuccinimidyl)suberate to yield a condensed product of two tetrakis (2-aminoethyl)methane molecules, which can be used as a core for constructing linker units having six linking arms/coupling arms. The linker units, respectively having three linking arms/coupling arms, four linking arms/coupling arms and six linking arms/coupling arms, can fulfill most of the need for constructing targeting/effector molecules with joint-linker configuration.

As would be appreciated, the numbers of the linking arm and/or the coupling arm and the element linked thereto may vary with the number of amine groups comprised in the center core. In some preferred embodiments, the numbers of the linking arm/coupling arm and the corresponding linking element linked thereto ranges from about 1-7.

Figure 2:
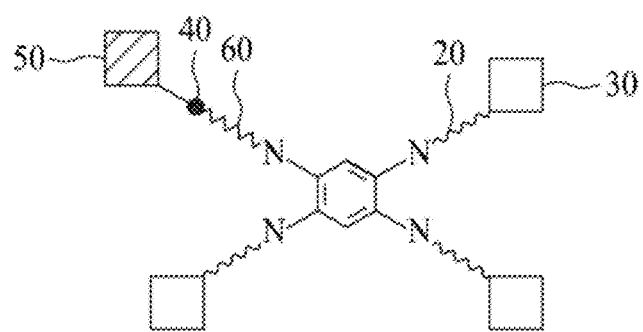
FIG. 2 is a schematic diagram illustrating a linker unit having a compound core.

Reference is now made to FIG. 2, in which benzene-1,2,4,5-tetraamine having 4 amine groups is depicted. Three of the amine groups are respectively linked to the linking arms 20, and one of the amine group is linked to the coupling arm 60, which has an azide group at its free-terminus. Three first elements 30 are then respectively linked to the three linking arms 20 via the thiol-maleimide reactions, and one second element 50 is linked to the coupling arm 60 via the CuAAC reaction. The solid dot 40 as depicted in FIG. 2 represents the chemical bond resulted from the CuAAC reaction occurred between the coupling arm 60 and the second element 50.

I-(iii) Functional Elements Suitable for Use in Multi-Arm Linker

In the case where the linker unit (or multi-arm linker) comprises only the first element but not the second and/or third element(s), the first element is an effector element that may elicit a therapeutic effect in a subject. On the other hand, when the present linker unit comprises elements in addition to first element(s), then at least one of the elements is an effector element, while the other may be another effector element, a targeting element, or an element capable of enhancing one or more pharmacokinetic properties of the linker unit (e.g., solubility, clearance, half-life, and bioavailability). For example, the linker unit may have two different kinds of effector element, one effector element and one targeting element or one pharmacokinetic property-enhancing element, two different kinds of targeting elements and one kind of effector element, two different kinds of effector elements and one kind of targeting element, or one kind of targeting element, one kind of effector element and one element capable of improving the pharmacokinetic property of the linker unit.

According to some embodiments of the present disclosure, the present linker unit is useful in preventing the formation of blood clot. In these embodiments, the present linker unit comprises the first element of an scFv specific for fibrin as the targeting element, and the second element of Factor Xa inhibitors or thrombin inhibitors as the effector element. Preferably, the inhibitor of Factor Xa is selected from the group consisting of, apixaban, edoxaban, and rivaroxaban; and the inhibitor of thrombin is argatroban or melagatran.

Linker units for use in the treatment of thrombosis may comprise the first element of an scFv specific for fibrin as the targeting element, and the second element of tissue plasminogen activators (such as alteplase, reteplase, tenecteplase and lanoteplase) used as the effector element.

I-(iv) Use of Multi-Arm Linker

The present disclosure also pertains to method for treating various diseases using the suitable linker unit. Generally, the method comprises the step of administering to a subject in need of such treatment an effective amount of the linker unit according to embodiments of the present disclosure.

Compared with previously known therapeutic constructs, the present linker unit discussed in Part I is advantageous in two points:

(1) The number of the functional elements may be adjusted in accordance with the needs and/or applications. The present linker unit may comprise two elements (i.e., the first and second elements) or three elements (i.e., the first, second, and third elements) in accordance with the requirements of the application (e.g., the disease being treated, the route of administration of the present linker unit, and the binding avidity and/or affinity of the antibody carried by the present linker unit). For example, when the present linker unit is directly delivered into the tissue/organ (e.g., the treatment of eye), one element acting as the effector element may be enough, thus would eliminate the need of a second element acting as the targeting element. However, when the present linker unit is delivered peripherally (e.g., oral, enteral, nasal, topical, transmucosal, intramuscular, intravenous, or intraperitoneal injection), it may be necessary for the present linker unit to simultaneously comprise a targeting element that specifically targets the present linker unit to the lesion site; and an effector element that exhibits a therapeutic effect on the lesion site. For the purpose of increasing the targeting or treatment efficacy or increasing the stability of the present linker unit, a third element (e.g., a second targeting element, a second effector element, or a PEG chain) may be further included in the present linker unit.

(2) The first element is provided in the form of a bundle. As described above, the number of the first element may vary with the number of lysine residue comprised in the center core. If the number of lysine residue in the center core ranges from 2 to 15, then at least two first elements may be comprised in each linker unit. Thus, instead of providing one single molecule (e.g., cytotoxic drug and antibody) as traditional therapeutic construct or method may render, the present linker unit is capable of providing more functional elements (either as targeting elements or as effector elements) at one time, thereby greatly improves the therapeutic effect.

In certain therapeutic applications, it is desirable to have a single copy of a targeting or effector element. For example, a single copy of a targeting element can be used to avoid unwanted effects due to overly tight binding. This consideration is relevant, when the scFv has a relatively high affinity for the targeted antigen and when the targeted antigen is a cell surface antigen on normal cells, which are not targeted diseased cells. As an example, in using scFv specific for CD3 or CD16a to recruit T cells or NK cells to kill targeted cells, such as thyroid gland cells in patients with Grave's disease, a single copy of the scFv specific for CD3 or CD16a is desirable, so that unwanted effects due to cross-linking of the CD3 or CD16a may be avoided. Similarly, in using scFv specific for CD32 or CD16b to recruit phagocytic neutrophils and macrophages to clear antibody-bound viral or bacterial particles or their products, a single copy of scFv may be desirable. Also, in using scFv specific for transferrin receptor to carry effector drug molecules to the BBB for treating CNS diseases, a single copy of scFv specific for transferrin receptor is desirable. In still another example, it is desirable to have only one copy of long-chain PEG for enhancing pharmacokinetic properties. Two or more long PEG chains may cause tangling and affect the binding properties of the targeting or effector elements.

Part II Joint-Linker Molecular Constructs for Treating Specific Diseases

Another aspect of the present disclosure pertains to a molecular construct comprising at least two linker units, in which one linker unit carries one or more targeting element, whereas another other linker unit carries one or more effector elements or pharmacokinetic property-enhancing elements. In the present disclosure, molecular constructs with both the targeting and effector moieties (whether a therapeutic or pharmacokinetic one) are referred to as joint-linker molecular constructs. According to various embodiments of the present disclosure, each of the linker unit comprised in such joint-linker molecular constructs may be either a peptide core-based or a compound core-based multi-arm linkers discussed above in Part I of the present disclosure. According to certain embodiments of the present disclosure, at least one of the linker units of the present molecular construct comprises the polypeptide core. Preferably, at least two linker units of the present molecular construct comprise the polypeptide cores. More preferably, all the linker units of present molecular construct respectively comprise the polypeptide cores.

II-(i) Structure of Joint-Linker Molecular Construct

According to some embodiments of the present disclosure, the molecular construct comprises two linker units, and the linker units are coupled to each other via either the CuAAC reaction (using copper or pentamethylcyclopentadienyl ruthenium chloride complex as catalyst), the SPAAC reaction, or the iEDDA reaction. In the embodiments, one of the linker units is linked with a plurality of first elements, which act as the targeting elements, and the other of the linker units is linked with a plurality of second elements, which act as the effector elements.

According to other embodiments of the present disclosure, the molecular construct comprises three linker units, in which the first and second linker units are coupled to each other via the iEDDA reaction, and then, the third linker unit is coupled to the first or second linker unit via the CuAAC reaction. Alternatively, the first and second linker units are coupled to each other via the iEDDA reaction, and the third linker unit is coupled to the first or second linker unit via the SPAAC reaction. In the embodiments, the first, second, and third linker units respectively carry a plurality of first, second, and third elements, in which the first, second, and third elements are different. According to one embodiment, two of the three elements (i.e., the first, second, and third elements) are targeting elements, and one of the three elements is an effector element. According to another embodiment, two of the three elements are effector elements, and one of the three elements is a targeting element. According to still another embodiment, one of the three elements is a targeting element, another of the three elements is an effector element, and the other of the three elements is an element capable of improving the pharmacokinetic property of the molecular construct, such as solubility, clearance, half-life, and bioavailability.

Figure 3A:
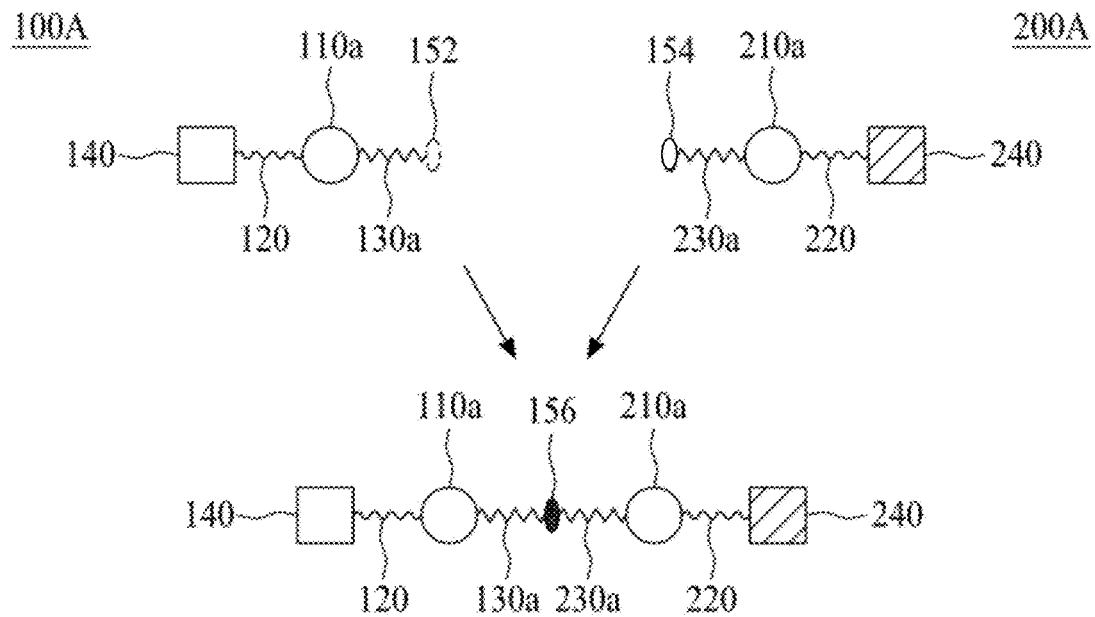
FIG. 3A to FIG. 3D are schematic diagrams illustrating T-E molecular constructs according to some embodiments of the present disclosure.

Reference is first made to FIGS. 3A-3D, which respectively depicts the linkage between the two linker units. FIG. 3A depicts a molecular construct comprising two linker units (100A, 200A), which are coupled to each other via the iEDDA reaction. The first linker unit 100A comprises a first center core 110a, a linking arm 120 (as the first linking arm), and a coupling arm 130a (as the first coupling arm), in which the linking and coupling arms are respectively linked to the first center core 110a at one ends. Similarly, the second linker unit 200A comprises a second center core 210a, a linking arm 220 (as the second linking arm), and a coupling arm 230a (as the second coupling arm), in which the linking and coupling arms are respectively linked to the second center core 210a at one ends. One of the coupling arms 130a, 230a has a tetrazine group at its free terminus, while the other of the coupling arms 130a, and 230a has a TCO group. Specifically, if the coupling arm 130a has a tetrazine group 152 at its free terminus (i.e., the terminus not connected to the first center core 110a), then the coupling arm 230a would have a TCO group 154 at its free terminus (i.e., the terminus not connected to the second center core 210a), and vice versa. Accordingly, the two linker units (100A, 200A) are coupled to each other via the iEDDA reaction occurred between the respective free ends of the coupling arms 130a, 230a. The ellipse 156 as depicted in FIG. 3A represents the chemical bond resulted from the iEDDA reaction occurred between the coupling arms 130a, 230a.

In the depicted embodiment, each of the linking arms 120, 220 has a maleimide group at its free terminus. Accordingly, a first targeting element 140 and a first effector element 240, each has a thiol group are respectively linked to the linking arms 120, 220 via the thiol-maleimide reaction.

According to one embodiment, both the first and second center cores 110a, 210a depicted in FIG. 3A are polypeptide cores. According to another embodiment, both the first and second center cores 110a, 210a depicted in FIG. 3A are compound cores. According to still another embodiment, one of the first and second center cores 110a, 210a depicted in FIG. 3A is a polypeptide core, while the other of the first and second center cores 110a, 210a depicted in FIG. 3A is a compound core.

Figure 3B:
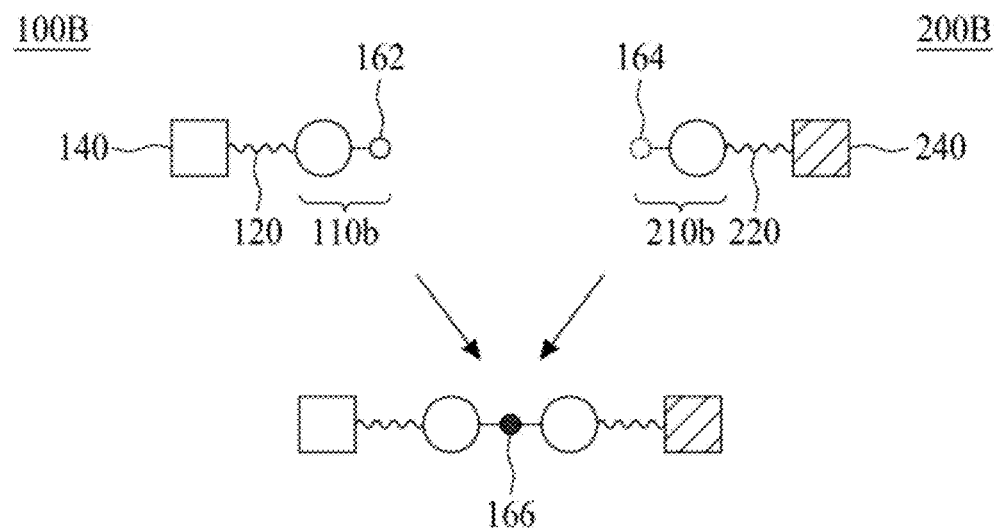

FIG. 3B provides an alternative embodiment of the present disclosure, in which both the first and second center cores 110b, 210b are polypeptide cores, and are respectively linked to a first targeting element 140 and a first effector element 240 via the linking arms 120, 220. The unique feature in this embodiment is that, one of the center cores 110b, 210b comprises an amino acid residue having an azide group (e.g., the AHA residue) at it N- or C-terminus, while the other of the center cores 110b, 210b comprises an amino acid residue having an alkyne group (e.g., the HPG residue) at it N- or C-terminus, such configuration allows the center cores 110a, 210a to be directly linked to each other, that is, without connecting through any coupling arms as that depicted in FIG. 3A. Specifically, if the center core 110b comprises the amino acid residue having the azide group 162 at its N- or C-terminus, then the center core 210b would comprises the amino acid residue having the alkyne group 164 at its N- or C-terminus, and vice versa. Accordingly, the linker units 100B, 200B can couple together directly via the CuAAC reaction occurred between the N- or C-terminal amino acid residues of the center cores 110b, 210b. The solid dot 166 as depicted in FIG. 3B represents the chemical bond formed between the N- or C-terminal amino acid residues.

Figure 3C:
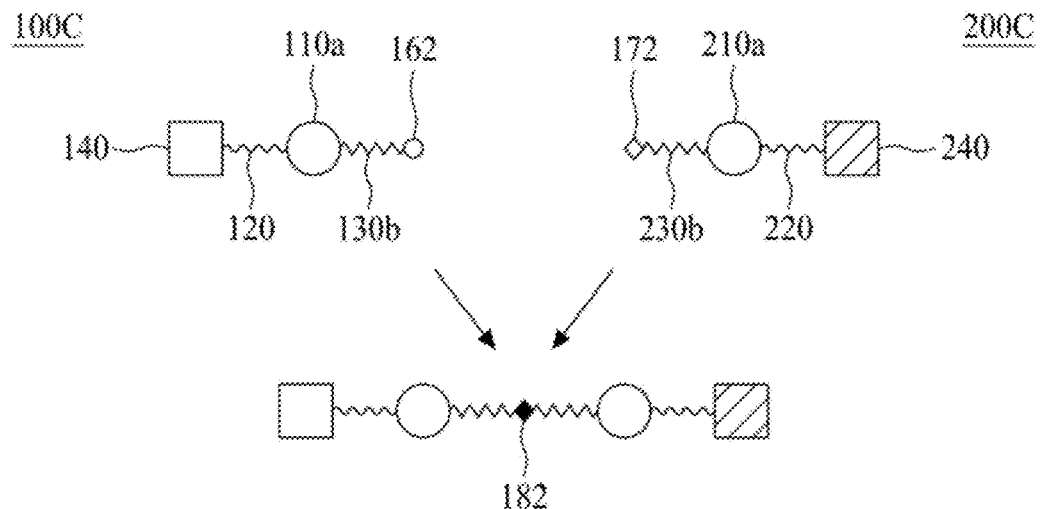

FIG. 3C is another embodiment of the present disclosure. The linker units 100C, 200C have the similar structures as the linker units 100A, 200A, except that the coupling arms 130b, 230b respectively have an azide group 162 and a DBCO group 172, instead of the azide group 152 and the alkyne group 154 as depicted in the linker units 100A, 200A of FIG. 3A. Specifically, the center core 110a is linked with a coupling arm 130b (as the first coupling arm) having an azide group 162 at its free-terminus; and the center core 210a is linked with a coupling arm 230b (as the second coupling arm) having a DBCO group 172 at its free-terminus. The linker units 100C, 200C are then coupled via the SPAAC reaction occurred between the coupling arms 130b, 230b; and forming the chemical bond 182, depicted as a diamond.

In one embodiment, both the first and second center cores 110a, 210a depicted in FIG. 3C are polypeptide cores. In another embodiment, both the first and second center cores 110a, 210a depicted in FIG. 3C are compound cores. In still another embodiment, one of the first and second center cores 110a, 210a depicted in FIG. 3C is a polypeptide core, while the other of the first and second center cores 110a, 210a depicted in FIG. 3C is a compound core.

Figure 3D:
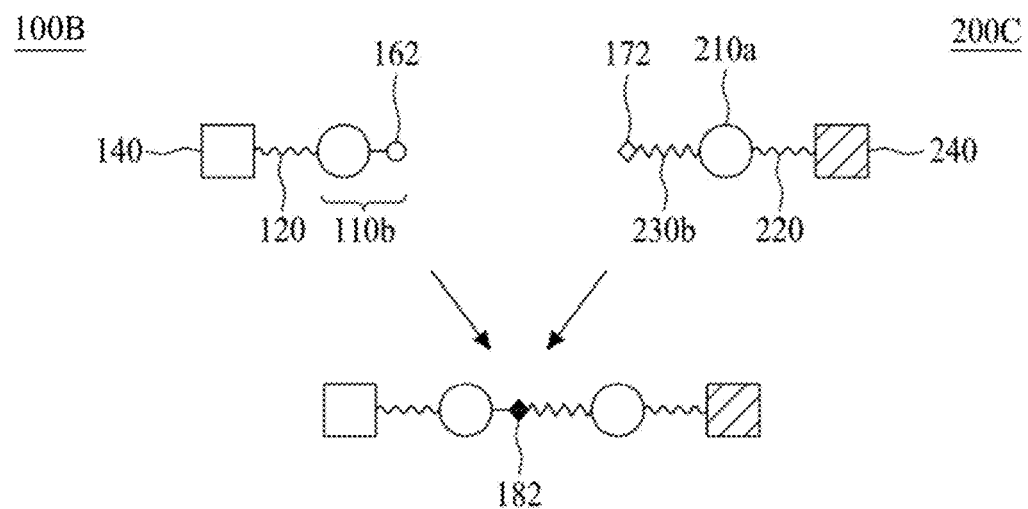

As would be appreciated, two linker units can be coupled to each other via the CuAAC reaction occurred between the center core and the coupling arm. Reference is now made to FIG. 3D, in which the center core 110b comprises a N- or C-terminal amino acid residue that has an azide group 162 (e.g., the AHA residue), and the center core 210a is linked with a coupling arm 230b having a TCO group 172 at its free-terminus. Accordingly, the linker units 100B and 200C can be coupled via the SPAAC reaction occurred between the center core 110b and the coupling arm 230b; and forming the chemical bond 182.

According to one embodiment, the linker units 100B, 200C depicted in FIG. 3D respectively comprise polypeptide cores. According to another embodiment, the center core 100B depicted in FIG. 3D is a polypeptide core, while the center core 200C depicted in FIG. 3D is a compound core.

Alternatively, the linker unit 200B that comprises a N- or C-terminal amino acid residue having an alkyne group 160b (e.g., the HPG residue), and the linker unit 100C comprising the coupling arm 130b with an azide group 160a at its free-terminus can be coupled together via the azide-alkyne cycloaddition occurred between the center core 210b and the coupling arm 130b.

Compared with other therapeutic construct, the present molecular construct is advantageous in at least the three following aspects:

(1) the linker unit comprising a specified number and/or type of targeting/effector element can be prepared independently, then proceed to be coupled together via the CuAAC reaction, the iEDDA reaction, or the SPAAC reaction;

(2) the number and kind of the targeting and/or effector elements may vary in accordance with the requirements of application (e.g., the disease being treating, and the binding avidity and/or affinity of the targeting and/or effector element). The combination of the targeting and effector elements may be adjusted according to specific needs and/or applications. Each of the present targeting and effector elements may vary with such factors like particular condition being treated, the physical condition of the patient, and/or the type of disease being treated. The clinical practitioner may combine the most suitable targeting element and the most suitable effector element so as to achieve the best therapeutic effect. According to embodiments of the present disclosure, the targeting element may be a growth factor, a peptide hormone, a cytokine, or an antibody fragment; and the effector element may be an immunomodulant, a chelator complexed with a radioactive nuclide, a cytotoxic drug, a cytokine, a soluble receptor, or an antibody; and (3) compared with other coupling reactions, the CuAAC reaction, the iEDDA reaction, or the SPAAC reaction is more efficient in terms of coupling any two linker units.

Figure 4:
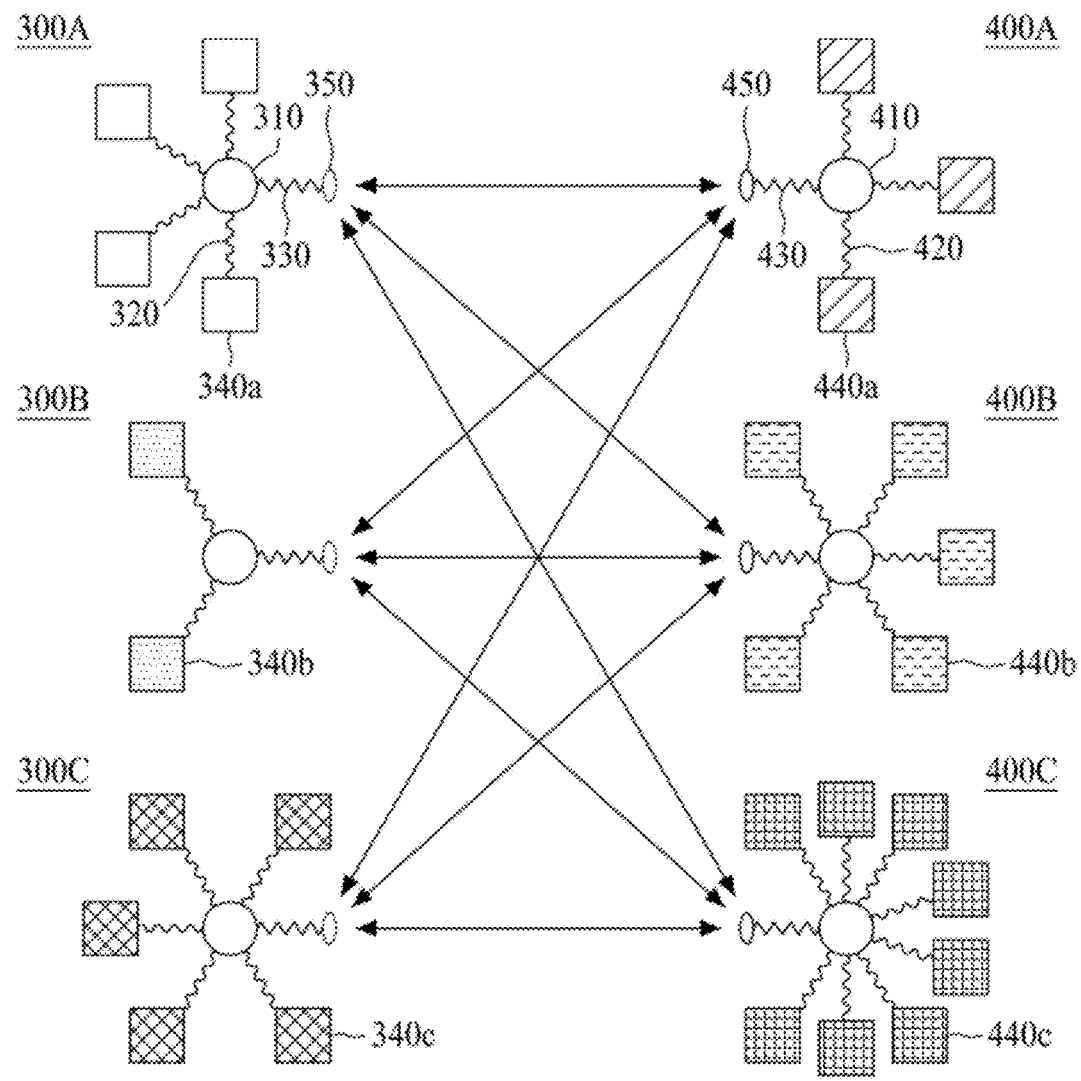
FIG. 4 is a schematic diagram that illustrates libraries for constructing molecular constructs according to some embodiments of the present disclosure.

Reference is now made to FIG. 4, in which six libraries are illustrated, and are prepared independently. In this embodiment, Libraries 1-6 respectively comprise a plurality of linker units 300A, 300B, 300C, 400A, 400B, and 400C that are linked with functional elements. Each linker units 300A, 300B, and 300C are similar in structures; in which each of the linker units 300A, 300B, and 300C comprises one center core 310, one coupling arm 330 linked thereto and has a tetrazine group 350 at its free terminus, and a specified number of the linking arm 320. For instance, Linker unit 300A comprises four linking arms 320, and accordingly, four targeting elements 340a can be respectively linked to the four linking arms 320. Similarly, two targeting elements 340b and five targeting elements 340c can be respectively linked to the linker units 300B and 300C. The targeting elements 340a, 340b, and 340c can be the same or different. As to the linker units 400A, 400B, and 400C, each of these linker units comprises one center core 410, one coupling arm 430 linked thereto and has a strained alkyne group 450 at its free terminus, and a specified number of the linking arm 420. As depicted, three effector elements 440a, five effector elements 440b, and eight effector elements 440c can be respectively linked to the linker units 400A, 400B, and 400C. The effector elements 440a, 440b, and 440c can be the same or different. The Libraries 1-6 may be prepared independently. One skilled artisan may select the first linker unit from Libraries 1, 2 and 3, and the second linker unit from Libraries 4, 5, and 6, then proceed to couple the first and second linker units via the iEDDA reaction occurred between the tetrazine group 350 and the strained alkyne group 450 so as to produce the molecular construct with the specified number of targeting and effector elements.

Figure 5A:
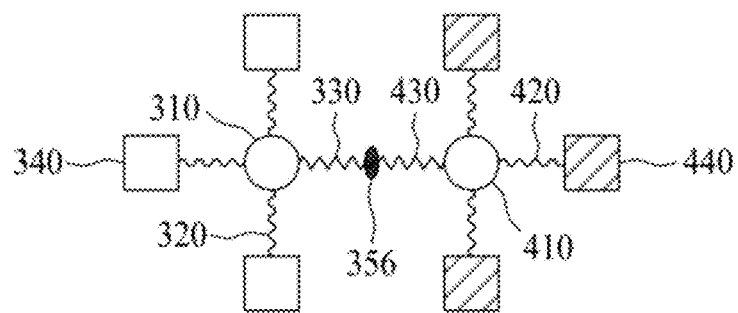
FIG. 5A and FIG. 5B are schematic diagrams that illustrate molecular constructs according to some embodiments of the present disclosure.

Based on the library concept, the present molecular construct can be produced with different configurations depending on the libraries selected. FIG. 5A provides an example of the present molecular construct, in which each of the first and second center cores (310, 410) is linked with three linking arms (320, 420) and one coupling arm (330, 340). Three of the first targeting elements 340 are respectively linked to the linking arms 320; and three of the first effector elements 440 are respectively linked to the linking arms 420. The two linker units are coupled to each other via the iEDDA reaction occurred between two coupling arms 330, 430, and forming the chemical bond 356. By this configuration, equal numbers of multiple targeting and/or effector elements may be carried in one molecular construct.

Figure 5B:
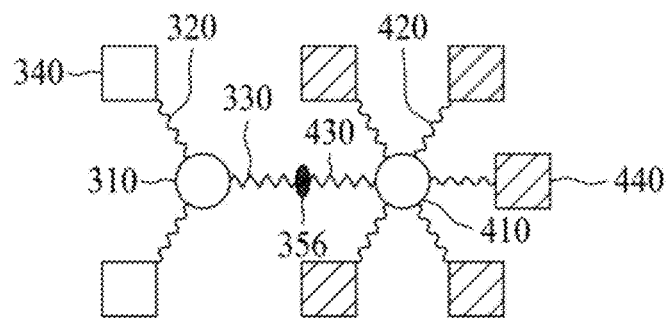

FIG. 5B provides another example of the present molecular construct, in which the first and second center cores respectively contain different numbers of amine groups (e.g., lysine residues), and accordingly, the molecular construct contains non-equal numbers of targeting and effector elements. In the depicted example, the first center core 310 is linked to one coupling arm 330, and two linking arms 320. The second center core 410 is linked to one coupling arm 430, and five linking arms 420. Accordingly, two targeting elements 340 are respectively linked to the linking arms 320; and five effector elements 440 are respectively linked to the linking arms 420. The ellipse 356 in FIG. 5B represents the linkage between two coupling arms 330, 430.

In optional embodiments, the present molecular construct may further comprise a relatively long PEG chain connected to either the first or second center core, so that the present molecular construct may be segregated further away from the reticuloendothelial system and attains a longer half-life after being administered to a subject. In the case where a protein is modified by a PEG chain so as to improve its pharmacokinetic properties and/or to decrease immunogenicity, PEG up to 20,000-50,000 Daltons in length, is preferred. Accordingly, in one preferred embodiment of the present invention, linking arms of relatively shorter lengths are used to connect the targeting and effector elements, while a PEG chain of 20,000 to 50,000 Daltons is connected to any of the linker units with the purpose of increasing in vivo half-life of the present molecular construct.

In some embodiments, multiple scFv fragments are used as the targeting and/or effector elements to construct the present molecular construct. The targeting element/effector element pharmaceuticals based on molecular constructs comprising scFv fragments should have longer in vivo half-lives than individual antibody fragments. For some clinical applications, much extended half-lives of the pharmaceuticals are desired, so as to eliminate the need of frequent administration of the drugs in these cases, PEG chains that are 20,000 to 50,000 Daltons by weight, may be used as the linking arms to link the scFv fragments that serve as targeting or effector elements. PEGs of these lengths have been used to modify a large number of therapeutic proteins to increase their half-lives.

Figure 6:
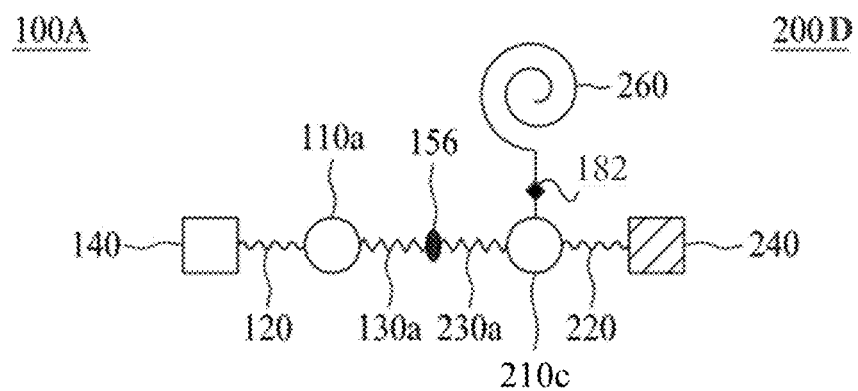
FIG. 6 is a schematic diagram that illustrates a molecular construct according to some embodiments of the present disclosure.

According to some embodiments of the present disclosure, the linker unit may comprise two linking arms respectively linked to the different functional elements. Reference is now made to FIG. 6, in which the molecular construct comprises two linker units 100A and 200D. The first and second functional elements 140, 240 (one serves as the targeting element, and the other serves as the effector element) are respectively linked to the first center core 110a and the second center core 210c via the linking arms 120, 220; and the two center cores 110a, 210c are coupled to each other via the iEDDA reaction occurred between the coupling arms 130a, 230a, in which the ellipse 156 represents the chemical bond forming therebetween. In addition to the functional element 240, the second center core 210c is further linked to a PEG chain 260. Specifically, the second center core 210c comprises an AHA residue, which can be reacted with and linked to the PEG chain 260 having a stained alkyne group via the SPAAC reaction, in which the diamond 182 represents the chemical bond forming from the SPAAC reaction. Depending on the intended and desired use, the third element can be a second targeting element, a second effector element, or an element capable of improving the pharmaceutical property of the molecular construct.

According to one embodiment of the present disclosure, the PEG chain 260 has a molecular weight about 20,000 to 50,000 Daltons.

Based on the concept, a linker unit may comprise a plurality of linking arms, which can be linked to a plurality of functional elements. For example, a linker unit may comprise 5-12 linking arms, which can be linked to 5-12 functional elements. This is especially useful when the functional elements are small molecules, such as cytotoxic drugs or toll-like receptor agonists. The linker unit carrying multiple molecules of a cytotoxic drug is herein referred to as a drug bundle.

Further, the polypeptide cores can be employed to prepare the molecular construct comprising three linker units. Accordingly, another aspect of the present disclosure is directed to a molecular construct comprising three linker units. Among the three linker units, two of them may be connected to each other via the iEDDA reaction, while the third linker unit is connected to any of the two linker units by the SPAAC reaction or CuAAC reaction. The rationale for constructing a multi-linker unit (e.g., three linker units) is that two different sets of targeting elements or two different sets of effector elements can be incorporated therein.

Figure 7A:
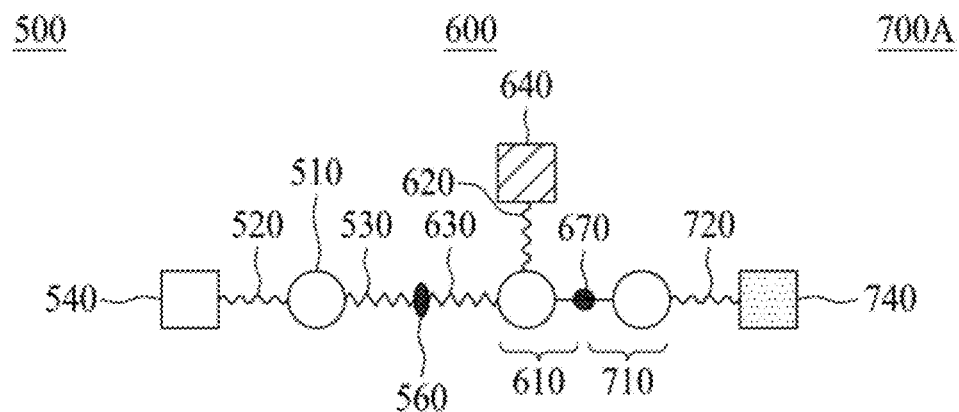
FIG. 7A and FIG. 7B are schematic diagrams illustrating molecular constructs according to various embodiments of the present disclosure.

Reference is now made to FIG. 7, in which the molecular construct comprises three linker units (500, 600, 700A). The linker units 500, 600, 700A respectively comprise a center core (510, 610, 710), and an linking arm (520, 620, 720) with a functional element (540, 640, 740) linked thereto. The linker unit 600 is characterized in comprising a cysteine residue at one of its N- or C-terminus that is linked with a coupling arm 630; and an amino acid residue having an azide or alkyne group at the other of its N- or C-terminus. One of the coupling arms 530, 630 has a tetrazine group at its free terminus, and the other of the coupling arms 530, 630 has a strained alkyne group at its free terminus. Accordingly, the linker units 500, 600 can be coupled to each other via the iEDDA reaction occurred between the coupling arms 530, 630 as the linkage manner described in FIG. 3A. As to the linkage of the linker unit 300, when the N- or C-terminal amino acid residue of the center core 610 has an azide group (e.g., the AHA residue), the center core 710 comprises an amino acid having an alkyne group (e.g., the HPG residue) at its N- or C-terminus; or, when the N- or C-terminal amino acid residue of the center core 610 has an alkyne group (e.g., the HPG residue), then the center core 710 comprises an amino acid having an azide group (e.g., the AHA residue) at its N- or C-terminus. Thus, as the linkage manner described in FIG. 3B, the linker units 600, 700A can be directly coupled to each other via the CuAAC reaction occurred between the N- or C-terminal amino acid residues of the center cores 610, 710 without the presence of the coupling arms. The ellipse 560 and the solid dot 670 in FIG. 7 respectively represent the chemical bonds resulted from the iEDDA reaction and the CuAAC reaction.

Figure 7B:
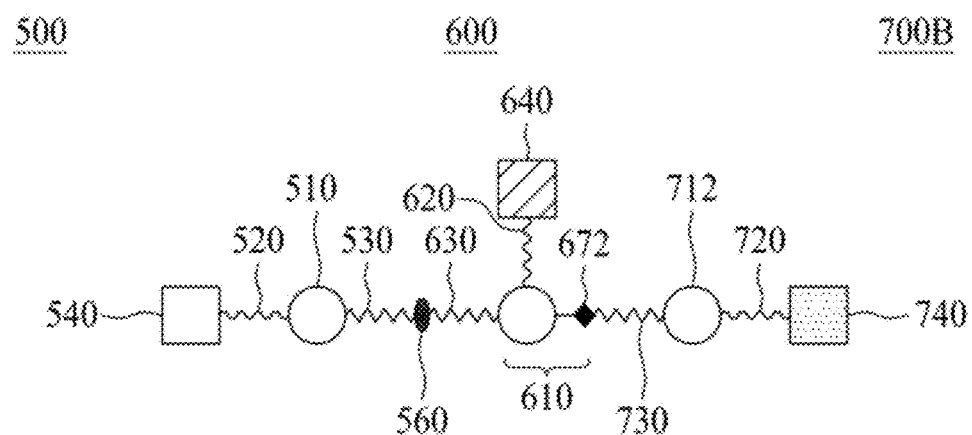

Alternatively, two of the three linker units may be connected to each other via the iEDDA reaction, while the third linker unit is connected to any of the two linker units by the SPAAC reaction. Reference is now made to FIG. 7B, in which the linker units 500, 600 are coupled together via the iEDDA reaction as described in FIG. 7A, whereas the linker unit 700B is linked to the linker unit 600 via the SPAAC reaction occurred between the center core 610 and the coupling arm 730. The diamond 672 in FIG. 7B represents the chemical bond resulted from the SPAAC reaction.

As would be appreciated, each number of the functional elements 540, 640, 740 respectively linked to the linker units 100, 200, 300 are different depending on the intended use. With the library concept depicted in FIG. 4, the linker units respectively carrying different numbers and/or types of functional elements can be prepared separately as different libraries, and one skilled artisan may select and combine the desired linker units from the libraries in accordance with the various applications.

Basically, the coupling arm of the present molecular construct described in above aspects and/or embodiments of the present disclosure that has an azide, alkyne, tetrazine, or strained alkyne group at the terminus is designed as a PEG chain having 2-12 repeats of EG units. The linking arm is designed as a PEG chain having 2-20 repeats of EG units.

Adopting a polypeptide as the center core provides versatility in the present molecular construct, in which multiple copies or types of targeting/effector elements may be present in one construct, accordingly, enhanced specificity of drug delivery and potency in the intended target sites are achieved. A large number of configurations can be adopted by employing the molecular construct comprising multiple linker units. A few examples are: a first linker unit carrying three scFvs targeting elements, and a second linker unit carrying 5 cytotoxic drugs; a first linker unit carrying three scFvs targeting elements, and a second linker unit carrying three scFvs effector elements; a first linker unit carrying two scFvs of the first set targeting elements, a second linker unit carrying two scFvs of the second set targeting elements, and a third linker unit carrying 5 cytotoxic drugs; a first linker unit carrying 2 bi-scFv targeting elements, and a second linker unit carrying two scFvs effector elements; or a first linker unit carrying three scFvs targeting elements, a second linker unit carrying two scFvs effector elements plus a linking arm attached with a long PEG of 20,000-50,000 Daltons for the purpose of increasing pharmacokinetic properties.

In some embodiments of this invention, a bi-functional PEG acting as a linking arm is used to link the antigen-binding fragments of antibodies, which serve as targeting or effector elements, to the amine groups located in the polypeptide core. Each PEG may have NHS group at one end and maleimide group at the other end. The NHS group may couple with amine group in the polypeptide core, while the maleimide group may couple with sulfhydryl group of a cysteine residue of an scFv, bi-scFv, or Fab fragment of an antibody. The scFv and bi-scFv are engineered to have a polypeptide linker with terminal cysteine residue at the C-terminal. Fab may be derived from a whole IgG by pepsin cleavage, and the free sulfhydryl groups are derived from the inter-chain disulfide bond by a mild reduction reaction.

Schemes 8-12 provide several working example respectively depicting the coupling and preparation of specified linker units.

Scheme 8 is a schematic diagram depicting the preparation of the present molecular construct in accordance with one embodiment of the present disclosure, in which NHS represents NHS ester, Mal represents maleimide group, $A^{AH}$ represents L-azidohomoalanine (AHA) residue, AAH represents homopropargylglycine (HPG) residue, Ac represents acetyl group, and scFv represent single-chain variable fragment.

<<Scheme 8 Coupling of linker units via C-terminal amino acid residues>>

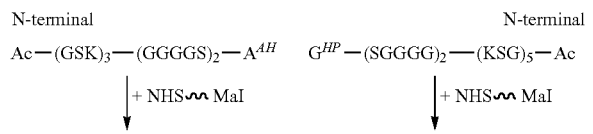

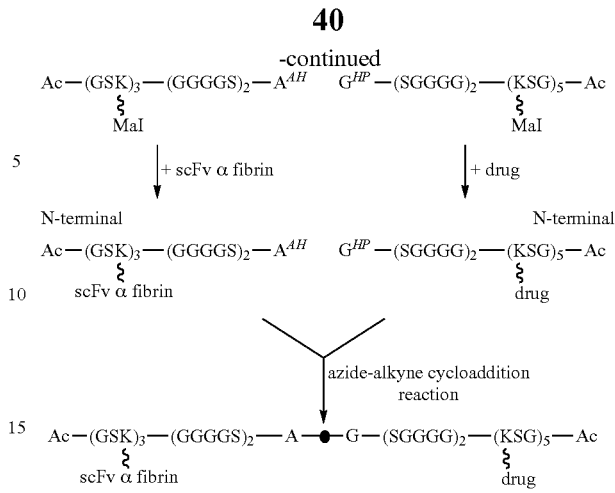

In step 1, the first center core having the amino acid sequence of $(GSK)_3(GGGGS)_2A^{AH}$ (SEQ ID NO: 30); and the second center core having the amino acid sequence of $G^{HP}(SGGGG)_2(KSG)_5$ (SEQ ID NO: 33), are respectively prepared. For the purpose of stabilizing the polypeptide, the N-terminuses of the first and second center cores are respectively modified with an acetyl group. In step 2, the linking arms are respectively linked to the lysine residues in the first and second center cores via forming an amide linkage there between; the linked arm linked to the center core has a maleimide group at the free-terminus. In step 3, the first targeting element (such as an scFv specific for fibrin) having a thiol group (e.g., a cysteine residue) is linked to the linking arm linked with the first center core via the thiol-maleimide reaction; similarly, the effector element (i.e., the drug, such as a Factor Xa inhibitor or thrombin inhibitor) having a thiol group is linked to the linking arm linked with the second center core via the thiol-maleimide reaction. In step 4, the two linker units are coupled via a CuAAC reaction occurred between the AHA and HPG residues, in which the first linker unit having the amino acid sequence of $(GSK)_3(GGGGS)_2A$ (SEQ ID NO: 31), and the second linker unit having the amino acid sequence of $G(SGGGG)_2(KSG)_5$ (SEQ ID NO: 34).

Optionally, the targeting/effector element can be linked to the center core in an alternative method. Scheme 9 is a scheme illustrating the coupling of the effector element with the polypeptide core, in which the linking arm is first linked to the center core having the amino acid sequence of $A^{AH}(SGGGG)_2(KSG)_5$ (SEQ ID NO: 35), and then the effector element (i.e., the drug) is linked to the linking arm via the thiol-maleimide reaction.

<<Scheme 9 Method of coupling of effector element with polypeptide core through linking to linking arms>>

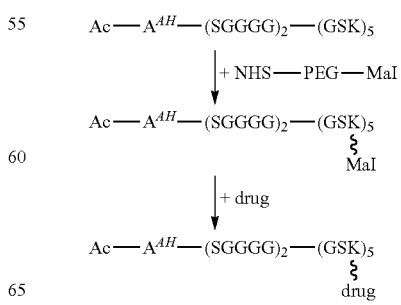

In the alternative method of scheme 10, the effector element (i.e., the drug) is coupled to the linking arm so as to produce a linking arm-effector conjugate (i.e., PEG-drug); next, the linking arm-effector conjugate is linked to the center core having the amino acid sequence of $A^{AH}$ (SGGGG)$_2$(KSG)$_5$ (SEQ ID NO: 35) via forming an amide linkage between the lysine residues and the NHS esters.

<<Scheme 10 Alternative method of coupling of effector element with polypeptide core by first conjugating with PEG chain and then linking to amino groups of lysine residues>>

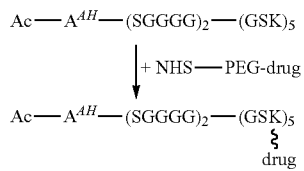

Alternatively, the linking arms for the joint-linker configuration may also be used to link bispecific scFv, which act as targeting elements or effector elements. These configurations will increase the specificity of targeting and/or the potency of the effector mechanisms.

Scheme 11 provides an example of preparing the present molecular construct, which comprises two linker units; both linker units have the amino acid sequence of (KXaa$_4$)$_3$C (SEQ ID NO: 32). In step 1, two coupling arms are respectively linked to the C residues of the linker units, in which one of the coupling arms has a maleimide (Mal) group at one terminus and a tetrazine group at the other terminus, while the other coupling arm has a Mal group at one terminus and a TCO group at the other terminus. In step 2, the linking arms are respectively linked to the lysine (K) residues via forming the amide bond between the linking arm and the K residue. Then, in step 3, three anti-fibrin scFvs (scFv α fibrin) and three tPA analogues are respectively linked to the linking arms of the linker units via the thiol-maleimide reaction. Finally, in step 4, the two linker unit are coupled to each other via the iEDDA reaction occurred between the tetrazine and TCO group.

When the targeting and effector elements are all scFv, and linking arms of 600 Daltons (12 EG units) are used, a molecular construct with a total of six scFvs has a molecular weight of about 170,000 Daltons. A molecular construct with seven scFvs has a molecular weight of about 200,000 Daltons, and a molecular construct with eight scFvs has a molecular weight of about 230,000 Daltons. Most of the molecular constructs of this invention have molecular weights smaller than 200,000 Daltons, and a few molecular constructs have molecular weights in 200,000-250,000 Daltons.

<<Scheme 11 Preparation of molecular construct via iEDDA reaction occurred between coupling arms>>

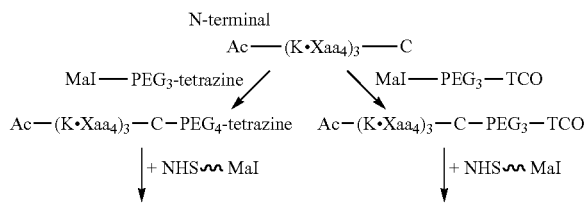

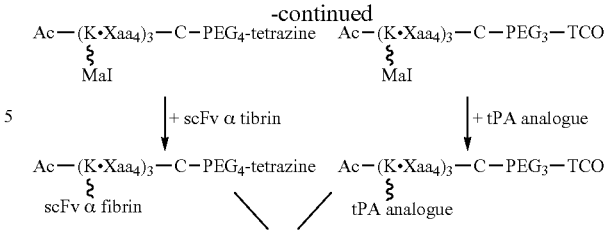

When four different sets of scFv are to be carried in one molecular construct, it is preferable to have one linker unit carrying a joined single-chain, bi-specific scFv (bi-scFv), such as scFv1-scFv2, and the other two linker units each carrying one scFv (i.e., scFv3 and scFv4 respectively). There are two ways to construct bi-specific scFv1-scFv2. In the "tandem" configuration, $V_L1$-$V_H1$-$V_L2$-$V_H2$ or $V_H1$-$V_L1$-$V_H2$-$V_L2$ is arranged; in the "diabody" configuration, $V_L2$-$V_L1$-$V_H1$-$V_H2$ or $V_H2$-$V_H1$-$V_L1$-$V_L2$ is arranged. Proper linkers with GGGGS (SEQ ID NO: 6) repeats or other sequences are placed between the immunoglobulin domains.

In our experience, a peptide or a PEG linker, which contain maleimide and azide groups may become polymerized upon long-term storage, due to the automatic coupling reaction between the maleimide and azide groups. Therefore, it is preferable that each linker unit is prepared freshly and independently, and processed to connecting the targeting or effector elements onto the linker units, and the coupling of the linker units through click reaction without delay. An alternative preferred embodiment is that the targeting elements and effector elements are both conjugated to linker units with alkyne groups, and the alkyne group in one of the linker units is then converted to azide with a short homobifunctional linker with azide at both ends. The linker units, one with alkyne and the other with azide, are then coupled via a click reaction.

The preferred linking arms for this invention are PEG. The length of the linking arms is important for several considerations. It should be long enough to allow flexibility of the linked scFv or other types of functional elements to reach targeted antigenic sites on targeted cell surface without steric constraints; yet not long enough to cause intra-molecular and inter-molecular tangling of the linking arms and their linked scFv fragments or functional elements, or to unnecessarily increase the size of the whole molecular construct for hindering tissue penetration. Linking arms that are too long may also fail to pull antigen molecules to form compacted clusters, if such clusters are required to initiate signal-transducing process for apoptosis or other cellular effects. The optimal length of linking arms for different types of combinations of targeted antigens and their binding agents may be determined by any skilled artisan in the related field without undue experimentation. A linking arm of NHS-(PEG)$_{12}$-Maleimide (approximately 500 Daltons) is preferred in a number of molecular construct of this invention. A fully stretched (PEG)$_{12}$ has a length of 40-50 Å.

Applicable linking arms and coupling arms are not limited by PEG chains. Peptides comprising glycine, serine and other amino acid hydrophilic residues, and polysaccharides, and other biocompatible linear polymers, which are modified to contain NHS and maleimide groups, can be used.

For certain therapeutic applications, it is desirable that the effector elements in the molecular constructs of this disclosure be released from the linking arms, so that they can get into cells in the targeted site, including cells bound by the targeting elements or surrounding cells, to cause pharmacological effects. In those cases, a cleavable bond is engineered in the linking arm. Cleavable bonds, which are susceptible for cleavage by hydrolysis, acid exposure, reduction, and enzymes, have been developed. For example, peptide segments susceptible to matrix metalloproteinases, which are present in inflammatory tissues, have been used in constructing therapeutic constructs. One embodiment of the present invention is to use PEG linkers with S-S bond adjacent to the maleimide group NHS-PEG$_{2-12}$-S-S-maleimide, wherein S-S is a disulfide bond, which can be slowly reduced.

According to some embodiments of the present disclosure, the targeting element described in above-mentioned embodiments is selected from the group consisting of a growth factor, a peptide hormone, a cytokine, and an antibody fragment; and the effector element is an immunomodulant, a chelator complexed with a radioactive nuclide, a cytotoxic drug, a cytokine, a soluble receptor, or an antibody.

In the embodiments, the antibody is in the form of an antigen-binding fragment (Fab), a variable fragment (Fv), a single-chain variable fragment (scFv), a single domain antibody (sdAb), or a bi-specific single-chain variable fragment (bi-scFv). According to one embodiment, the bi-scFv is a bi-specific tandem scFv or a bi-specific diabody scFv.

In order to retain diffusing ability of the molecular constructs, a molecular size smaller than 250,000 Daltons is preferred. Thus, scFv fragments are preferred for most of the embodiments. At the DNA level, genes are constructed so that the $V_L$ and $V_H$ are linked as a single polypeptide in either order ($V_L$-$V_H$ or $V_H$-$V_L$) by a peptide linker of 10-25 amino acid residues with glycine and serine being the major residues. At the C-terminal, a short stretch with glycine and serine and a terminal residue cysteine is engineered. Recombinant scFv and bi-scFv can be produced in bacteria, such as *E. coli* and *Pseudomonas putida*, in yeast, such as *Pichia pastoris*, or in mammalian cells, such as CHO and HEK293 cell lines.

The inventors' laboratory have produced a large number of IgG antibodies, Fab, scFv and various antibody fragments, Fc-based proteins, and other recombinant antibodies in HEK293 and CHO cell lines for experimentation in in vitro systems and in animal models. Our laboratory has also developed cell lines for producing antibodies for human clinical trials. The HEK293 transient expression system can be conveniently employed to produce up to 1 g of IgG or antibody fragments using a few flasks of 1-2 liters in the research laboratory. The scFv fragments to be used in the molecular constructs of this invention generally do not have a carbohydrate modification, and carbohydrate modification is not required for the binding activity of the scFv to their antigenic targets. Furthermore, only one disulfide bond and one terminal cysteine are present in the scFv fragment. Therefore, small-scale bacterial expression systems have been developed as a manufacturing alternative for producing scFv. With *E. coli*, expression systems for recovering scFv in intracellular inclusion bodies, in periplasm, and in secreted form have been employed. The scFv can be purified in most cases with an affinity column with Protein L, which interacts with $V_H$ of most K light chain, or in other cases with ion-exchange columns.

The examples of this invention based on the joint-linker platform employ mainly scFv and Fab as the targeting and/or effector elements. However, specific binding molecules may also be screened from large libraries of binding molecules based on sdAb or other antibody fragments. Libraries of binding molecules, which are not based on immunoglobulin domains but resemble antibodies in having specific binding affinities to selected target molecules, include (1) aptamers, which are oligonucleotides or short peptides selected for binding to target molecules, (2) fynomers, which are small binding proteins derived from the human Fyn SH3 domain, (3) affimers, which are binding proteins derived from the cysteine protein inhibitor family of cystatins, and (4) DARPins (designed ankyrin repeat proteins), which are genetically engineered proteins with structures derived from the natural ankyrin proteins and consist of 3, 4, or 5 repeat motifs of these proteins. These antibody-mimetics have molecular weights of about 10K to 20K Daltons.

II-(ii) Functional Elements Suitable for Use with Joint-Linker Molecular Construct As discussed above, the present joint-linker comprises at least two linker units, in which the first linker unit carries one or more targeting elements, and the second linker unit carries one or more effector elements or pharmacokinetic property-enhancing elements, and vice versa. Specific examples of the functional elements incorporated in the present joint-linker molecular construct for treating a particular disease are discussed below.

In constructing joint-linker molecular constructs for treating diseases/conditions associated with blood clots, one may use an scFv specific for fibrin as the targeting element. In the case where the prevention of blood clot formation is the main purpose, the present joint-linker molecular constructs may use Factor Xa inhibitors or thrombin inhibitors as the effector element. Illustrative examples of Factor Xa inhibitors include apixaban, edoxaban, and rivaroxaban. Non-limiting examples of thrombin inhibitors include argatroban and melagatran. For joint-linker molecular constructs aiming to treat thrombosis, tissue plasminogen activators, such as alteplase, reteplase, tenecteplase, and lanoteplase, can be used as the effector element.

II-(iii) Use of Joint-Linker Molecular Construct

The present disclosure also pertains to methods for preventing the formation of blood clot and treating thrombosis using the suitable joint-linker molecular construct. Generally, the method comprises the step of administering to a subject in need of such treatment an effective amount of the joint-linker molecular construct according to embodiments of the present disclosure.

EXPERIMENTAL EXAMPLES

Example 1: Synthesis of Peptide 1 (SEQ ID NO: 18) as Peptide Core, and Conjugation of SH Group of Cysteine Residue with Maleimide-PEG$_4$-Tetrazine as Conjugating Arm The synthesized peptide 1 (Chinapeptide Inc., Shanghai, China) was dissolved in 100 mM sodium phosphate buffer (pH 7.0) containing 50 mM NaCl and 5 mM EDTA at 2 mM final concentration. The dissolved peptide was reduced by 1 mM TCEP at 25° C. for 2 hours. For conjugating the SH group of cysteine residue with maleimide-PEG$_4$-tetrazine (Conju-probe Inc.) to create a functional linking group tetrazine, the peptide and maleimide-PEG$_4$-tetrazine were mixed at a 1/5 ratio and incubated at pH 7.0 and 4° C. for 24 hours. Tetrazine-conjugated peptides were purified by reverse phase HPLC on a Supelco C18 column (250 mm×10 mm; 5 µm), using a mobile phase of acetonitrile and 0.1% trifluoroacetic acid, a linear gradient of 0% to 100% acetonitrile over 30 minutes, at a flow rate of 1.0 mL/min and a column temperature of 25° C.

The present tetrazine-peptide 1, as illustrated below, had a m.w. of 2,185.2 Daltons.

(SEQ ID NO: 18)

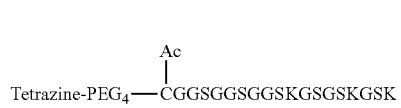

Example 2: Synthesis of Peptide 2 (SEQ ID NO: 26) as Peptide Core, and

Conjugation of the SH Group of Cysteine Residue with Maleimide-PEG$_3$-Transcyclooctene (TCO) as a Coupling Arm The synthesized peptide 2 (Chinapeptide Inc., Shanghai, China) was processed similarly. Briefly, the peptide was dissolved in 100 mM sodium phosphate buffer (pH 7.0) containing 50 mM NaCl and 5 mM EDTA at a final concentration of 2 mM. The dissolved peptide was reduced by 1 mM tris(2-carboxyethyl)phosphine (TCEP) at 25° C. for 2 hours. For conjugating the SH group of the cysteine residue with maleimide-PEG$_3$-TCO (Conju-probe Inc.) to create a functional linking group TCO, the peptide and maleimide-PEG$_3$-TCO were mixed at a 1/7.5 ratio and incubated at pH 7.0 and 25° C. for 18 hours. TCO-conjugated peptides were purified by reverse phase HPLC on a Supelco C18 column (250 mm×10 mm; 5 μm), using a mobile phase of acetonitrile and 0.1% trifluoroacetic acid, a linear gradient of 0% to 100% acetonitrile over 30 minutes, at a flow rate of 1.0 mL/min and a column temperature of 25° C.

The identification of the synthesized TCO-peptide (illustrated below) was carried out by MALDI-TOF mass spectrometry. Mass spectrometry analyses were performed by the Mass Core Facility at the Institute of Molecular Biology (IMB), Academia Sinica, Taipei, Taiwan. Measurements were performed on a Bruker Autoflex III MALDI-TOF/TOF mass spectrometer (Bruker Daltonics, Bremen, Germany).

The thus-synthesized TCO-peptide 2, as illustrated below, had a m.w. of 2, 020.09 Daltons.

(SEQ ID NO: 26)

Example 3: Synthesis of Linker Unit by Conjugating NHS-PEG$_{12}$-Maleimide to NH$_2$ Groups of Tetrazine-Peptides 1

Three linking arms of PEG$_{12}$-maleimide were attached to the peptide core tetrazine-peptide 1. The crosslinker, NHS-PEG$_{12}$-maleimide (succinimidyl-[(N-maleimido-propionamido)-dodecaethyleneglycol] ester, was purchased from Conju-probe Inc. The conjugation procedure was performed per the manufacturer's instruction; the peptide with lysine residues was dissolved in the conjugation buffer, phosphate buffered saline (PBS, pH 7.5) at 100 mM. NHS-PEG$_{12}$-maleimide crosslinker was added to the dissolved peptide at 1 mM final concentration (10-fold molar excess over 0.1 mM peptide solution). The reaction mixtures were incubated for 18 hours at room temperature. PEG$_{12}$-maleimide-conjugated tetrazine-peptide 1 was purified by reverse phase HPLC on a Supelco C18 column (250 mm×4.6 mm; 5 μm), using a mobile phase of acetonitrile and 0.1% trifluoroacetic acid, a linear gradient of 0% to 100% acetonitrile over 30 minutes, at a flow rate of 1.0 ml/min and a column temperature of 25° C.

As illustrated below, the present PEG$_{12}$-maleimide-conjugated tetrazine-peptide 1 carried one coupling arm with a tetrazine group and three PEG linking arms with maleimide groups; it had a m.w. of 4,461 Daltons.

(SEQ ID NO: 18)

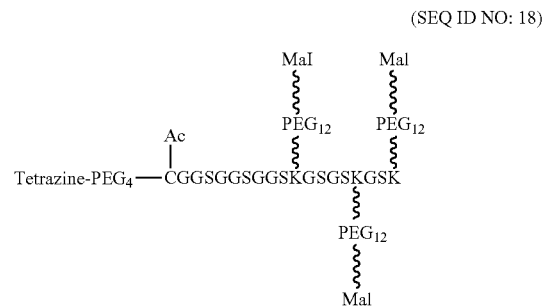

Example 4: Synthesis of Linker Unit by Conjugating NHS-PEG$_6$-Mal to NH$_2$ Groups of TCO-Peptide 2

The procedure for conjugating NHS-PEG$_6$-Mal to NH$_2$ groups of TCO-peptide 2 was performed similarly as described in the previous Example. Briefly, NHS-PEG$_6$-maleimide crosslinker was added to the dissolved peptide at 40 mM final concentration (20-fold molar excess over 2 mM peptide solution). The reaction mixtures were incubated for 3 hours at room temperature.

Figure 8:
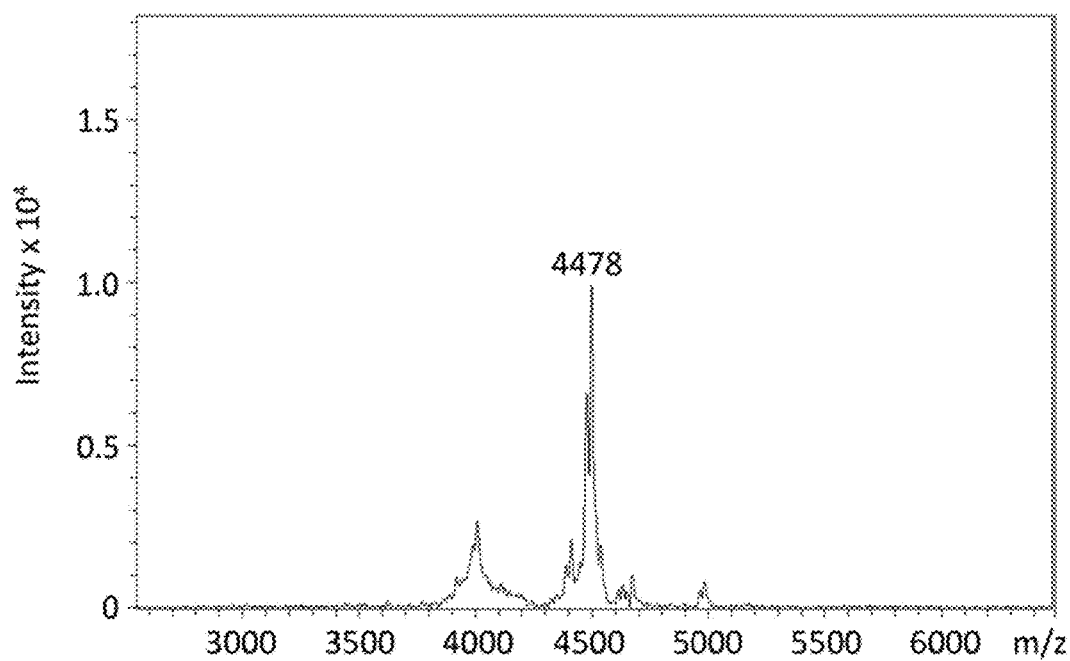
FIG. 8 shows the mass spectrometry MALDI-TOF result of a peptide core-based linker-unit carrying one linking arm with TCO group and five PEG6 linking arms with maleimide groups, according to one working example of the present disclosure.

The present PEG$_6$-maleimide-conjugated peptide 2, as illustrated below, had a m.w. of 4,478 Daltons; it was a peptide core-based linker unit carrying one TCO group and five PEG linking arms with maleimide groups (FIG. 8).

(SEQ ID NO: 26)

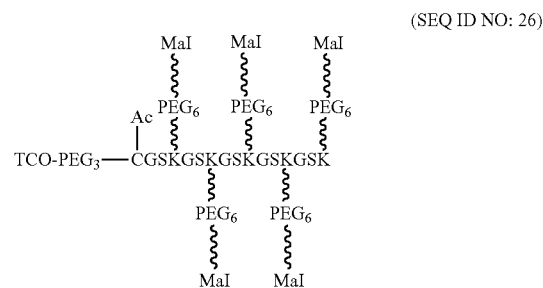

Example 5: Conjugation of Apixaban Carboxylic Acid Molecule with NH$_2$-PEG$_3$-S-S-PEG$_3$-NH$_2$ Crosslinker Apixaban carboxylic acid was purchased from KM3 Scientific Inc. (New Taipei City, Taiwan). The activated carboxyl group of apixaban carboxylic acid molecule was reacted with a homo-bifunctional cleavable crosslinker, NH$_2$-PEG$_3$-S-S-PEG$_3$-NH$_2$ as shown in scheme 12.

Apixaban carboxylic acid was dissolved in 100% DMSO at a final concentration of 20 mM, and NH$_2$-PEG$_3$-S-S-

PEG$_3$-NH$_2$, a homo-bifunctional cleavable crosslinker, was dissolved in PBS at a 10 mM final concentration. To activate the carboxyl group of apixaban carboxylic acid, 1-ethyl-3-(3-dimethylaminopropyl)carbodiimide hydrochloride (EDC) (KM3 Scientific Inc.) was added to the apixaban carboxylic acid solution at a molar ratio of 1:2 ([apixaban]:[EDC]) and then incubated for 15 minutes.

The activated apixaban carboxylic acid solution was added to the NH$_2$-PEG$_3$-S-S-PEG$_3$-NH$_2$ crosslinker at a 2 mM final concentration (5-fold molar excess over 0.4 mM NH$_2$-PEG$_3$-S-S-PEG$_3$-NH$_2$ crosslinker solution). The reaction mixture was incubated for 3 hours at room temperature.

that the molecular construct had m.w. of 1,301.64 and 1,323.68 Daltons, corresponding to [M+H]$^+$ and [M+Na]$^+$, respectively.

Example 6: Conjugation of Two Argatroban Molecules to an NH$_2$-PEG$_3$-S-S-PEG$_3$-NH$_2$ Crosslinker Argatroban was purchased from KM3 Scientific Inc. (New Taipei City, Taiwan). The procedure for conjugating NH$_2$-PEG$_3$-S-S-PEG$_3$-NH$_2$ to COOH groups of argatroban molecule was performed similarly as described in the pre- <<Scheme 12 Conjugation of two apixaban carboxylic acid molecules to an NH$_2$—PEG$_3$—S—S—PEG$_3$—NH$_2$ crosslinker>>

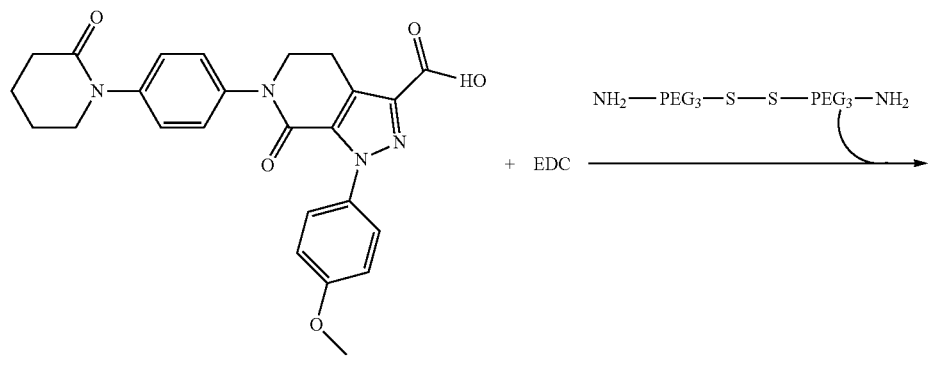

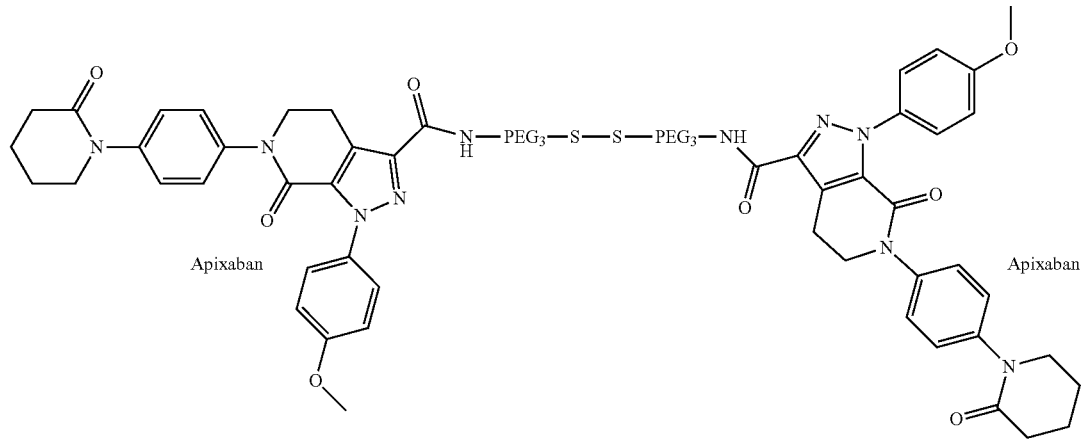

Apixaban-PEG$_3$-S-S-PEG$_3$-apixaban was purified by reverse phase HPLC on a Supelco C18 column (250 mm×4.6 mm; 5 µm), using a mobile phase of acetonitrile and 0.1% trifluoroacetic acid, a linear gradient of 0% to 100% acetonitrile over 30 minutes, at a flow rate of 1.0 ml/min and a column temperature of 25° C.

Figure 9:
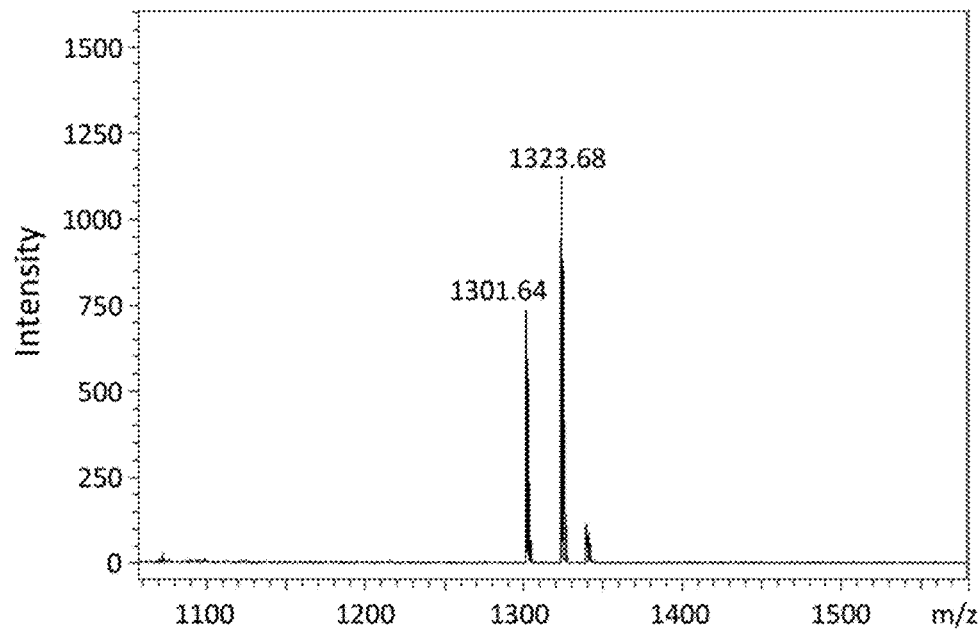
FIG. 9 shows the mass spectrometry MALDI-TOF result of the apixaban-$PEG_3$-S-S-$PEG_3$-apixaban synthetized according to one working example of the present disclosure.

The mass spectroscopic analysis of the thus-synthesized apixaban-PEG$_3$-S-S-PEG$_3$-apixaban (see, FIG. 9) indicated vious Example. Briefly, argatroban was dissolved in 100% DMSO at a final concentration of 20 mM. EDC solution was added to the argatroban solution to activate COOH group of argatroban and then incubated for 15 minutes. The activated argatroban solution was added to NH$_2$-PEG$_3$-S-S-PEG$_3$-NH$_2$ crosslinker solution at a 2 mM final concentration (5-fold molar excess over 0.4 mM NH$_2$-PEG$_3$-S-S-PEG$_3$-NH$_2$ crosslinker solution) (see, scheme 13).

<<Scheme 13 Conjugation of argatroban molecule with an NH$_2$—PEG$_3$—S—S—PEG$_3$—NH$_2$ crosslinker>>

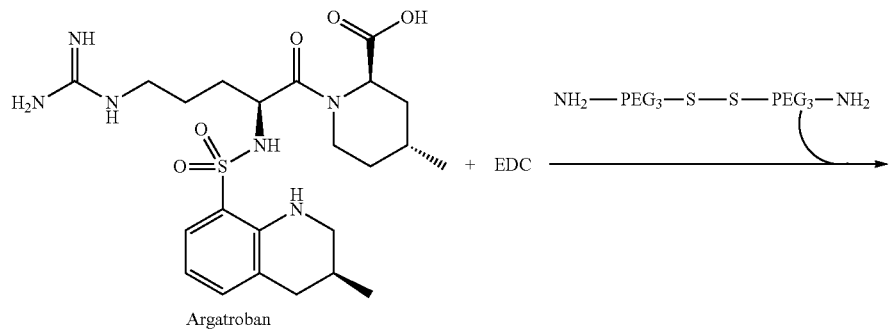

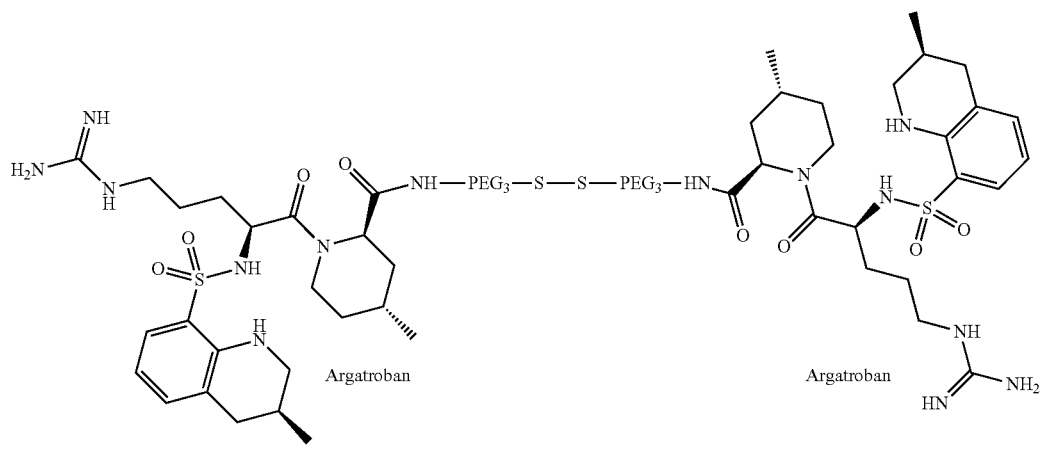

Figure 10:
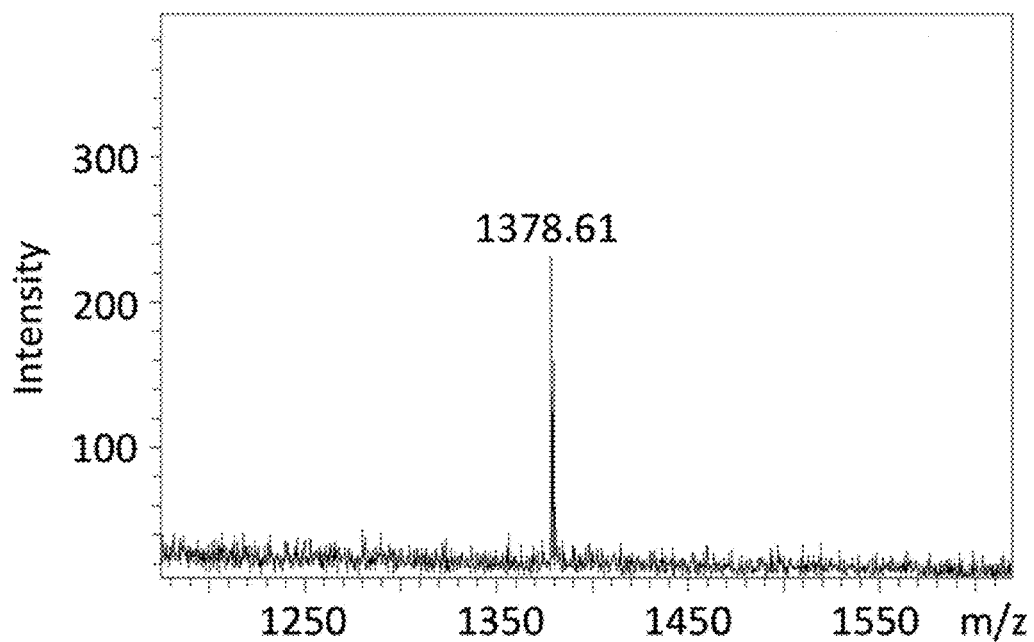
FIG. 10 shows the mass spectrometry MALDI-TOF result of the argatroban-$PEG_3$-S-S-$PEG_3$-argatroban synthetized according to one working example of the present disclosure.

The MALDI-TOF result provided in FIG. 10 shows that the thus-synthesized argatroban-PEG$_3$-S-S-PEG$_3$-argatroban had a m.w. of 1,378.61 Daltons.

Example 7: Conjugation of Apixaban-PEG$_3$-SH and Argatroban-PEG$_3$-SH to Maleimide-PEG$_6$-Conjugated TCO-Peptide 2

Prior to conjugation with the TCO-peptide 2 that had five maleimide-PEG$_6$ linking arms, apixaban-PEG$_3$-S-S-PEG$_3$-apixaban and argatroban-PEG$_3$-S-S-PEG$_3$-argatroban (prepared in the preceding Examples) were incubated with 4 mM TCEP at a molar ratio of 3:1 ([TCEP]:[drug-linker]) at room temperature for 90 minutes with gentle shaking to generate the apixaban-PEG$_3$-SH and argatroban-PEG$_3$-SH molecule with a free sulfhydryl group.

The thus-synthesized drug bundle, as illustrated below, was composed of a linker unit with a free TCO functional group and a set of five apixaban molecules as effector elements. The present molecular construct had a m.w. of 7,713 Daltons, corresponding to [M+H]$^+$.

(SEQ ID NO: 26)

```
        apixaban apixaban  apixaban
           ≷       ≷        ≷
           PEG₆    PEG₆     PEG₆
        Ac  ≷      ≷        ≷
         |  ≷      ≷        ≷
TCO-PEG₃—CGSKGSKGSKGSKGSK
                  ≷      ≷
                  PEG₆   PEG₆
                  ≷      ≷
                apixaban apixaban
```

Another thus-synthesized drug bundle, as illustrated below, was composed of a linker unit with a free TCO functional group and a set of five argatroban molecules as effector elements. The present molecular construct had a m.w. of 8,112.8 Daltons, corresponding to [M+H]$^+$.

(SEQ ID NO: 26)

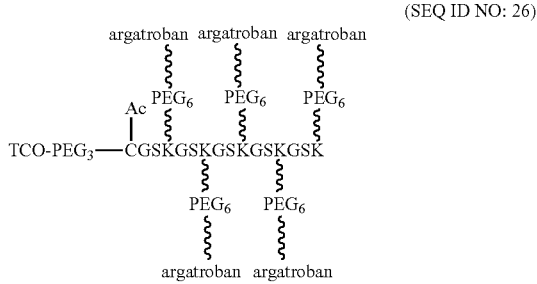

Example 8: Production of Mouse scFv of mAb Specific for Human Fibrin by Expi293F Overexpression System The $V_L$ and $V_H$ of the scFv specific for human fibrin were from mouse monoclonal antibody 102-10 (Japanese Patent Application Publication No. 2012-72). The scFv derived from this antibody was designed to contain a flexible linker of GGGGSGGGGS (SEQ ID NO: 36) and a terminal cysteine residue at the C-terminus. The cysteine residue provides a sulfhydryl group for conjugation with maleimide group present at the free ends of liking arms in various linker units. To produce the scFv of mAb specific for human fibrin, we used the $V_H$ and $V_L$ DNA sequences of mAb 102-10 with further codon optimization. DNA sequences encoding $V_L$-GSTSGSGKPGSGEGSTKG (SEQ ID NO: 37)-$V_H$-(GGGGS)$_2$ (SEQ ID NO: 36)-C were synthesized. The amino acid sequence of the scFv of mAb 102-10 prepared for the experiments in the present invention is set forth in SEQ ID NO: 27.

For preparing scFv proteins using a mammalian expression system, we used the overexpression system based on Expi293F™ cell line for experimentation. The system employed ExpiFectamine™ 293 transfection kit (Life Technologies, Carlsbad, USA) consisting of the Expi293F™ cell line, the cationic lipid-based ExpiFectamine™ 293 Reagent and ExpiFectamine™ 293 transfection Enhancers 1 and 2, and the medium (Gibco, New York, USA).

Figure 11A:
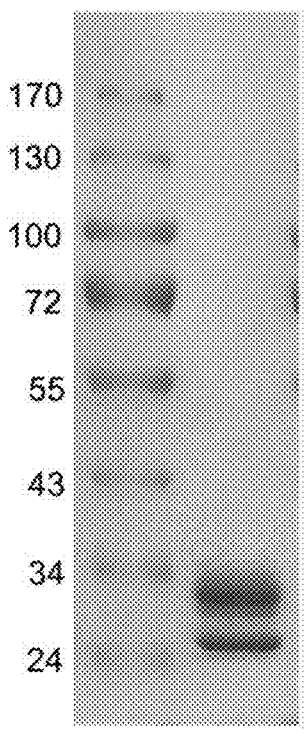
FIGS. 11A, 11B, and 11C respectively show the results of SDS-PAGE, MALDI-TOF and ELISA analysis of purified 102-10 scFv specific for human fibrin, according to one working example of the present disclosure.
Figure 11B:
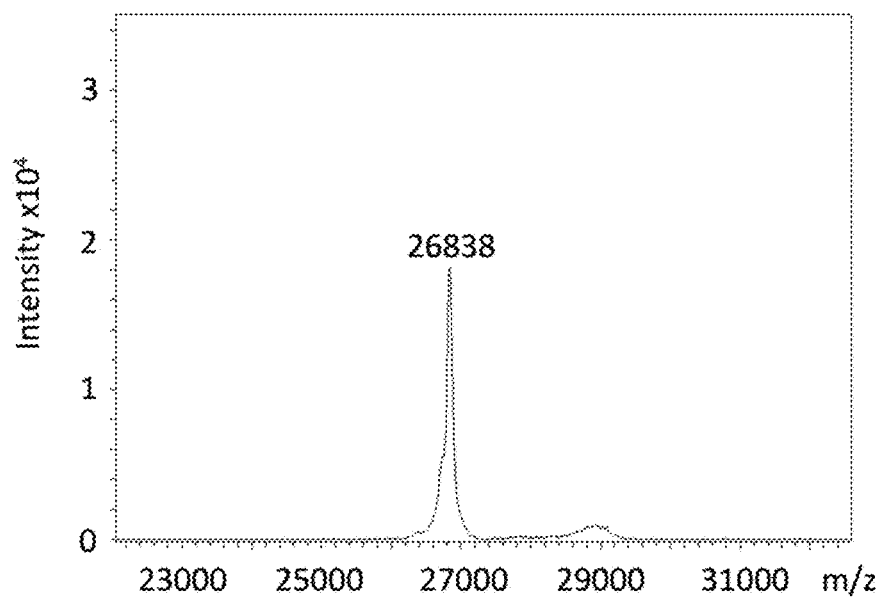

The scFv-encoding sequence was placed in pG1K expression cassette. Expi293F cells were seeded at a density of 2.0×10$^6$ viable cells/ml in Expi293F expression medium and maintained for 18 to 24 hours prior to transfection to ensure that the cells were actively dividing at the time of transfection. On the day of transfection, 7.5×10$^8$ cells in 255 ml medium in a 2-liter Erlenmeyer shaker flask were transfected by ExpiFectamine™ 293 transfection reagent. The transfected cells were incubated at 37° C. for 16 to 18 hours post-transfection in an orbital shaker (125 rpm) and the cells were added ExpiFectamine™ 293 transfection enhancer 1 and enhancer 2 to the shaker flask, and incubated for another 5 to 6 days. Culture supernatants were harvested and scFv proteins in the media were purified using Protein L affinity chromatography. FIGS. 11A and 11B respectively show the results of SDS-PAGE and Mass spectrometric analysis of purified scFv of mAb specific for human fibrin. The scFv of mAb specific for human fibrin in SDS-PAGE migrated in two major bands of 26 and 30 kDa. The same protein solution was further analyzed by MALDI-TOF and showed that the 102-10 scFv specific for human fibrin had only the molecular weight of 26,838 Daltons, which is consistent with the calculated molecular weight.

Example 9: ELISA Analysis of Purified Mouse scFvs Specific for Human Fibrin

To prepare fibrinogen-coated plates, each plate was prepared according to procedures described in US patent application publication 2016/0011217A1. Briefly, 100 μl of human fibrinogen (Sigma) in PBS was added to 96-well flat-bottom plates (Nunc) at 1 μg/well, and the plate was sealed and allowed to stand at 4° C. overnight.

The fibrin plate was prepared as follows. The fibrinogen solution was removed and then 100 μL of TBS containing 0.05 U/ml thrombin (Sigma), 2 mM CaCl$_2$) and 7 mM L-cysteine (Sigma) was added to the wells. The thrombin-treated plate was incubated at 37° C. for 1 hour to allow fibrin formation. The thrombin solution was then removed and blocked with 10% skim milk at room temperature for 1 hour.

Then, 100 μl of the 102-10 scFv solution was added to the fibrinogen plate and the fibrin plate, which were then shaken at room temperature for 1 hour. After that, each plate was washed with TBS-T, and 50 μl of TMB (Thermo Fisher Scientific Inc., Waltham, USA) was added, and colorimetry was conducted. The reaction was stopped by adding 50 μl of 1N HCl. Then the absorbance (O.D.) was obtained by measuring the absorbance at 450 nm with a plate reader.

Figure 11C:
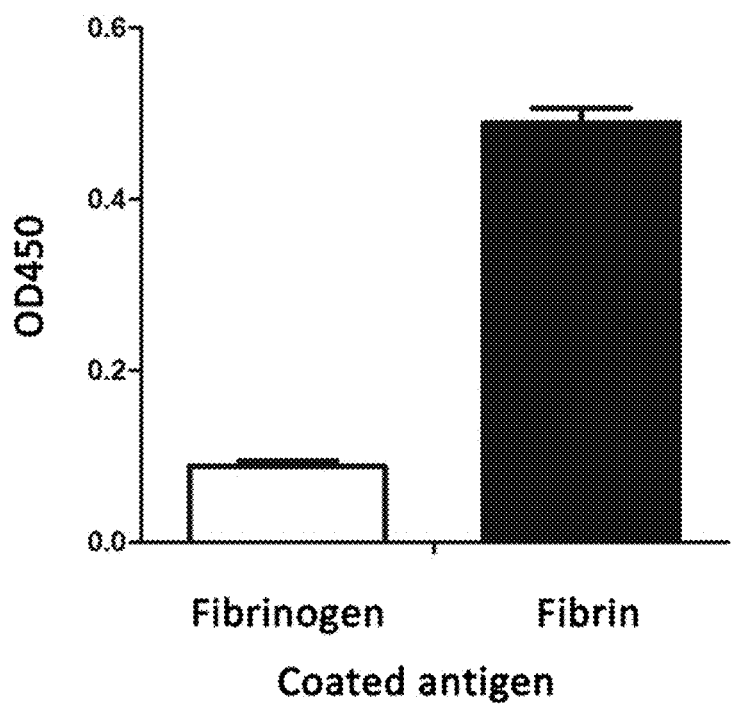

FIG. 11C shows the ELISA result, indicating that the purified 102-10 scFv bound specifically to human fibrin, but not to fibrinogen.

Example 10: Construction and Selection of Phage-Displayed Human scFvs Specific for Human Fibrin The phage clones carrying the human scFv specific for human fibrin were obtained through a contractual arrangement with Dr. An-Suei Yang's laboratory at the Genomics Research Center, Academia Sinica, Taipei, Taiwan. The framework sequence of the GH2 scFv library was derived from a human IgG antibody fragment, G6 anti-VEGF Fab (Protein Bank Code 2FJG) and cloned into restriction sites SfiI and NotI of phagemid vector pCANTABSE (GE Healthcare), carrying an ampicillin resistance, a lacZ promotor, a pelB leader sequence for secretion of scFv fragments into culture supernatants, and an E-tag applicable for detection. The $V_H$ and $V_L$ domains of the scFv template were diversified separately based on the oligonucleotide-directed mutagenesis procedure; the three CDRs in each of the variable domains were diversified simultaneously. The scFv library of over 10$^9$ clones was used for selections on human fibrin.

The thrombin-treated fibrin plates (1 μg/100 μl per well) were prepared as described in the preceding Examples. The fibrin plates were used for panning anti-fibrin antibodies. In brief, the fibrin-coated wells were treated with blocking buffer (5% skim milk in PBST (phosphate buffered saline with 0.1% tween-20)) for 1 hour at room temperature. Recombinant phages in the blocking buffer diluted to 8×10$^{11}$ CFU/ml was added to the fibrin-coated wells for 1 hour with gentle shaking; CFU stands for colony-forming unit. The wells were then washed vigorously 10 times with PBST, followed by 6 times with PBS to remove nonspecific binding phages. The bound phages were eluted using 0.1 M HCl/ glycine buffer at pH 2.2, and eluted fraction was neutralized immediately by 2 M Tris-base buffer at pH 9.0. E. coli strain ER2738 (OD600=~0.6) was used for phage infection at 37° C. for 30 minutes; non-infected E. coli was eliminated by treating with ampicillin for 30 minutes. After ampicillin treatment, helper phage M13KO7 carrying kanamycin resistance was added for another 1 hour incubation. The selected phages rescued by helper phage in the *E. coli* culture were amplified with vigorously shaking overnight at 37° C. in the presence of kanamycin. The amplified phages were precipitated in PEG/NaCl, and then resuspended in PBS for the next selection-amplification cycle. A total of three consecutive panning rounds were performed on human fibrin by repeating this selection-amplification procedure.

Figure 12A:
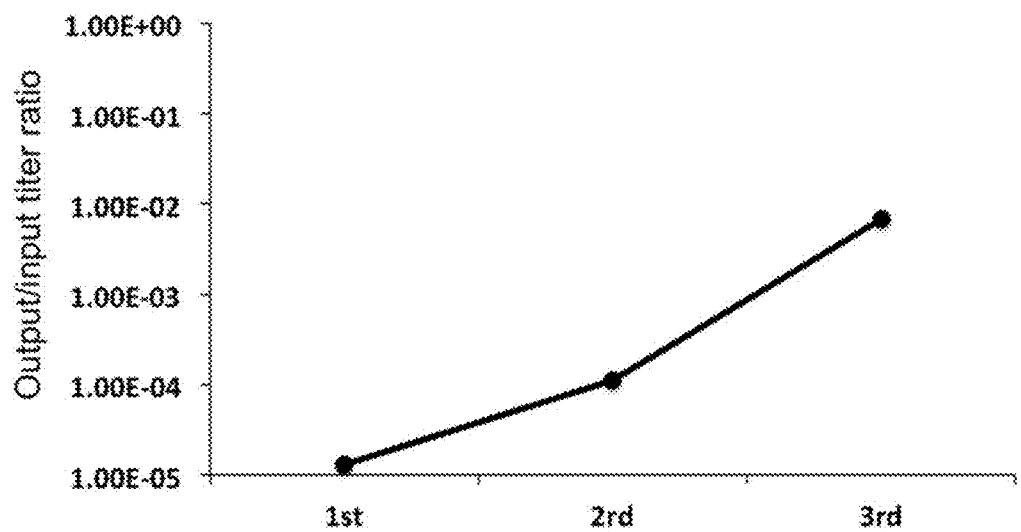
FIG. 12A and FIG. 12B respectively show the results of phage titer analysis and single colony ELISA analysis of phage-displayed scFvs specific for human fibrin, according to one working example of the present disclosure.

Phage-infected ER2738 colonies were enumerated by serial dilution series were counted and phage titers were calculated, yielding the output titer/ml (CFU/ml) per panning round. A 1000-fold increase in phage output title from 2.5E+06 CFU/well to 4.3E+09 CFU/well was obtained after three rounds of panning. The phage output/input titer ratios from each round are shown in FIG. 12A. For each panning round, the phage output/input titer ratios are given on the y-axis. There was clear enrichment of the positive clones over the three rounds of panning. The third panning round resulted in a 500-fold on the ratios of phage output/input titer over the first round, as the binding clones became the dominant population in the library.

In a typical selection procedure, after three rounds of antigen-panning on human fibrin-coated wells in ELISA plates, approximately 80% of the bound phage particles bound to fibrin specifically in ELISA with coated fibrin.

Example 11: Single Colony ELISA Analysis of Human Phage-Displayed scFvs Specific for Human Fibrin

*E. coli* strain ER2738 infected with single-clonal phages each harboring a selected scFv gene in its phagemid was grown in the mid-log phase in 2YT broth (16 g/L tryptone, 10 g/l yeast extract, 5 g/l NaCl, pH 7.0) with 100 µg/ml ampicillin in deep well at 37° C. with shaking. After broth reaching an OD600 of 1.0, IPTG was added to final concentration of 1 µg/ml. The plates were incubated at 37° C. overnight with rigorously shaking. After overnight incubation at 37° C. with vigorous shaking, the plates were centrifuged at 4,000 g for 15 minutes at 4° C.

For soluble scFv binding test, ELISA was carried out. In brief, 96-well Maxisorp 96-well plate (Nunc) was coated with fibrin (1 µg/100 µl PBS per well) or a negative control antigen human fibrinogen for 18 hours with shaking at 4° C. After treated with 300 µl of blocking buffer for 1 hour, 100 µl of secreted scFv in the supernatant was mixed with 100 µl of blocking buffer and then added to the coated plate for another 1 hour. Goat anti-E-tag antibody (conjugated with HRP, 1:4000, Cat. No. AB19400, Abcam) was added to the plate for 1 hour. TMB substrate (50 µl per well) was added to the wells and the absorbance at 450 nm was measured after reactions were stopped by adding 1N HCl (50 µl per well).

Figure 12B:
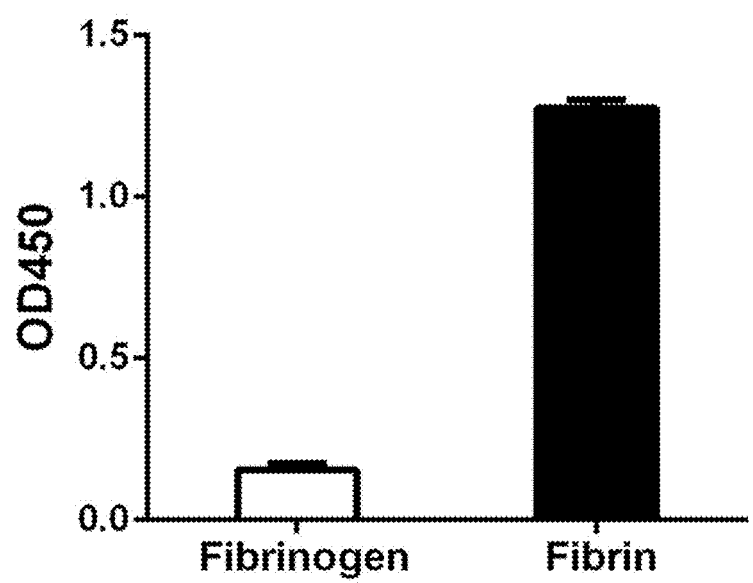

A total of 960 phage clones after the 3$^{rd}$ round of panning were subjected to the present analysis. Among them, six scFv clones that bound to fibrin with a differential of OD450 greater than 10 over fibrinogen were further characterized by DNA sequencing of their encoding scFv genes. Four different DNA sequences were identified. FIG. 12B shows the ELISA result of an scFv clone D10. The amino acid sequence of an scFV clone D10, which binds to human fibrin with an OD450 of 1.09, is shown in as SEQ ID NO: 29.

Example 12: Production of Recombinant Reteplase by Expi293F Overexpression System The amino acid sequence of reteplase was from Drug-Bank. The recombinant protein was designed to contain a flexible linker of GGGGSGGGGS (SEQ ID NO: 36) and a terminal cysteine residue at the C-terminus. The cysteine residue provides a sulfhydryl group for conjugation with maleimide group present at the free ends of linking arms in various linker units. The amino acid sequences of reteplase prepared for the experiments of the invention are set forth in SEQ ID NO: 28.

In this Example, the gene-encoding sequence was placed in pcDNA3 expression cassette. For preparing reteplase protein using a mammalian expression system, we used the overexpression system based on Expi293F™ cell line for experimentation as described in the above Examples.

Figure 13A:
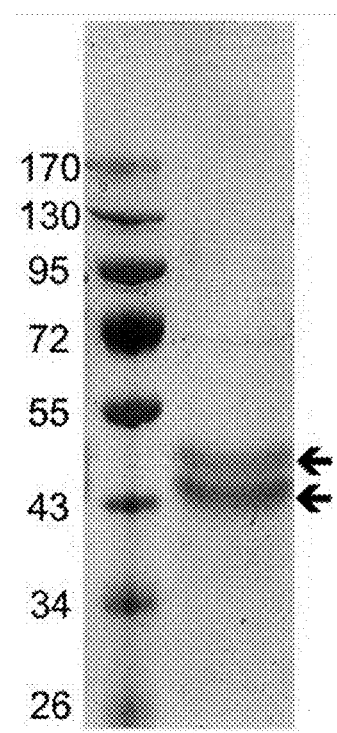
FIG. 13A and FIG. 13B respectively show the results of SDS-PAGE and MALDI-TOF analysis of purified reteplase, according to one working example of the present disclosure.
Figure 13B:
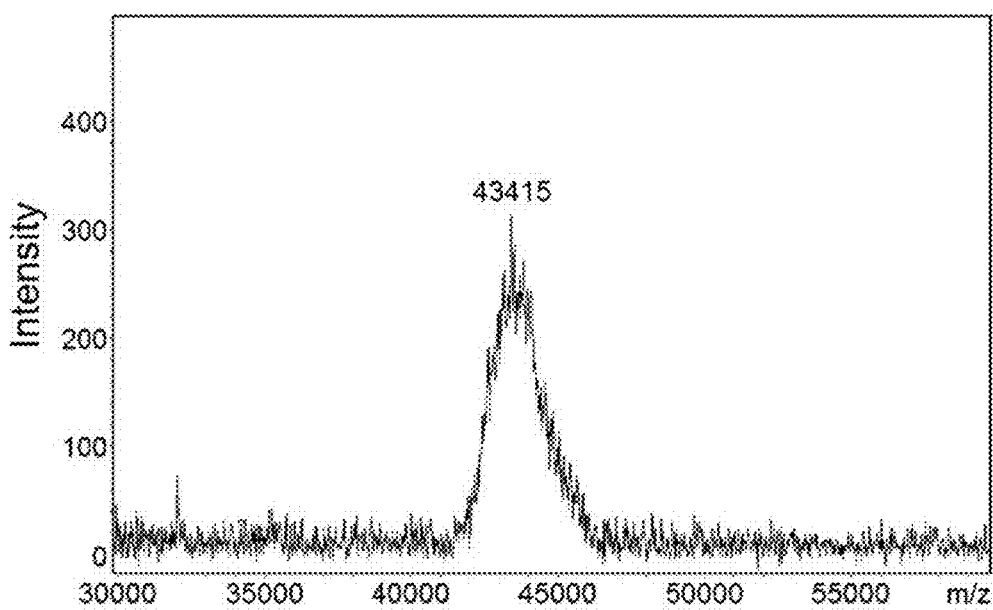

FIGS. 13A and 13B respectively show results of SDS-PAGE and mass spectrometric analyses of purified reteplase. The recombinant reteplase in SDS-PAGE migrated in two major bands of 43 and 48 kDa. The same protein solution was further analyzed by MALDI-TOF and showed that the recombinant reteplase had only a molecular weight of 43,415 Daltons, which is consistent with the calculated molecular weight.

Example 13: Preparation of TCO-Conjugated Reteplase

For the conjugation of SH group of reteplase with Mal-PEG$_3$-TCO (Conju-probe, Inc.), the cysteine residue at the C-terminal end of the purified reteplase was reduced by incubating with 5 mM dithiothreitol (DTT) at room temperature for 4 hours with gentle shaking. The buffer of reduced proteins was exchanged to sodium phosphate buffer (100 mM sodium phosphate, pH7.0, 50 mM NaCl, and 5 mM EDTA) by using NAP-10 Sephadex G-25 column. After the reduction reaction and buffer exchange, conjugation was conducted overnight at room temperature in a reaction molar ratio of 10:1 [(Mal-PEG$_3$-TCO:[protein]]. The excess cross-linker was removed by a desalting column and the TCO-conjugated protein product was analyzed.

Figure 14:
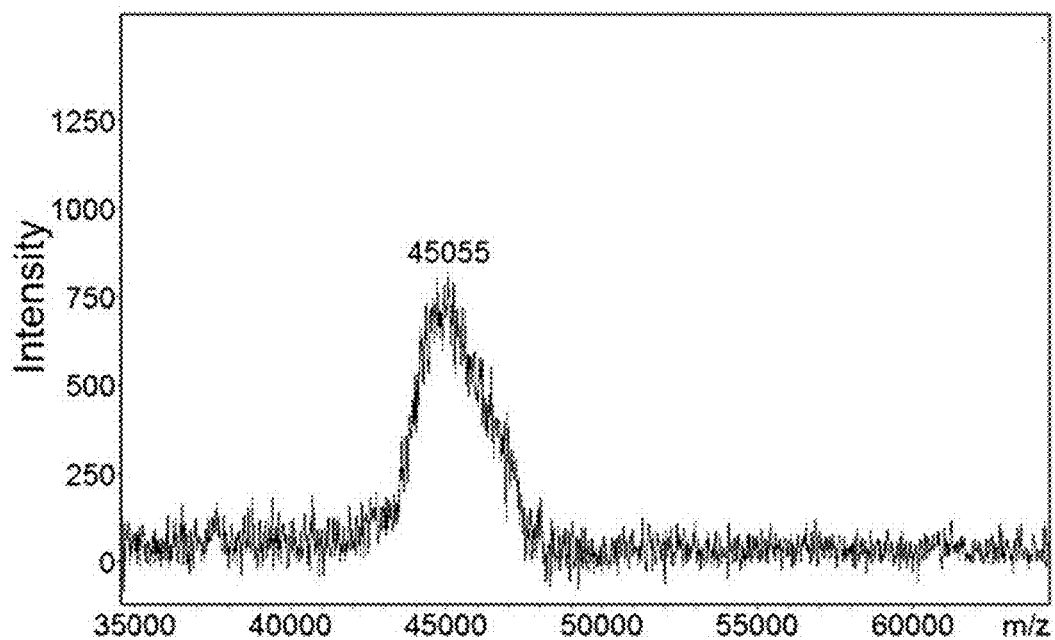
FIG. 14 shows the result of mass spectrometric analysis of TCO-conjugated reteplase, according to one working example of the present disclosure.

The results of mass spectroscopy MALDI-TOF analysis indicated that the sample of TCO-conjugated reteplase protein had a m.w. of 45,055 Daltons. The purity of TCO-conjugated reteplase protein was identified through Coomassie blue staining of 10% SDS-PAGE. FIG. 14 shows mass spectrometric analysis of TCO-conjugated reteplase.

Example 14: Conjugation of Three scFvs Specific for Human Fibrin to the Three Maleimide-PEG$_{12}$ Linking Arms Based on Tetrazine-Peptide 1

The DNA sequence encoding SEQ ID NO: 27 was synthesized and expressed as in the above Examples. Prior to conjugation with the tetrazine-peptide 1 that had three PEG$_{12}$-maleimide linking arms, the cysteine residue at the C-terminal end of the purified 102-10 scFv of mAb specific for human fibrin was reduced by incubating with 5 mM DTT at a molar ratio of 2:1 ([DTT]:[scFv]) at room temperature for 4 hours with gentle shaking. Subsequently, the buffer of the reduced 102-10 scFv was exchanged to maleimide-SH coupling reaction buffer (100 mM sodium phosphate, pH 7.0, 50 mM NaCl and 5 mM EDTA) by using an NAP-10 Sephadex G-25 column (GE Healthcare). After the reduction and buffer exchange, the conjugation to the tetrazine-peptide 1 having three PEG$_{12}$-maleimide linking arms was conducted overnight at 4° C. at a molar ratio of 1:4 ([linker]:[Protein]).

Figure 15:
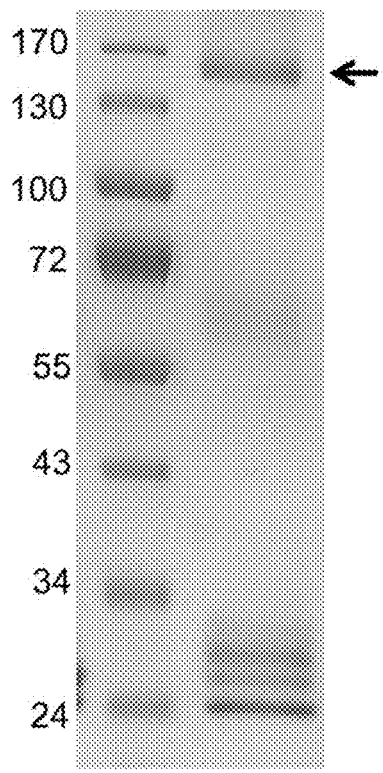
FIG. 15 shows the result of SDS-PAGE analysis of a targeting linker-unit with one free tetrazine functional group and a set of three scFvs specific for human fibrin, according to one working example of the present disclosure.

The reaction mixture was applied to a size exclusion chromatography column S75. The PEG$_{12}$-maleimide-conjugated tetrazine-peptide 1 conjugated with three 102-10 scFvs specific for human fibrin was separated from the free scFv, free PEG$_{12}$-maleimide-conjugated tetrazine-peptide 1 and the PEG$_{12}$-maleimide-conjugated tetrazine-peptide 1 conjugated with one and two 102-10 scFvs specific for human fibrin by size exclusion chromatography column S75. The product (i.e., the PEG$_{12}$-maleimide-conjugated tetrazine-peptide 1 having a free tetrazine functional group and being conjugated with a set of three 102-10 scFvs specific for human fibrin) was purified and shown in the 10% SDS-PAGE analysis shown in FIG. 15.

Figure 16:
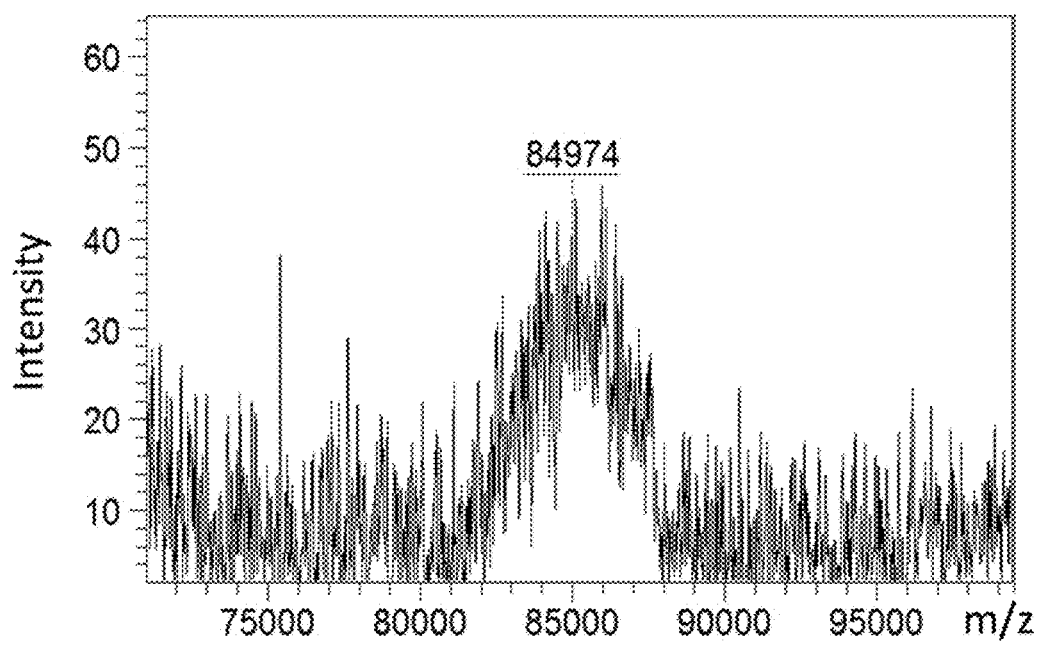
FIG. 16 shows the MS result on a single linker-unit molecular construct with three scFvs specific for human fibrin (as targeting elements) and one reteplase molecule (as the effector element), according to one working example of the present disclosure.

Example 15: Analysis of a Targeting Linker Unit Containing Three scFvs Specific for Human Fibrin Linked to the Three Maleimide-PEG$_{12}$ Linking Arms Based on Tetrazine-Peptide 1 by MALDI-TOF The sample of the targeting linker unit of three 102-10 scFvs specific human fibrin linked to the three maleimide-PEG$_{12}$ linking arms based on tetrazine-peptide 1 was analyzed by MALDI-TOF. The median of the experimental molecular weight was consistent with the median of theoretical molecular weight of three 102-10 scFvs specific for human fibrin conjugated to tetrazine-peptide 1 with three maleimide-PEG$_{12}$ linking arms. According to the mass spectrometric profile in FIG. 16, the synthesized targeting linker unit had the median molecular weight of 84,974 Daltons.

Illustrated below is the synthesized targeting linker unit that was composed of a linker unit with a free tetrazine functional group and a set of three 102-10 scFvs specific for human fibrin as targeting elements.

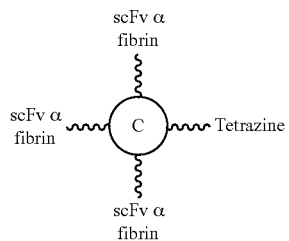

Example 16: Preparation of Molecular Construct with Three scFvs Specific for Human Fibrin as Targeting Elements and One Reteplase Molecule as an Effector Element In this example, the targeting linker unit of the preceding examples and a TCO-conjugated reteplase protein was coupled via a tetrazine-TCO iEDDA reaction. Specifically, the targeting linker unit had three 102-10 scFvs specific for human fibrin and one free tetrazine group.

The procedure for tetrazine-TCO ligation was performed per the manufacturer's instructions (Jena Bioscience GmbH, Jena, Germany). Briefly, 100 µl of the targeting linker unit (0.3 mg/ml) was added to the solution containing the effector element at a molar ratio of 1:1.2 ([tetrazine]:[TCO]). The reaction mixture was incubated for 1 hour at room temperature.

Illustrated below is the present joint-linker molecular construct with three 102-10 scFvs specific for human fibrin as targeting elements and with a reteplase molecule as effector elements. In 8% SDS-PAGE analysis of the reaction mixture, a band of about 180 kDa in size was observed.

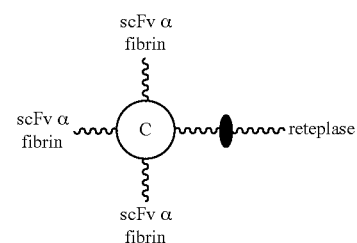

Example 17: Preparation of Molecular Construct with Three scFvs Specific for Human Fibrin as Targeting Elements and Five Apixaban or Argatroban Molecules as an Effector Elements In this example, a joint-linker molecular construct with three 102-10 scFvs specific for human fibrin and a drug bundle of five apixaban molecules was constructed. The molecular construct was made by a TCO-tetrazine iEDDA reaction as described in the preceding Examples. Briefly, 100 µl of the targeting linker unit (0.3 mg/ml) was added to the solution containing the effector element at a molar ratio of 1:1.2 ([tetrazine]:[TCO]). The reaction mixture was incubated for 1 hour at room temperature.

The resultant joint-linker molecular construct, as illustrated below, had three 102-10 scFvs specific for human fibrin as targeting elements and with a drug bundle of five apixaban molecules as effector elements. In 10% SDS-PAGE analysis of the reaction mixture, a band of about 160 kDa in size was observed.

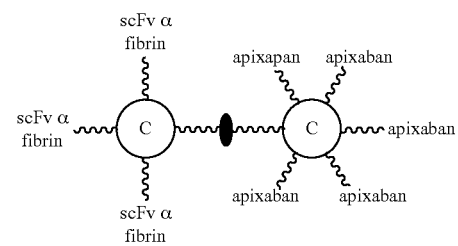

Illustrated below is the present joint-linker molecular construct with three 102-10 scFvs specific for human fibrin as targeting elements and with a drug bundle of five argatroban molecules as effector elements. In 10% SDS-PAGE analysis of the reaction mixture, a band of about 165 kDa in size was observed.

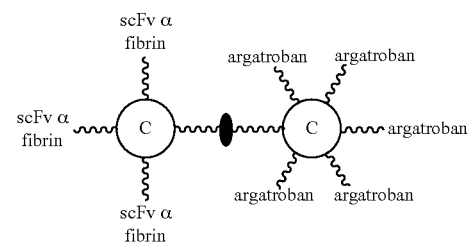

Example 18: Inhibition Assay of Apixaban-PEG$_3$-SH Molecule

Factor Xa catalyzes the conversion of inactive prothrombin to active thrombin. Apixaban has been used as a Factor Xa inhibitor, indirectly to decrease clot formation induced by thrombin. The synthesis of the modified apixaban molecule (apixaban-PEG$_3$-SH) has been shown in the preceding examples. To examine the inhibitory activities of the modified apixaban molecule (apixaban-PEG$_3$-SH), Factor Xa inhibition assay (BioVision, Milpitas, USA) was performed. The Factor Xa inhibition assay utilizes the ability of Factor Xa to cleave a synthetic substrate thereby releasing a fluorophore, which can be detected by a fluorescence reader. In the presence of a Factor Xa inhibitor, the extent of cleavage reaction catalyzed by Factor Xa is reduced or completely abolished.

In this example, 50 µl of Factor Xa enzyme solution (provided by manufacturer) was added to the 96-well flat-bottom plate (Nunc). 10 µl of 1 µM apixaban-PEG$_3$-SH and apixaban carboxylic acid were added to the plate contained Factor Xa enzyme solution and incubated for 15 minutes at room temperature. Then, 40 µl of Factor Xa substrate solution (provided by manufacturer) was added to the plate and incubated at 37° C. for 30 minutes. The fluorescence intensity of fluorophores (relative fluorescence units, RFU) was obtained by measuring the emission at 450 nm under the excitation at 350 nm with fluorescence plate reader.

Figure 17:
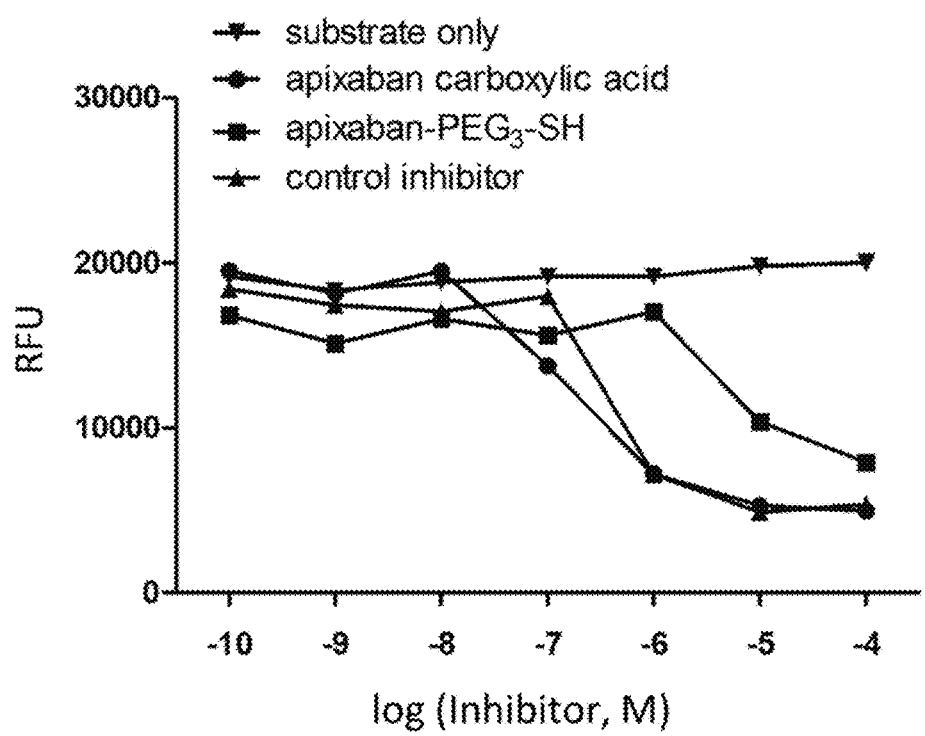
FIG. 17 shows the result of inhibition assay of apixaban-$PEG_3$-SH molecule, according to one working example of the present disclosure.

FIG. 17 shows the assay results of the inhibitory activity of apixaban-PEG$_3$-SH. In the presence of synthetic substrate, Factor Xa activity was measured in the absence of Factor Xa inhibitor (substrate only). The result indicates that the apixaban molecule conjugated with a connecting arm had a similar biological activity to inhibit action of factor Xa as the unmodified apixaban carboxylic acid. A Factor Xa inhibitor (GGACK Dihydrochloride, provided by manufacturer) is used as the control inhibitor.

Example 19: Assay of Biological Activity of Recombinant Reteplase

Reteplase is a recombinant human tissue plasminogen activator that catalyzes the conversion of plasminogen to plasmin; this process is involved in breakdown of blood clots. To investigate the biological activity of the recombinant reteplase, a chromogenic assay in 96-well flat-bottom plate was performed.

Briefly, 1 µl of 1 µM recombinant reteplase, 25 µl of 10 µM human plasminogen (Cat. No. 7549-1, Biovision) and 62.5 µl of 100 mM Tris buffer at pH 8.5 were added and incubated in the well of the plate at 37° C. for 30 minutes. Next, 1 µl of 50 mM chromogenic substrate D-Val-Leu-Lys-p-Nitroanilide dihydrochloride (Cat. No. V7127, Sigma), a synthetic plasmin substrate, was added to the well and incubated at 25° C. for 30 minutes. 31.5 µl of 10% citric acid was then added to each well to stop the reaction. The recombinant reteplase catalyzes plasminogen to form plasmin, which in turn cleaves the chromogenic substrate to release yellow colored p-Nitroanilide, which was measured at 405 nm by a plate reader.

The result shows that recombinant reteplase exhibited a protease activity with an OD405 of 1.8, whereas the positive control protein, the commercially available tPA protein (Cat. No. T0831, Sigma) had an OD405 of 1.5.

It will be understood that the above description of embodiments is given by way of example only and that various modifications may be made by those with ordinary skill in the art. The above specification, examples, and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

---

What is claimed is:

1. A molecular construct comprising a first linker unit and a second linker unit, wherein, the first linker unit comprises,
 a first center core comprising a plurality of amine groups,
 a first linking arm linked to the first center core,
 a first element linked to the first linking arm, and
 optionally, a first coupling arm linked to the first center core;

the second linker unit comprises,
 a second center core comprising a plurality of amine groups,
 a second linking arm linked to the second center core,
 a second element linked to the second linking arm, and
 optionally, a second coupling arm linked to the second center core; and the first and second linker units are coupled to each other via copper catalyzed azide-alkyne cycloaddition (CuAAC) reaction, strained-promoted azide-alkyne click chemistry (SPAAC) reaction or inverse electron demand Diels-Alder (iEDDA) reaction occurred between any of the followings: the first and second center cores, the first coupling arm and the second center core, the first and second coupling arms, or the first center core and the second coupling arm; wherein, the first or second center core is independently a polypeptide core or a compound core, wherein the polypeptide core comprises, (1) a plurality of lysine (K) residues, wherein each K residue and its next K residue are separated by a filler sequence comprising glycine (G) and serine (S) residues, and the number of K residues ranges from 2 to 15; or (2) the sequence of (Xaa-K)n, where Xaa is a PEGylated amino acid having 2 to 12 repeats of ethylene glycol (EG) unit, and n is an integer from 2 to 15; wherein at least one of the N- and C-terminal amino acid residues of the polypeptide is an amino acid having an azide or an alkyne group or is a cysteine residue, and when one of the N- and C-terminal amino acid residues is the cysteine residue, the linker unit further comprises, optionally, the coupling arm that is linked to the cysteine residue via the thiol group of the cysteine residue and has an azide, an alkyne, a tetrazine, a cyclooctene, or a cyclooctyne group at the free terminus thereof; and the compound core is selected from the group consisting of, benzene-1,3,5-triamine, 2-(aminomethyl)-2-methylpropane-1,3-diamine, tris(2-aminoethyl)amine, benzene-1,2,4,5-tetraamine, 3,3',5,5'-tetraamine-1,1'-biphenyl, tetrakis(2-aminoethyl)methane, tetrakis-(ethylamine)hydrazine, N,N,N',N'-tetrakis(aminoethyl)ethylenediamine, benzene-1,2,3,4,5,6-hexaamine, 1-N,1-N,3-N,3-N,5-N,5-N-hexakis(methylamine)-benzene-1,3,5-triamine, 1-N,1-N,2-N,2-N,4-N,4-N,5-N,5-N,-octakis(methylamine)-benzene-1,2,4,5-triamine, and N,N-bis[(1-amino-3,3-diaminoethyl)pentyl]methanediamine; and the first or second coupling arm linked to said compound core is linked thereto via forming an amide bond with one of the plurality of amine groups of the compound core and has an azide, an alkyne, a tetrazine, a cyclooctene, or a cyclooctyne group at the free-terminus thereof;

the first and second linking arms are respectively linked to the amine groups of the first and second center cores via forming an amide bond;

the first and second elements are respectively linked to the first and second linking arms via forming an amide bond, or via thiol-maleimide, CuAAC, iEDDA, or SPAAC reaction; and the first element is an scFv specific for fibrin, and the second element is a tissue plasminogen activator, an inhibitor of Factor Xa, or an inhibitor of thrombin.

2. The molecular construct of claim 1, wherein the first and second linker units respectively comprise a plurality of the first and second linking arms linked thereto.

3. The molecular construct of claim 2, further comprising a plurality of first and second elements respectively linked to the first and second linking arms.

4. The molecular construct of claim 1, wherein,
each of the first and second linking arms is a PEG chain having 2-20 repeats of ethylene glycol (EG) units; and
each of the first and second coupling arms is a PEG chain having 2-12 repeats of EG units.

5. The molecular construct of claim 1, wherein,
one of the first and second coupling arms has the azide group at the free-terminus thereof, and the other of the first and second coupling arms has the alkyne or the cyclooctyne group at the free-terminus thereof; and
the first and second linker units are coupled to each other via copper catalyzed azide-alkyne cycloaddition (CuAAC) reaction or strained-promoted azide-alkyne click chemistry (SPAAC) reaction occurred between the first and second coupling arms.

6. The molecular construct of claim 1, wherein the cyclooctyne group is dibenzocyclooctyne (DBCO), difluorinated cyclooctyne (DIFO), bicyclononyne (BCN), or dibenzocyclooctyne (DICO).

7. The molecular construct of claim 1, wherein,
one of the first and second coupling arms has the tetrazine group at the free-terminus thereof, and the other of the first and second coupling arms has the cyclooctene group at the free-terminus thereof; and
the first and second linker units are coupled to each other via iEDDA reaction occurred between the first and second coupling arms.

8. The molecular construct of claim 1, wherein the tetrazine group is 1,2,3,4-tetrazine, 1,2,3,5-tetrazine or 1,2,4,5-tetrazine, or derivatives thereof.

9. The molecular construct of claim 1, wherein one of the first and the second center cores is the compound core.

10. The molecular construct of claim 1, wherein,
one of the first and the second center cores is the compound core, and the coupling arm linked to the compound core has a DBCO, a DIFO, a BCN, or a DICO group at the free-terminus thereof;
the other of the first and the second center cores is the polypeptide core in which the N- or C-terminal amino acid residue is L-azidohomoalanine (AHA), 4-azido-L-phenylalanine, 4-azido-D-phenylalanine, 3-azido-L-alanine, 3-azido-D-alanine, 4-azido-L-homoalanine, 4-azido-D-homoalanine, 5-azido-L-ornithine, 5-azido-d-ornithine, 6-azido-L-lysine, or 6-azido-D-lysine; and
the first and second linker units are coupled to each other via SPAAC reaction occurred between the coupling arm and the N- or C-terminal amino acid residue.

11. The molecular construct of claim 1, wherein at least one of the first and second center cores is the polypeptide core.

12. The molecular construct of claim 1, wherein the filler sequence has the sequence of GS, GGS, GSG, or SEQ ID NOs: 1-16.

13. The molecular construct of claim 1, wherein the polypeptide core comprises 2-15 units of the sequence of $G_{1-5}SK$.

14. The molecular construct of claim 13, wherein the polypeptide core comprises the sequence of $(GSK)_{2-15}$.

15. The molecular construct of claim 1, wherein the first and second center cores are independently the polypeptide cores.

16. The molecular construct of claim 15, wherein the N-terminus of each of the first and second center cores is modified with an acetyl group.

17. The molecular construct of claim 15, wherein,
the N- or C-terminal amino acid residue of one of the first and second center cores is AHA, 4-azido-L-phenylalanine, 4-azido-D-phenylalanine, 3-azido-L-alanine, 3-azido-D-alanine, 4-azido-L-homoalanine, 4-azido-D-homoalanine, 5-azido-L-ornithine, 5-azido-d-ornithine, 6-azido-L-lysine, or 6-azido-D-lysine;
the N- or C-terminal amino acid residue of the other of the first and second center cores is L-homopropargylglycine (L-HPG), D-homopropargylglycine (D-HPG), or beta-homopropargylglycine (β-HPG); and
the first and second center cores are coupled to each other via copper catalyzed azide-alkyne cycloaddition (CuAAC) reaction occurred between the N- or C-terminal amino acid residues.

18. The molecular construct of claim 15, wherein each of the first and second center cores comprises a cysteine residue at the N- or C-terminus thereof.

19. The molecular construct of claim 15, wherein,
the N- or C-terminal amino acid residue of one of the first and second center cores is AHA, 4-azido-L-phenylalanine, 4-azido-D-phenylalanine, 3-azido-L-alanine, 3-azido-D-alanine, 4-azido-L-homoalanine, 4-azido-D-homoalanine, 5-azido-L-ornithine, 5-azido-d-ornithine, 6-azido-L-lysine, or 6-azido-D-lysine;
the N- or C-terminal amino acid residue of the other of the first and second center cores is a cysteine residue, and the coupling arm has a DBCO, a DIFO, a BCN, or a DICO group at the free-terminus thereof; and
the first and second center cores are coupled to each other via SPAAC reaction occurred between the N- or C-terminal amino acid residue and the coupling arm.

20. The molecular construct of claim 1, wherein the tissue plasminogen activator is alteplase, reteplase, tenecteplase, or lanoteplase.

21. The molecular construct of claim 1, wherein the inhibitor of Factor Xa is apixaban, edoxaban, or rivaroxaban; and the inhibitor of thrombin is argatroban or melagatran.

22. The molecular construct of claim 1, further comprising a third linking arm linked to the first or the second linker unit.

23. The molecular construct of claim 22, wherein the third linking arm has a maleimide group at the free terminus thereof, and a third element is linked to the third linking arm via thiol-maleimide reaction.

24. The molecular construct of claim 23, wherein the third element is different from the first element and the second element.

25. The molecular construct of claim 24, wherein the third element is a long PEG chain having a molecular weight of about 20,000 to 50,000 Daltons.

* * * * *